United States Patent
Fandl et al.

(10) Patent No.: US 7,119,066 B2
(45) Date of Patent: *Oct. 10, 2006

(54) MODIFIED CILIARY NEUROTROPHIC FACTOR (CNTF)

(75) Inventors: James P. Fandl, Lagrangeville, NY (US); Neil E. Stahl, Carmel, NY (US); Stanley J. Wiegand, Croton-on-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 702 days.

This patent is subject to a terminal disclaimer.

(21) Appl. No.: 10/281,643

(22) Filed: Oct. 28, 2002

(65) Prior Publication Data

US 2003/0144199 A1 Jul. 31, 2003

Related U.S. Application Data

(60) Division of application No. 09/031,693, filed on Feb. 27, 1998, now Pat. No. 6,472,178, which is a continuation-in-part of application No. 08/645,107, filed on May 13, 1996, now Pat. No. 6,410,510, which is a continuation-in-part of application No. 08/308,736, filed on Sep. 14, 1994, now Pat. No. 5,846,935, which is a continuation-in-part of application No. 07/959,284, filed on Oct. 9, 1992, now Pat. No. 5,349,056.

(51) Int. Cl.
*C07K 14/475* (2006.01)
*A61K 38/18* (2006.01)

(52) U.S. Cl. .................................... 514/12; 530/399
(58) Field of Classification Search ................. 514/12; 530/399
See application file for complete search history.

(56) References Cited

U.S. PATENT DOCUMENTS 5,846,935 A * 12/1998 Panayotatos .............. 514/12

FOREIGN PATENT DOCUMENTS

EP 0446931 A1 9/1991
WO WO/98221128 5/1998

OTHER PUBLICATIONS

Rudinger, In "Peptide Hormones" (ed. J.A. Parsons), University Park Press, Baltimore, pp. 1-7 (1976).*
Gloaguen, I., et al PNAS. 94:6456-6461 (1997).
Masiakowski, P et al. J Neuro57(3): 1003-1012 (1991).
Panaytatos, N. et al. J Biol. Chem 268(25): 19000-19003 (1993).
Panaytatos, N. et al.Biochem 33(19):5813-5818 (1994).
A double-blind placebo controlled clinical trial of subcutaneous recombinant ciliary neurotrophic factor (rCNTF) in amyotrophic lateral sclerosis. Neurology 46:1244-1249 (1996).

* cited by examiner

*Primary Examiner*—Robert C. Hayes
(74) *Attorney, Agent, or Firm*—Valeta Gregg, Esq.

(57) ABSTRACT

Modified ciliary neurotrophic factor, methods for production and methods of use, especially in the treatment of Huntington's disease, obesity, and gestational or adult onset diabetes.

2 Claims, 19 Drawing Sheets

Fig. 1B

```
              110       120       130       140       150       160       170       180       190       200
                                                     Bsa1                                  BamH1
hu   TEGDFHQAIHTLLLQVAAFAYQIEELMILLEYKIPRNEADGMPINVGDGGLFEKKLWGLKVIQELSQWTVRSIHDLRFISSHQTGIPARGSHYIANNKKM
rt   .........M...S............V......Q....E.........AT.........................V....M..S.LE...G.KD.Q.
rb   A...HF....................V...CN..PKD...T.V-I.GD..............H............V..C......H......D.E.
ms   .........T...S............L...A...Q..-V....VTI.............................V...HM..S.H-..G...-.Q.
ch   .DAELGP.LAAM....S..V.HL...LE-..SRGAPA.EGSE.PAPPRLS...Q..R..R..R..A..A....VR..QL.K.G--.GS.AALGLPESQ-

186  .........................................................................................
187  .........M...S............L......V....Q....E........AT....................................
188  ...........................................................................................
189  .........M...S............L......V....Q....E........AT..................V....M..S.LE...G.KD.Q.
192  .........M...S............L......V....Q....E........AT..................V....M..S.LE...G.KD.Q.
218  ...........................................................................................
219  ...........................................................................................
222  ...........................................................................................
223  ...........................................................................................
228  ...........................................................................................
              110       120       130       140       150       160       170       180       190       200
```

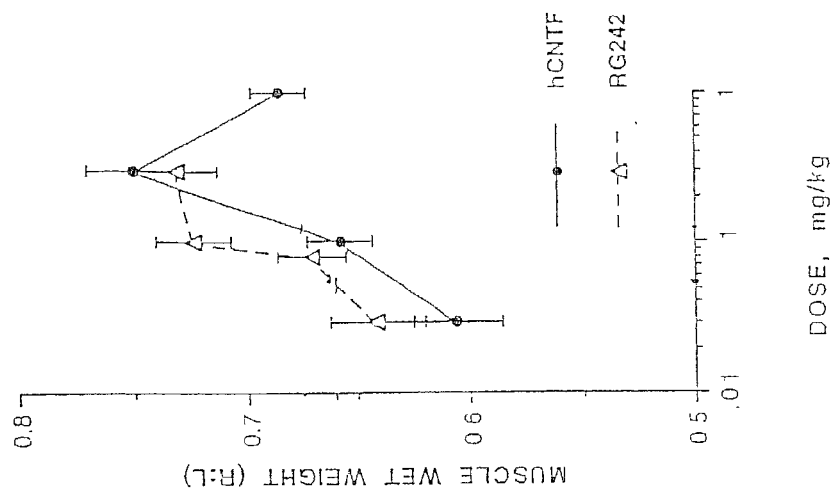
Fig. 11A    Fig. 11B
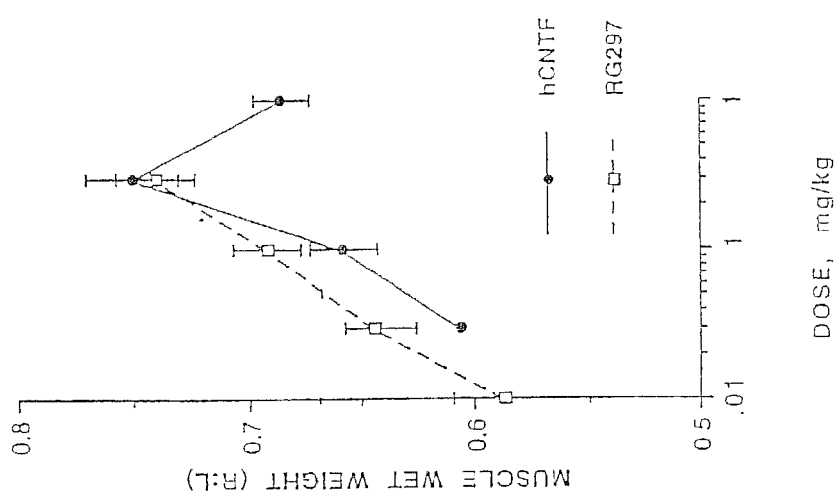
Fig. 11C
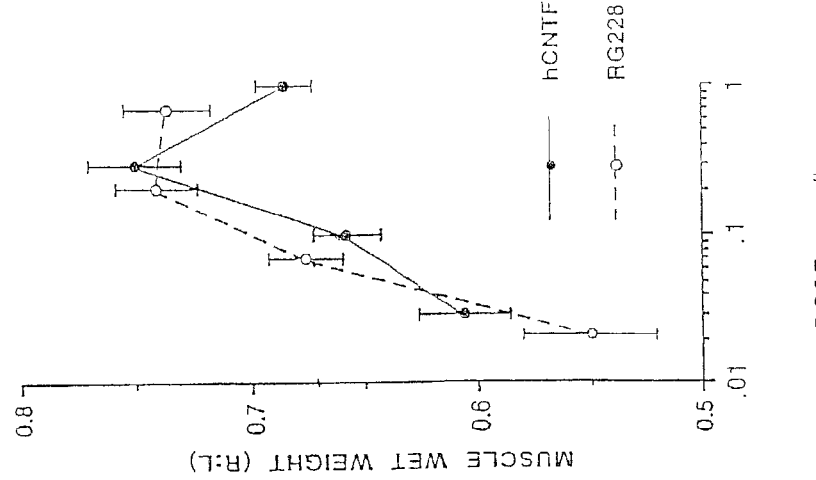

Fig. 13.
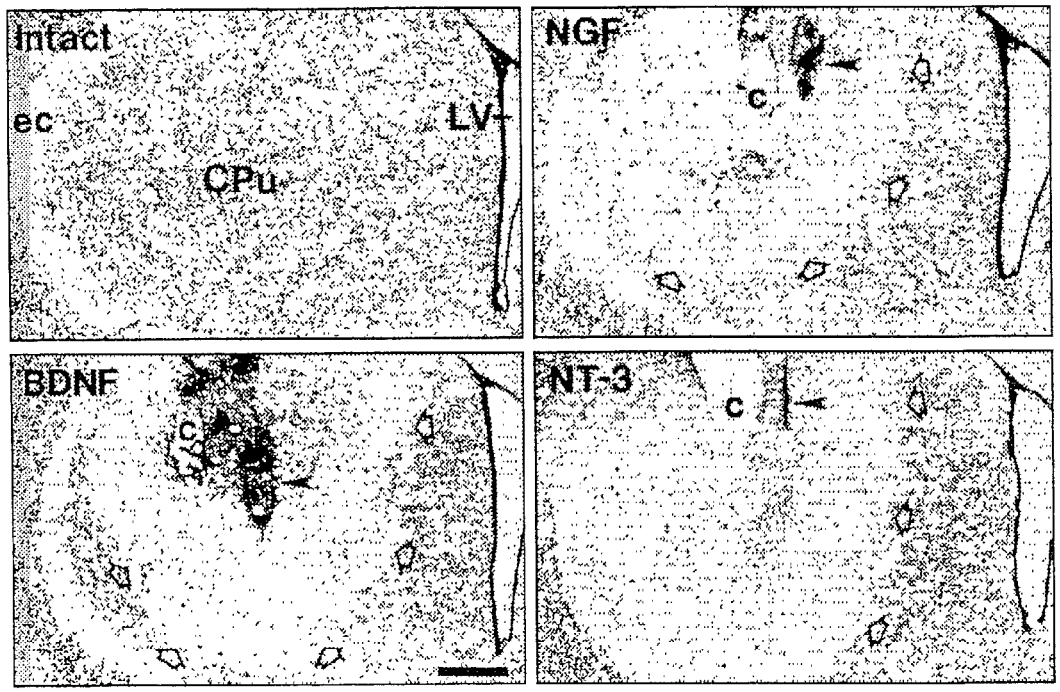
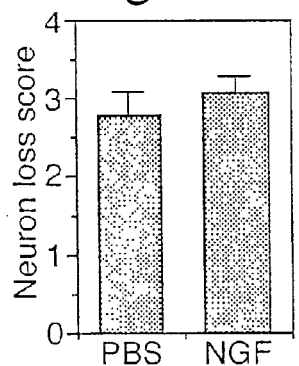
Fig. 15A.
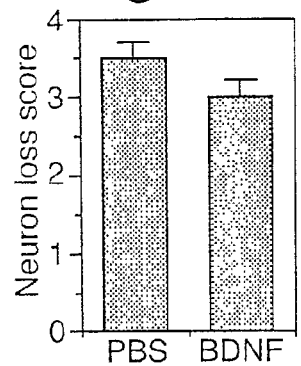
Fig. 15B.
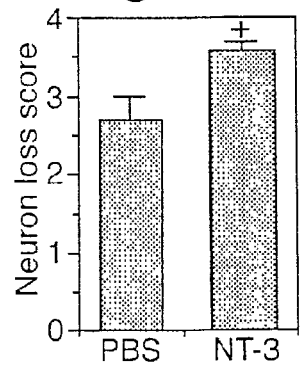
Fig. 15C.
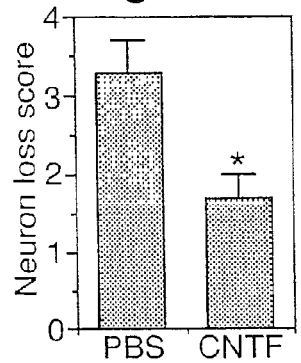
Fig. 15D.
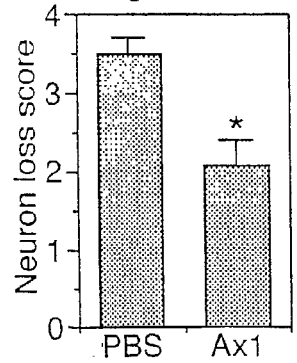
Fig. 15E.

SEQUENCE LISTING

```
<160> NUMBER OF SEQ ID NOS: 28

<210> SEQ ID NO 1
<211> LENGTH: 200
<212> TYPE: PRT
<213> ORGANISM: HUMAN

<400> SEQUENCE: 1

Met Ala Phe Thr Glu His Ser Pro Leu Thr Pro His Arg Arg Asp Leu
  1               5                  10                  15

Cys Ser Arg Ser Ile Trp Leu Ala Arg Lys Ile Arg Ser Asp Leu Thr
                 20                  25                  30

Ala Leu Thr Glu Ser Tyr Val Lys His Gln Gly Leu Asn Lys Asn Ile
             35                  40                  45

Asn Leu Asp Ser Ala Asp Gly Met Pro Val Ala Ser Thr Asp Gln Trp
         50                  55                  60

Ser Glu Leu Thr Glu Ala Glu Arg Leu Gln Glu Asn Leu Gln Ala Tyr
 65                  70                  75                  80

Arg Thr Phe His Val Leu Leu Ala Arg Leu Leu Glu Asp Gln Gln Val
                 85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
            115                 120                 125

Leu Leu Glu Tyr Lys Ile Pro Arg Asn Glu Ala Asp Gly Met Pro Ile
        130                 135                 140

Asn Val Gly Asp Gly Gly Leu Phe Glu Lys Lys Leu Trp Gly Leu Lys
```

```
                145                 150                 155                 160
Val Leu Gln Glu Leu Ser Gln Trp Thr Val Arg Ser Ile His Asp Leu
                165                 170                 175
Arg Phe Ile Ser Ser His Gln Thr Gly Ile Pro Ala Arg Gly Ser His
                180                 185                 190
Tyr Ile Ala Asn Asn Lys Lys Met
        195                 200

<210> SEQ ID NO 2
<211> LENGTH: 200
<212> TYPE: PRT
<213> ORGANISM: RAT

<400> SEQUENCE: 2

Met Ala Phe Ala Glu Gln Thr Pro Leu Thr Leu His Arg Arg Asp Leu
 1               5                  10                  15
Cys Ser Arg Ser Ile Trp Leu Ala Arg Lys Ile Arg Ser Asp Leu Thr
                20                  25                  30
Ala Leu Met Glu Ser Tyr Val Lys His Gln Gly Leu Asn Lys Asn Ile
            35                  40                  45
Asn Leu Asp Ser Val Asp Gly Val Pro Val Ala Ser Thr Asp Arg Trp
        50                  55                  60
Ser Glu Met Thr Glu Ala Glu Leu Arg Gln Glu Asn Leu Gln Ala Tyr
65                  70                  75                  80
Arg Thr Phe Gln Gly Met Leu Thr Lys Leu Leu Glu Asp Gln Arg Val
                85                  90                  95
His Phe Thr Pro Thr Glu Gly Asp Phe His Gln Ala Ile His Thr Leu
                100                 105                 110
Met Leu Gln Val Ser Ala Phe Ala Tyr Gln Leu Glu Glu Leu Met Val
            115                 120                 125
Leu Leu Glu Gln Lys Ile Pro Glu Asn Glu Ala Asp Gly Met Pro Ala
        130                 135                 140
Thr Val Gly Asp Gly Gly Leu Phe Glu Lys Lys Leu Trp Gly Leu Lys
145                 150                 155                 160
Val Leu Gln Glu Leu Ser Gln Trp Thr Val Arg Ser Ile His Asp Leu
                165                 170                 175
Arg Val Ile Ser Ser His Gln Met Gly Ile Ser Ala Leu Glu Ser His
                180                 185                 190
Tyr Gly Ala Lys Asp Lys Gln Met
        195                 200

<210> SEQ ID NO 3
<211> LENGTH: 199
<212> TYPE: PRT
<213> ORGANISM: RABBIT

<400> SEQUENCE: 3

Met Ala Phe Met Glu His Ser Ala Leu Thr Pro His Arg Arg Glu Leu
 1               5                  10                  15
Cys Ser Arg Thr Ile Trp Leu Ala Arg Lys Ile Arg Ser Asp Leu Thr
                20                  25                  30
Ala Leu Thr Glu Ser Tyr Val Lys His Gln Gly Leu Asn Lys Asn Ile
            35                  40                  45
Asn Leu Asp Ser Val Asp Gly Val Pro Met Ala Ser Thr Asp Gln Trp
        50                  55                  60
Ser Glu Leu Thr Glu Ala Glu Arg Leu Gln Glu Asn Leu Gln Ala Tyr
```

-continued

```
            65                  70                  75                  80
Arg Thr Phe His Ile Met Leu Ala Arg Leu Leu Glu Asp Gln Gln Val
                    85                  90                  95

His Phe Thr Pro Ala Glu Gly Asp His Phe Gln Ala Ile His Thr Leu
                100                 105                 110

Leu Leu Gln Val Ala Ala Phe Ala Tyr Gln Ile Glu Glu Leu Met Val
            115                 120                 125

Leu Leu Glu Cys Asn Ile Pro Pro Lys Asp Ala Asp Gly Thr Pro Val
        130                 135                 140

Ile Gly Gly Asp Gly Leu Phe Glu Lys Lys Leu Trp Gly Leu Lys Val
145                 150                 155                 160

Leu Gln Glu Leu Ser His Trp Thr Val Arg Ser Ile His Asp Leu Arg
                165                 170                 175

Val Ile Ser Cys His Gln Thr Gly Ile Pro Ala His Gly Ser His Tyr
            180                 185                 190

Ile Ala Asn Asp Lys Glu Met
        195
```

<210> SEQ ID NO 4
<211> LENGTH: 186
<212> TYPE: PRT
<213> ORGANISM: MOUSE

<400> SEQUENCE: 4

```
Met Ala Phe Ala Glu Gln Ser Pro Leu Thr Leu His Arg Arg Asp Leu
1                5                  10                  15

Cys Ser Arg Ser Ile Trp Leu Ala Arg Lys Ile Arg Ser Asp Leu Thr
                20                  25                  30

Ala Leu Met Glu Ser Tyr Val Lys His Gln Gly Leu Asn Lys Asn Ile
            35                  40                  45

Ser Leu Asp Ser Val Asp Pro Val Ala Ser Thr Asp Arg Trp Ser Glu
        50                  55                  60

Met Thr Glu Ala Glu Arg Leu Gln Glu Asn Leu Gln Ala Tyr Arg Gln
65                  70                  75                  80

Gly Met Leu Thr Arg Leu Leu Glu Asp Gln Arg Val His Phe Thr Pro
                85                  90                  95

Thr Glu Gly Asp Phe His Gln Ala His Thr Leu Thr Gln Val Ser Ala
                100                 105                 110

Phe Ala Tyr Gln Leu Glu Glu Leu Met Ala Leu Leu Glu Gln Lys Val
            115                 120                 125

Asn Glu Ala Asp Gly Met Pro Val Thr Ile Gly Asp Gly Leu Phe
        130                 135                 140

Glu Lys Leu Trp Gly Leu Lys Val Leu Leu Ser Gln Trp Thr Val Arg
145                 150                 155                 160

Ser Ile His Asp Leu Arg Val Ile Ser Ser His His Met Gly Ile Ser
                165                 170                 175

Ala His Ser His Tyr Gly Ala Lys Gln Met
            180                 185
```

<210> SEQ ID NO 5
<211> LENGTH: 195
<212> TYPE: PRT
<213> ORGANISM: CHICKEN

<400> SEQUENCE: 5

Met Ala Ala Ala Asp Thr Pro Ser Ala Thr Leu Arg His His Asp Leu

```
                1               5                      10                     15
            Cys Ser Arg Gly Ile Arg Leu Ala Arg Lys Met Arg Ser Asp Val Thr
                            20                      25                     30

Asp Leu Leu Asp Ile Tyr Val Glu Arg Gln Gly Leu Asp Ala Ser Ile
                        35                      40                      45

Ser Val Ala Ala Val Asp Gly Val Pro Thr Ala Ala Val Glu Arg Trp
                    50                      55                      60

Ala Glu Gln Thr Gly Thr Gln Arg Leu Leu Asp Asn Leu Ala Ala Tyr
             65                      70                      75                      80

Arg Ala Phe Arg Thr Leu Leu Ala Gln Met Leu Glu Glu Gln Arg Glu
                                85                      90                      95

Leu Leu Gly Asp Thr Asp Ala Glu Leu Gly Pro Ala Leu Ala Ala Met
                            100                     105                     110

Leu Leu Gln Val Ser Ala Phe Val Tyr His Leu Glu Glu Leu Leu Glu
                        115                     120                     125

Leu Glu Ser Arg Gly Ala Pro Ala Glu Glu Gly Ser Glu Pro Pro Ala
                    130                     135                     140

Pro Pro Arg Leu Ser Leu Phe Glu Gln Lys Leu Arg Gly Leu Arg Val
            145                     150                     155                     160

Leu Arg Glu Leu Ala Gln Trp Ala Val Arg Ser Val Arg Asp Leu Arg
                                165                     170                     175

Gln Leu Ser Lys His Gly Pro Gly Ser Gly Ala Ala Leu Gly Leu Pro
                            180                     185                     190

Glu Ser Gln
                    195

<210> SEQ ID NO 6
<211> LENGTH: 200
<212> TYPE: PRT
<213> ORGANISM: Artificial Sequence
<220> FEATURE:
<223> OTHER INFORMATION: Description of Artificial Sequence:purified
      recombinant protein

<400> SEQUENCE: 6

Met Ala Phe Thr Glu His Ser Pro Leu Thr Pro His Arg Arg Asp Leu
 1               5                      10                      15

Cys Ser Arg Ser Ile Trp Leu Ala Arg Lys Ile Arg Ser Asp Leu Thr
                20                      25                      30

Ala Leu Thr Glu Ser Tyr Val Lys His Gln Gly Leu Asn Lys Asn Ile
            35                      40                      45

Asn Leu Asp Ser Val Asp Gly Val Pro Val Ala Ser Thr Asp Arg Trp
        50                      55                      60

Ser Glu Met Thr Glu Ala Glu Arg Leu Gln Glu Asn Leu Gln Ala Tyr
 65                      70                      75                      80

Arg Thr Phe Gln Gly Met Leu Thr Lys Leu Leu Glu Asp Gln Arg Val
                    85                      90                      95

His Phe Thr Pro Thr Glu Gly Asp Phe His Gln Ala Ile His Thr Leu
                100                     105                     110

Met Leu Gln Val Ser Ala Phe Ala Tyr Gln Leu Glu Glu Leu Met Val
            115                     120                     125

Leu Leu Glu Gln Lys Ile Pro Glu Asn Glu Ala Asp Gly Met Pro Ala
        130                     135                     140

Thr Val Gly Asp Gly Gly Leu Phe Glu Lys Lys Leu Trp Gly Leu Lys
145                     150                     155                     160
```

Val Leu Gln Glu Leu Ser Gln Trp Thr Val Arg Ser Ile His Asp Leu
              165                 170                 175

Arg Val Ile Ser Ser His Gln Met Gly Ile Ser Ala Leu Glu Ser His
            180                 185                 190

Tyr Gly Ala Lys Asp Lys Gln Met
        195                 200

<210> SEQ ID NO 7
<211> LENGTH: 200
<212> TYPE: PRT
<213> ORGANISM: Artificial Sequence
<220> FEATURE:
<223> OTHER INFORMATION: Description of Artificial Sequence:purified
      recombinant protein

<400> SEQUENCE: 7

Met Ala Phe Ala Glu Gln Thr Pro Leu Thr Leu His Arg Arg Asp Leu
 1               5                  10                  15

Cys Ser Arg Ser Ile Trp Leu Ala Arg Lys Ile Arg Ser Asp Leu Met
            20                  25                  30

Ala Leu Thr Glu Ser Tyr Val Lys His Gln Gly Leu Asn Lys Asn Ile
        35                  40                  45

Asn Leu Asp Ser Ala Asp Gly Met Pro Val Ala Ser Thr Asp Gln Trp
    50                  55                  60

Ser Glu Leu Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Gln Val
                85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
        115                 120                 125

Leu Leu Glu Tyr Lys Ile Pro Arg Asn Glu Ala Asp Gly Met Pro Ile
    130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
            180                 185                 190

Tyr Ile Ala Asn Asn Lys Lys Met
        195                 200

<210> SEQ ID NO 8
<211> LENGTH: 200
<212> TYPE: PRT
<213> ORGANISM: Artificial Sequence
<220> FEATURE:
<223> OTHER INFORMATION: Description of Artificial Sequence:purified
      recombinant protein

<400> SEQUENCE: 8

Met Ala Phe Thr Glu His Ser Pro Leu Thr Pro His Arg Arg Asp Leu
 1               5                  10                  15

Cys Ser Arg Ser Ile Trp Leu Ala Arg Lys Ile Arg Ser Asp Leu Thr
            20                  25                  30

Ala Leu Thr Glu Ser Tyr Val Lys His Gln Gly Leu Asn Lys Asn Ile
        35                  40                  45

-continued

```
Asn Leu Asp Ser Ala Asp Gly Met Pro Val Ala Ser Thr Asp Gln Trp
 50                  55                  60

Ser Glu Leu Thr Glu Ala Glu Arg Leu Gln Glu Asn Leu Gln Ala Tyr
 65                  70                  75                  80

Arg Thr Phe His Val Leu Leu Ala Arg Leu Leu Glu Asp Gln Gln Val
                 85                  90                  95

His Phe Thr Pro Thr Glu Gly Asp Phe His Gln Ala Ile His Thr Leu
                100                 105                 110

Leu Leu Gln Val Ala Ala Phe Ala Tyr Gln Ile Glu Glu Leu Met Ile
            115                 120                 125

Leu Leu Glu Tyr Lys Ile Pro Arg Asn Glu Ala Asp Gly Met Pro Ile
        130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Val Ile Ser Ser His Gln Met Gly Ile Ser Ala Leu Glu Ser His
                180                 185                 190

Tyr Gly Ala Lys Asp Lys Gln Met
            195                 200

<210> SEQ ID NO 9
<211> LENGTH: 200
<212> TYPE: PRT
<213> ORGANISM: Artificial Sequence
<220> FEATURE:
<223> OTHER INFORMATION: Description of Artificial Sequence:purified
      recombinant protein

<400> SEQUENCE: 9

Met Ala Phe Ala Glu Gln Thr Pro Leu Thr Leu His Arg Arg Asp Leu
  1               5                  10                  15

Cys Ser Arg Ser Ile Trp Leu Ala Arg Lys Ile Arg Ser Asp Leu Thr
                 20                  25                  30

Ala Leu Met Glu Ser Tyr Val Lys His Gln Gly Leu Asn Lys Asn Ile
             35                  40                  45

Asn Leu Asp Ser Val Asp Gly Val Pro Val Ala Ser Thr Asp Arg Trp
 50                  55                  60

Ser Glu Met Thr Glu Ala Glu Arg Leu Gln Glu Asn Leu Gln Ala Tyr
 65                  70                  75                  80

Arg Thr Phe Gln Gly Met Leu Thr Lys Leu Leu Glu Asp Gln Arg Val
                 85                  90                  95

His Phe Thr Pro Thr Glu Gly Asp Phe His Gln Ala Ile His Thr Leu
                100                 105                 110

Met Leu Gln Val Ser Ala Phe Ala Tyr Gln Leu Glu Glu Leu Met Val
            115                 120                 125

Leu Leu Glu Gln Lys Ile Pro Glu Asn Glu Ala Asp Gly Met Pro Ala
        130                 135                 140

Thr Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
                180                 185                 190

Tyr Ile Ala Asn Asn Lys Lys Met
            195                 200
```

<210> SEQ ID NO 10
<211> LENGTH: 200
<212> TYPE: PRT
<213> ORGANISM: Artificial Sequence
<220> FEATURE:
<223> OTHER INFORMATION: Description of Artificial Sequence:purified recombinant protein

<400> SEQUENCE: 10

```
Met Ala Phe Thr Glu His Ser Pro Leu Thr Pro His Arg Arg Asp Leu
 1               5                  10                  15

Cys Ser Arg Ser Ile Trp Leu Ala Arg Lys Ile Arg Ser Asp Leu Thr
            20                  25                  30

Ala Leu Thr Glu Ser Tyr Val Lys His Gln Gly Leu Asn Lys Asn Ile
        35                  40                  45

Asn Leu Asp Ser Ala Asp Gly Met Pro Val Ala Ser Thr Asp Gln Trp
    50                  55                  60

Ser Glu Leu Thr Glu Ala Glu Arg Leu Gln Glu Asn Leu Gln Ala Tyr
65                  70                  75                  80

Arg Thr Phe Gln Gly Met Leu Thr Lys Leu Leu Glu Asp Gln Arg Val
                85                  90                  95

His Phe Thr Pro Thr Glu Gly Asp Phe His Gln Ala Ile His Thr Leu
            100                 105                 110

Met Leu Gln Val Ser Ala Phe Ala Tyr Gln Leu Glu Glu Leu Met Val
        115                 120                 125

Leu Leu Glu Gln Lys Ile Pro Glu Asn Glu Ala Asp Gly Met Pro Ala
    130                 135                 140

Thr Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
            180                 185                 190

Tyr Ile Ala Asn Asn Lys Lys Met
        195                 200
```

<210> SEQ ID NO 11
<211> LENGTH: 200
<212> TYPE: PRT
<213> ORGANISM: Artificial Sequence
<220> FEATURE:
<223> OTHER INFORMATION: Description of Artificial Sequence:purified recombinant protein

<400> SEQUENCE: 11

```
Met Ala Phe Thr Glu His Ser Pro Leu Thr Pro His Arg Arg Asp Leu
 1               5                  10                  15

Cys Ser Arg Ser Ile Trp Leu Ala Arg Lys Ile Arg Ser Asp Leu Met
            20                  25                  30

Ala Leu Thr Glu Ser Tyr Val Lys His Gln Gly Leu Asn Lys Asn Ile
        35                  40                  45

Asn Leu Asp Ser Val Asp Gly Val Pro Val Ala Ser Thr Asp Arg Trp
    50                  55                  60

Ser Glu Met Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Gln Val
                85                  90                  95
```

```
His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
        115                 120                 125

Leu Leu Glu Tyr Lys Ile Pro Arg Asn Glu Ala Asp Gly Met Pro Ile
    130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
            180                 185                 190

Tyr Ile Ala Asn Asn Lys Lys Met
            195                 200

<210> SEQ ID NO 12
<211> LENGTH: 200
<212> TYPE: PRT
<213> ORGANISM: Artificial Sequence
<220> FEATURE:
<223> OTHER INFORMATION: Description of Artificial Sequence:purified
      recombinant protein

<400> SEQUENCE: 12

Met Ala Phe Thr Glu His Ser Pro Leu Thr Pro His Arg Arg Asp Leu
 1               5                  10                  15

Cys Ser Arg Ser Ile Trp Leu Ala Arg Lys Ile Arg Ser Asp Leu Thr
             20                  25                  30

Ala Leu Thr Glu Ser Tyr Val Lys His Gln Gly Leu Asn Lys Asn Ile
         35                  40                  45

Asn Leu Asp Ser Val Asp Gly Val Pro Val Ala Ser Thr Asp Arg Trp
     50                  55                  60

Ser Glu Met Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Gln Val
                85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
        115                 120                 125

Leu Leu Glu Tyr Lys Ile Pro Arg Asn Glu Ala Asp Gly Met Pro Ile
    130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
            180                 185                 190

Tyr Ile Ala Asn Asn Lys Lys Met
            195                 200

<210> SEQ ID NO 13
<211> LENGTH: 200
<212> TYPE: PRT
<213> ORGANISM: Artificial Sequence
<220> FEATURE:
<223> OTHER INFORMATION: Description of Artificial Sequence:purified
```

-continued recombinant protein

<400> SEQUENCE: 13

Met Ala Phe Thr Glu His Ser Pro Leu Thr Pro His Arg Arg Asp Leu
1               5                   10                  15

Cys Ser Arg Ser Ile Trp Leu Ala Arg Lys Ile Arg Ser Asp Leu Thr
            20                  25                  30

Ala Leu Thr Glu Ser Tyr Val Lys His Gln Gly Leu Asn Lys Asn Ile
        35                  40                  45

Asn Leu Asp Ser Val Asp Gly Met Pro Val Ala Ser Thr Asp Gln Trp
    50                  55                  60

Ser Glu Met Thr Glu Ala Glu Arg Leu Gln Glu Asn Leu Gln Ala Tyr
65                  70                  75                  80

Arg Thr Phe His Val Leu Leu Ala Arg Leu Glu Asp Gln Gln Val
                85                  90                  95

His Phe Thr Pro Thr Glu Gly Asp Phe His Gln Ala Ile His Thr Leu
                100                 105                 110

Leu Leu Gln Val Ala Ala Phe Ala Tyr Gln Ile Glu Glu Leu Met Ile
            115                 120                 125

Leu Leu Glu Tyr Lys Ile Pro Arg Asn Glu Ala Asp Gly Met Pro Ile
        130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
                180                 185                 190

Tyr Ile Ala Asn Asn Lys Lys Met
            195                 200

<210> SEQ ID NO 14
<211> LENGTH: 200
<212> TYPE: PRT
<213> ORGANISM: Artificial Sequence
<220> FEATURE:
<223> OTHER INFORMATION: Description of Artificial Sequence:purified
      recombinant protein

<400> SEQUENCE: 14

Met Ala Phe Thr Glu His Ser Pro Leu Thr Pro His Arg Arg Asp Leu
1               5                   10                  15

Cys Ser Arg Ser Ile Trp Leu Ala Arg Lys Ile Arg Ser Asp Leu Thr
            20                  25                  30

Ala Leu Thr Glu Ser Tyr Val Lys His Gln Gly Leu Asn Lys Asn Ile
        35                  40                  45

Asn Leu Asp Ser Val Asp Gly Val Pro Val Ala Ser Thr Asp Gln Trp
    50                  55                  60

Ser Glu Leu Thr Glu Ala Glu Arg Leu Gln Glu Asn Leu Gln Ala Tyr
65                  70                  75                  80

Arg Thr Phe His Val Leu Leu Ala Arg Leu Glu Asp Gln Gln Val
                85                  90                  95

His Phe Thr Pro Thr Glu Gly Asp Phe His Gln Ala Ile His Thr Leu
                100                 105                 110

Leu Leu Gln Val Ala Ala Phe Ala Tyr Gln Ile Glu Glu Leu Met Ile
            115                 120                 125

Leu Leu Glu Tyr Lys Ile Pro Arg Asn Glu Ala Asp Gly Met Pro Ile

```
            130                 135                 140
Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
            180                 185                 190

Tyr Ile Ala Asn Asn Lys Lys Met
            195                 200

<210> SEQ ID NO 15
<211> LENGTH: 200
<212> TYPE: PRT
<213> ORGANISM: Artificial Sequence
<220> FEATURE:
<223> OTHER INFORMATION: Description of Artificial Sequence:purified
      recombinant protein

<400> SEQUENCE: 15

Met Ala Phe Thr Glu His Ser Pro Leu Thr Pro His Arg Arg Asp Leu
  1               5                  10                  15

Cys Ser Arg Ser Ile Trp Leu Ala Arg Lys Ile Arg Ser Asp Leu Thr
                 20                  25                  30

Ala Leu Thr Glu Ser Tyr Val Lys His Gln Gly Leu Asn Lys Asn Ile
             35                  40                  45

Asn Leu Asp Ser Ala Asp Gly Met Pro Val Ala Ser Thr Asp Arg Trp
         50                  55                  60

Ser Glu Leu Thr Glu Ala Glu Arg Leu Gln Glu Asn Leu Gln Ala Tyr
 65                  70                  75                  80

Arg Thr Phe His Val Leu Leu Ala Arg Leu Leu Glu Asp Gln Gln Val
                 85                  90                  95

His Phe Thr Pro Thr Glu Gly Asp Phe His Gln Ala Ile His Thr Leu
                100                 105                 110

Leu Leu Gln Val Ala Ala Phe Ala Tyr Gln Ile Glu Glu Leu Met Ile
            115                 120                 125

Leu Leu Glu Tyr Lys Ile Pro Arg Asn Glu Ala Asp Gly Met Pro Ile
130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
            180                 185                 190

Tyr Ile Ala Asn Asn Lys Lys Met
            195                 200

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 16
acggtaagct tggaggttct c                                           21

<210> SEQ ID NO 17
<211> LENGTH: 48
```

```
<212> TYPE: DNA
<213> ORGANISM: Artificial Sequence
<220> FEATURE:
<223> OTHER INFORMATION: Description of Artificial Sequence:primer

<400> SEQUENCE: 17
tctatctggc tagcaaggaa gattcgttca gacctgactg ctcttacg          48

<210> SEQ ID NO 18
<211> LENGTH: 69
<212> TYPE: DNA
<213> ORGANISM: Artificial Sequence
<220> FEATURE:
<223> OTHER INFORMATION: Description of Artificial Sequence:primer

<400> SEQUENCE: 18
aaggtacgat aagcttggag gttctcttgg agtcgctctg cctcagtcag ctcactccaa    60
cgatcagtg                                                             69

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 19
tctatctggc tagcaaggaa g                                       21

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 20
ccagatagag gagttaatga tactcct                                 27

<210> SEQ ID NO 21
<211> LENGTH: 47
<212> TYPE: DNA
<213> ORGANISM: Artificial Sequence
<220> FEATURE:
<223> OTHER INFORMATION: Description of Artificial Sequence:primer

<400> SEQUENCE: 21
gcgtcggccg cggaccacgc tcattaccca gtctgtgaga agaaatg           47

<210> SEQ ID NO 22
<211> LENGTH: 184
<212> TYPE: PRT
<213> ORGANISM: Artificial Sequence
<220> FEATURE:
<223> OTHER INFORMATION: Description of Artificial Sequence:purified
      recombinant protein

<400> SEQUENCE: 22

Ala Phe Thr Glu His Ser Pro Leu Thr Pro His Arg Arg Asp Leu Ala
 1               5                  10                  15

Ser Arg Ser Ile Trp Leu Ala Arg Lys Ile Arg Ser Asp Leu Thr Ala
            20                  25                  30

Leu Thr Glu Ser Tyr Val Lys His Gln Gly Leu Asn Lys Asn Ile Asn
        35                  40                  45
```

-continued

Leu Asp Ser Ala Asp Gly Met Pro Val Ala Ser Thr Asp Arg Trp Ser
    50                  55                  60

Glu Leu Thr Glu Ala Glu Arg Leu Gln Glu Asn Leu Gln Ala Tyr Arg
 65                  70                  75                  80

Thr Phe His Val Leu Leu Ala Arg Leu Leu Glu Asp Gln Gln Val His
                 85                  90                  95

Phe Thr Pro Thr Glu Gly Asp Phe His Gln Ala Ile His Thr Leu Leu
            100                 105                 110

Leu Gln Val Ala Ala Phe Ala Tyr Gln Ile Glu Glu Leu Met Ile Leu
        115                 120                 125

Leu Glu Tyr Lys Ile Pro Arg Asn Glu Ala Asp Gly Met Pro Ile Asn
    130                 135                 140

Val Gly Asp Gly Leu Phe Glu Lys Leu Trp Gly Leu Lys Val
145                 150                 155                 160

Leu Gln Glu Leu Ser Gln Trp Thr Val Arg Ser Ile His Asp Leu Arg
                165                 170                 175

Phe Ile Ser Ser His Gln Thr Gly
            180

<210> SEQ ID NO 23
<211> LENGTH: 185
<212> TYPE: PRT
<213> ORGANISM: Artificial Sequence
<220> FEATURE:
<223> OTHER INFORMATION: Description of Artificial Sequence:purified
      recombinant protein

<400> SEQUENCE: 23

Met Ala Phe Thr Glu His Ser Pro Leu Thr Pro His Arg Arg Asp Leu
 1               5                  10                  15

Ala Ser Arg Ser Ile Trp Leu Ala Arg Lys Ile Arg Ser Asp Leu Thr
                20                  25                  30

Ala Leu Thr Glu Ser Tyr Val Lys His Gln Gly Leu Asn Lys Asn Ile
            35                  40                  45

Asn Leu Asp Ser Ala Asp Gly Met Pro Val Ala Ser Thr Asp Arg Trp
    50                  55                  60

Ser Glu Leu Thr Glu Ala Glu Arg Leu Gln Glu Asn Leu Gln Ala Tyr
 65                  70                  75                  80

Arg Thr Phe His Val Leu Leu Ala Arg Leu Leu Glu Asp Gln Gln Val
                 85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
        115                 120                 125

Leu Leu Glu Tyr Lys Ile Pro Arg Asn Glu Ala Asp Gly Met Pro Ile
    130                 135                 140

Asn Val Gly Asp Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly
            180                 185

<210> SEQ ID NO 24
<211> LENGTH: 187
<212> TYPE: PRT
<213> ORGANISM: HUMAN

-continued

```
<400> SEQUENCE: 24

Met Ala Phe Thr Glu His Ser Pro Leu Thr Pro His Arg Arg Asp Leu
1               5                   10                  15

Ala Ser Arg Ser Ile Trp Leu Ala Arg Lys Ile Arg Ser Asp Leu Thr
            20                  25                  30

Ala Leu Thr Glu Ser Tyr Val Lys His Gln Gly Leu Asn Lys Asn Ile
        35                  40                  45

Asn Leu Asp Ser Ala Asp Gly Met Pro Val Ala Ser Thr Asp Arg Trp
    50                  55                  60

Ser Glu Leu Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Gln Val
                85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
        115                 120                 125

Leu Leu Glu Tyr Lys Ile Pro Arg Asn Glu Ala Asp Gly Met Pro Ile
    130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro
            180                 185

<210> SEQ ID NO 25
<211> LENGTH: 187
<212> TYPE: PRT
<213> ORGANISM: HUMAN

<400> SEQUENCE: 25

Met Ala Phe Thr Glu His Ser Pro Leu Thr Pro His Arg Arg Asp Leu
1               5                   10                  15

Cys Ser Arg Ser Ile Trp Leu Ala Arg Lys Ile Arg Ser Asp Leu Thr
            20                  25                  30

Ala Leu Thr Glu Ser Tyr Val Lys His Gln Gly Leu Asn Lys Asn Ile
        35                  40                  45

Asn Leu Asp Ser Ala Asp Gly Met Pro Val Ala Ser Thr Asp Gln Trp
    50                  55                  60

Ser Glu Leu Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Gln Val
                85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
        115                 120                 125

Leu Leu Glu Tyr Lys Ile Pro Arg Asn Glu Ala Asp Gly Met Pro Ile
    130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175
```

```
Arg Phe Ile Ser Ser His Gln Thr Gly Ile Pro
            180                 185

<210> SEQ ID NO 26
<211> LENGTH: 187
<212> TYPE: PRT
<213> ORGANISM: HUMAN

<400> SEQUENCE: 26

Met Ala Phe Thr Glu His Ser Pro Leu Thr Pro His Arg Arg Asp Leu
  1               5                  10                  15

Cys Ser Arg Ser Ile Trp Leu Ala Arg Lys Ile Arg Ser Asp Leu Thr
             20                  25                  30

Ala Leu Thr Glu Ser Tyr Val Lys His Gln Gly Leu Asn Lys Asn Ile
         35                  40                  45

Asn Leu Asp Ser Ala Asp Gly Met Pro Val Ala Ser Thr Asp Arg Trp
 50                  55                  60

Ser Glu Leu Thr Glu Ala Glu Arg Leu Gln Glu Asn Leu Gln Ala Tyr
 65                  70                  75                  80

Arg Thr Phe His Val Leu Leu Ala Arg Leu Leu Glu Asp Gln Gln Val
                 85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
        115                 120                 125

Leu Leu Glu Tyr Lys Ile Pro Arg Asn Glu Ala Asp Gly Met Pro Ile
    130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro
            180                 185

<210> SEQ ID NO 27
<211> LENGTH: 187
<212> TYPE: PRT
<213> ORGANISM: HUMAN

<400> SEQUENCE: 27

Met Ala Phe Thr Glu His Ser Pro Leu Thr Pro His Arg Arg Asp Leu
  1               5                  10                  15

Ala Ser Arg Ser Ile Trp Leu Ala Arg Lys Ile Arg Ser Asp Leu Thr
             20                  25                  30

Ala Leu Thr Glu Ser Tyr Val Lys His Gln Gly Leu Asn Lys Asn Ile
         35                  40                  45

Asn Leu Asp Ser Ala Asp Gly Met Pro Val Ala Ser Thr Asp Gln Trp
 50                  55                  60

Ser Glu Leu Thr Glu Ala Glu Arg Leu Gln Glu Asn Leu Gln Ala Tyr
 65                  70                  75                  80

Arg Thr Phe His Val Leu Leu Ala Arg Leu Leu Glu Asp Gln Gln Val
                 85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
        115                 120                 125
```

-continued

```
Leu Leu Glu Tyr Lys Ile Pro Arg Asn Glu Ala Asp Gly Met Pro Ile
        130                 135                 140
Asn Val Gly Asp Gly Gly Leu Phe Glu Lys Lys Leu Trp Gly Leu Lys
145                 150                 155                 160
Val Leu Gln Glu Leu Ser Gln Trp Thr Val Arg Ser Ile His Asp Leu
                165                 170                 175
Arg Phe Ile Ser Ser His Gln Thr Gly Ile Pro
            180                 185
```

<210> SEQ ID NO 28
<211> LENGTH: 187
<212> TYPE: PRT
<213> ORGANISM: HUMAN

<400> SEQUENCE: 28

```
Met Ala Phe Thr Glu His Ser Pro Leu Thr Pro His Arg Arg Asp Leu
  1               5                  10                  15
Ala Ser Arg Ser Ile Trp Leu Ala Arg Lys Ile Arg Ser Asp Leu Thr
                 20                  25                  30
Ala Leu Thr Glu Ser Tyr Val Lys His Gln Gly Leu Asn Lys Asn Ile
             35                  40                  45
Asn Leu Asp Ser Ala Asp Gly Met Pro Val Ala Ser Thr Asp Arg Ala
 50                  55                  60
Ser Glu Leu Thr Glu Ala Glu Arg Leu Gln Glu Asn Leu Gln Ala Tyr
 65                  70                  75                  80
Arg Thr Phe His Val Leu Leu Ala Arg Leu Leu Glu Asp Gln Gln Val
                 85                  90                  95
His Phe Thr Pro Thr Glu Gly Asp Phe His Gln Ala Ile His Thr Leu
                100                 105                 110
Leu Leu Gln Val Ala Ala Phe Ala Tyr Gln Ile Glu Glu Leu Met Ile
            115                 120                 125
Leu Leu Glu Tyr Lys Ile Pro Arg Asn Glu Ala Asp Gly Met Pro Ile
        130                 135                 140
Asn Val Gly Asp Gly Gly Leu Phe Glu Lys Lys Leu Trp Gly Leu Lys
145                 150                 155                 160
Val Leu Gln Glu Leu Ser Gln Trp Thr Val Arg Ser Ile His Asp Leu
                165                 170                 175
Arg Phe Ile Ser Ser His Gln Thr Gly Ile Pro
            180                 185
```

MODIFIED CILIARY NEUROTROPHIC FACTOR (CNTF)

This application is a divisional of U.S. patent application Ser. No. 09/031,693 filed Feb. 27, 1998, now U.S. Pat. No. 6,472,178, which is a continuation-in-part of U.S. patent application Ser. No. 08/645,107, file May 13, 1996, now U.S. Pat. No. 6,410,510 which is a continuation-in-part of Ser. No. 08/308,736 filed Sep. 14, 1994, now U.S. Pat. No. 5,846,935, which is a continuation-in-part of U.S. patent application Ser. No. 07/959,284, filed Oct. 9, 1992, now U.S. Pat. No. 5,349,056. These patents and publications are hereby incorporated by reference in their entireties.

BACKGROUND OF THE INVENTION

The present invention relates to therapeutic CNTF-related polypeptides useful for the treatment of neurological or other diseases or disorders.

Ciliary neurotrophic factor (CNTF) is a protein that is required for the survival of embryonic chick ciliary ganglion neurons in vitro (Manthorpe et al., 1980, J. Neurochem. 34:69–75). The ciliary ganglion is anatomically located within the orbital cavity, lying between the lateral rectus and the sheath of the optic nerve; it receives parasympathetic nerve fibers from the oculomotor nerve which innervates the ciliary muscle and sphincter pupillae.

Over the past decade, a number of biological effects have been ascribed to CNTF in addition to its ability to support the survival of ciliary ganglion neurons. CNTF is believed to induce the differentiation of bipotential glial progenitor cells in the perinatal rat optic nerve and brain (Hughes et al., 1988, Nature 335:70–73). Furthermore, it has been observed to promote the survival of embryonic chick dorsal root ganglion sensory neurons (Skaper and Varon, 1986, Brain Res. 389:39–46). In addition, CNTF supports the survival and differentiation of motor neurons, hippocampal neurons and presympathetic spinal cord neurons [Sendtner, et al., 1990, Nature 345: 440–441; Ip, et al. 1991, J. Neurosci. 11:3124–3134; Blottner, et al. 1989, Neurosci. Lett. 105: 316–320].

It has long been known that innervation of skeletal muscle plays a critical role in the maintenance of muscle structure and function. Skeletal muscle has been shown recently to be a target of positive CNTF actions. Specifically, CNTF prevents both the denervation-induced atrophy (decreased wet weight and myofiber cross sectional area) of skeletal muscle and the reduced twitch and tetanic tensions of denervated skeletal muscle. Helgren et al., 1994, Cell 76:493–504. In this model, human CNTF also produces an adverse effect that is manifested as a retardation of weight gain. This adverse effect has also been observed in clinical trials with rHCNTF for the treatment of ALS. Therefore, simultaneous measurements of muscle weight and animal body weight following denervation could be used as a measure of efficacy and adverse reaction, respectively, in response to treatment with rHCNTF or other compounds. The ratio of the potency values obtained from these measurements is defined as the therapeutic index (T.I.), expressed here as $TD_{25}/ED_{50}$, so that the higher the value of T.I., the safer the compound at a therapeutic dose.

CNTF has been cloned and synthesized in bacterial expression systems, as described by Masiakowski, et al., 1991, J. Neurosci. 57:1003–1012 and in International Publication No. WO 91/04316, published on Apr. 4, 1991, which are incorporated by reference in their entirety herein.

The receptor for CNTF (termed "CNTFRα") has been cloned, sequenced and expressed [see Davis, et al., 1991 Science 253:59–63]. CNTF and the hemopoietic factor known as leukemia inhibitory factor (LIF) act on neuronal cells via a shared signaling pathway that involves the IL-6 signal transducing component gp130 as well as a second, β-component (know as LIFR β); accordingly, the CNTF/CNTF receptor complex can initiate signal transduction in LIF responsive cells, or other cells which carry the gp130 and LIFRβ components [Ip, et al., 1992, Cell 69:1121–1132].

In addition to human CNTF, the corresponding rat (Stöckli et al., 1989, Nature 342:920–923), and rabbit (Lin et al., 1989, J. Biol. Chem. 265:8942–8947) genes have been cloned and found to encode a protein of 200 amino acids, which share about 80% sequence identity with the human gene. Both the human and rat recombinant proteins have been expressed at exceptionally high levels (up to 70% of total protein) and purified to near homogeneity.

Despite their structural and functional similarity, recombinant human and rat CNTF differ in several respects. The biological activity of recombinant rat CNTF in supporting survival and neurite outgrowth from embryonic chick ciliary neurons in culture is four times better than that of recombinant human CNTF [Masiakowski et al., 1991, J. Neurochem. 57:1003–1012]. Further, rat CNTF has a higher affinity for the human CNTF receptor than does human CNTF.

A surprising difference in the physical properties of human and rat CNTF, which are identical in size, is their different mobility on SDS gels. This difference in behavior suggests the presence of an unusual structural feature in one of the two molecules that persists even in the denatured state (Masiakowski et al., 1991, J. Neurochem. 57:1003–1012).

Mutagenesis by genetic engineering has been used extensively in order to elucidate the structural organization of functional domains of recombinant proteins. Several different approaches have been described in the literature for carrying out deletion or substitution mutagenesis. The most successful appear to be alanine scanning mutagenesis [Cunningham and Wells 1989, Science 244: 1081–1085] and homolog-scanning mutagenesis [Cunningham et al., 1989, Science 243:1330–1336]. These approaches helped identify the receptor binding domains of growth hormone and create hybrid proteins with altered binding properties to their cognate receptors.

To better understand the physical, biochemical and pharmacological properties of rHCNTF, applicant undertook rational mutagenesis of the human and rat CNTF genes based on the different biological and physical properties of their corresponding recombinant proteins (See Masiakowski, P., et al., 1991, J. Neurochem., 57:1003–1012). Applicant has found that the nature of the amino acid at position 63 could greatly enhance the affinity of human CNTF for sCNTFRα and its biological potency in vitro (Panayotatos, N., et al., J. Biol. Chem., 1993, 268:19000–19003; Panayotatos, N., et al., Biochemistry, 1994, 33: 5813–5818.

As described in copending U.S. patent application Ser. No. 07/570,651 filed Aug. 20, 1990, entitled "Ciliary Neurotrophic Factor", which is incorporated by reference in its entirety herein, one of the uses of CNTF contemplated by applicants was the use of CNTF for the treatment of Huntington's disease. Huntington's disease (HD) is an hereditary degenerative disorder of the central nervous system. The pathology underlying HD is progressive, relentless degeneration of the basal ganglia, structures deep inside the brain which are responsible for aspects of the integration of voluntary motor and cognitive activity. The onset of symptoms in HD is generally in adulthood, between the ages of 20 and 40. The characteristic manifestations of the disease are chorea and other involuntary movements, dementia, and psychiatric symptoms. Choreic movements consist of brief, involuntary, fluid movements, predominantly affecting the distal extremities. Patients often tend to "cover up" these movements by blending them into voluntary acts. HD patients also, however, display a variety of other neurological abnormalities including dystonia (sustained, abnormal posturing), tics ("habit spasms"), ataxia (incoordination) and dysarthria (slurred speech). The dementia of HD is characterized as the prototypical "subcortical" dementia. Manifestations of dementia in HD include slowness of mentation and difficulty in concentration and in sequencing tasks. Behavioral disturbances in HD patients are varied, and can include personality changes such as apathy and withdrawal; agitation, impulsiveness, paranoia, depression, aggressive behavior, delusions, psychosis, etc. The relentless motor, cognitive and behavioral decline results in social and functional incapacity and, ultimately death.

HD is inherited as an autosomal dominant trait. Its prevalence in the U.S. population is estimated to be 5 to 10 per 100,000 individuals, yielding a total prevalence of 25,000 in the US population. However, due to the late onset of symptoms, there are a number of "at-risk", asymptomatic individuals in the population as well. The prevalence of asymptomatic, at-risk patients carrying the HD gene is perhaps twice that of the symptomatic patients (W. Koroshetz and N. Wexler, personal communication). Thus, the total HD patient population eligible to receive a new therapy is about 75,000.

The gene currently believed to be responsible for the pathogenesis of HD is located at the telomeric end of the short arm of Chromosome 4. This gene codes for a structurally novel protein of unknown function, and the relationship of the gene product to the pathogenesis of HD remains uncertain at the present time.

The principal anatomical lesion in HD consists of loss of the so-called "medium spiny" neurons of the caudate nucleus and putamen (collectively known as the striatum in rodents). These neurons comprise the projection system whereby the caudate/putamen projects to its output nuclei elsewhere in the basal ganglia of the brain. The principal neurotransmitter utilized by the medium spiny neurons is gamma-aminobutyric acid (GABA), although many also contain neuropeptides such as enkephalins and substance P. It is clear, however, that in HD interneurons which do not utilize GABA as their neurotransmitter, containing instead either acetylcholine or the neuropeptides somatostatin or neuropeptide Y, are relatively undamaged in HD.

Pathological and neurochemical changes which mimic those seen in HD can be mimicked by infusion of glutamatergic agonist drugs into the striatum. Infusion of quinolinic acid under appropriate conditions produces selective depletion of medium sized intrinsic striatal neurons which utilize gamma-aminobutyric acid (GABA) as their neurotransmitter, without affecting the large, cholinergic interneurons.

There have been no successful clinical trials of either symptomatic or neuroprotective treatments in HD. However, useful, validated rating instruments and neuroimaging techniques exist which are capable of monitoring disease progress and patient function.

The CNTF receptor complex contains 3 proteins: a specificity determining α component that directly binds to CNTF, as well as 2 signal transducing β components (LIFR β and gp130) that cannot bind CNTF on their own, but are required to initiate signaling in response to CNTF. The β component of the CNTFR complex is more widely distributed throughout the body than the α component. The 3 components of the CNTFR complex are normally unassociated on the cell surface; CNTF induces the stepwise assembly of a complete receptor complex by first binding to CNTFR α, then engaging gp130, and finally recruiting LIFR β. When this final step in receptor assembly occurs (heterodimerization of the β components), intracellular signaling is initiated by activating non-receptor tyrosine kinases (JAK kinases) associated with the βcomponents. JAK kinases respond by phosphorylating each other and also tyrosine residues on the receptor cytoplasmic domains, creating phosphotyrosine docking sites for the Src homology 2 domains of STAT proteins. After their phosphorylation, bound STAT proteins dissociate from the receptor, dimerize, and translocate to the nucleus where they bind DNA and activate transcription (reviews: Frank, D. and Greenberg, M. (1996) *Perspectives on developmental neurobiology* 4: 3–18; Stahl, N. and Yancopoulos, G. (1997) *Growth factors and cytokines in health and disease* 2B, 777–809). Axokine is a mutant CNTF molecule with improved physical and chemical properties, which retains the ability to interact with and activate the CNTF receptor. (Panayotatos, N., et al. (1993) *J. Biol. Chem.* 268: 19000–19003).

Leptin, the product of the ob gene, is secreted by adipocytes and functions as a peripheral signal to the brain to regulate food intake and energy metabolism (Zhang, Y., et al. (1994) *Nature* 372: 425–431). Interestingly, leptin receptor (OB-R), a single membrane-spanning receptor has considerable sequence similarities to gp130 (Tartaglia, L., et al. (1995) *Cell* 83: 1263–1271), and like CNTF, leptin signals through the JAK/STAT pathway (Baumann, H., et al. (1996) *Proc. Natl. Acad. Sci. USA* 93: 8374–8378; Ghilardi, N., et al. (1996) *Proc. Natl. Acad. Sci. USA* 93: 6231–6235). Systemic administration of both CNTF and leptin resulted in induction of tis-11 (Gloaguen, I., et al. (1997) *Proc. Natl. Acad. Sci. USA* 94: 6456–6461) and STAT3 (Vaisse, C., et al. (1996) *Nature Gen.* 14: 95–97) in the hypothalamic satiety center, indicating their roles in the regulation of body weight and feeding behavior. Indeed, adminstration of CNTF to humans reduced food intake and resulted in weight loss (Group, A. C. T. S. (1996) *Neurology* 46:1244–1249.).

SUMMARY OF THE INVENTION

An object of the present invention is to provide novel CNTF-related neurotrophic factors for the treatment of diseases or disorders including, but not limited to, motor neuron diseases and muscle degenerative diseases. In a preferred embodiment, CNTF and related molecules are utilized for the treatment of Huntington's disease.

A further object of the present invention is to provide a method for identifying CNTF-related factors, other than those specifically described herein, that have improved therapeutic properties.

These and other objects are achieved in accordance with the invention, whereby amino acid substitutions in human CNTF protein enhance its therapeutic properties. In one embodiment, alterations in electrophoretic mobility are used to initially screen potentially useful modified CNTF proteins.

In a preferred embodiment, the amino acid glutamine in position 63 of human CNTF (SEQ ID NO: 1) is replaced with arginine (referred to as 63Q→R) or another amino acid which results in a modified CNTF molecule with improved biological activity. In further embodiments, rHCNTF variants combine the 63Q→R mutation (SEQ ID NO: 6) with three other novel features.

1) Deletion of the last 13 amino acid residues (referred to as ΔC13) to confer greater solubility to rHCNTF without impairing its activity;
2) Substitution of the unique cysteine residue at position 17, which results in stabilization of rHCNTF in physiological buffer, at physiological pH and temperature conditions without affecting its activity; or
3) Substitution of amino acid residue 64W, which alters the biological activity of rHCNTF in vitro and which results in a 7-fold improvement of its therapeutic index in vivo.

In another preferred embodiment, a molecule designated RG297 (rHCNTF, 17CA63QRΔC13) combines a 63Q→R substitution (which confers greater biological potency) with a deletion of the terminal 13 amino acid residues (which confers greater solubility under physiological conditions) and a 17CA substitution (which confers stability, particularly under physiological conditions at 37° C.) and shows a 2–3 fold better therapeutic index than rHCNTF in an animal model.

In another preferred embodiment, a molecule designated RG242 is described that carries the double substitution 63QR64WA which results in a different spectrum of biological potency and a 7-fold higher therapeutic index.

In another preferred embodiment, a molecule designated RG290 is described that carries the double substitution 63QRΔC13 which confers greater solubility under physiological conditions.

BRIEF DESCRIPTION OF THE FIGURES

FIG. 11—Comparison of dose dependent rescue of rat muscle wet weight of (A) hCNTF vs. RG228; (B) hCNTF vs. RG297 and (C) hCNTF vs. RG242.

FIG. 13—Representative Nissl-stained sections (coronal plane) from brains treated with neurotrophins and injected with quinolinic acid. Top left: A view of an intact caudate-putamen (CPu). Adjacent panels: Comparable views of sections from brains treated with NGF, BDNF or NT-3 and injected with quinolinic acid. In the neurotrophin-treated brains, a circumscribed area (indicated by open arrows) is virtually devoid of medium-sized neurons. The two tracks in the CPu were left by the infusion cannula (c) and the quinolinic acid injection needle (arrowhead). ec, external capsule; LV, lateral ventricle. Scale bar=0.5 mm.

FIG. 15—Effect of treatment with neurotrophic factors on medium-sized striatal neuron loss induced by intrastriatal injection of quinolinic acid (QA). A, B, C, D, E. Mean neuron loss scores (±SEM) for groups treated with neurotrophic factor or PBS and injected with quinolinic acid. The number of rats in each trophic factor-treated group is as follows: NGF=5; BDNF=12; NT-3=10; CNTF=3; Ax1=7; equivalent numbers were used in the PBS-treated control groups in each experiment. Statistical comparisons were by unpaired t-test. NT-3 treatment resulted in a significantly greater (+) mean neuron loss score compared with the PBS-treated group: t(17)=2.75, p=0.01. CNTF or Ax1 treatment resulted in significantly lower (*) mean neuron loss scores compared with PBS-treated groups: t(5)=2.7, p=0.04 and t(13)=4.2, p=0.001, respectively.

FIG. 20A—Serum insulin levels were measured in ARK/J diet-induced obese mice following treatment with vehicle, diet restriction and Ax-15 (0.1 mg/kg) or Ax-15 only (0.1 mg/kg) to determine the effects of diet and/or Ax-15 treatment on obesity-associated hyperinsulinemia.

FIG. 20B—Serum corticosterone levels were measured in ARK/J diet-induced obese mice following treatment with vehicle, diet restriction and Ax-15 (0.1 mg/kg) or Ax-15 only (0.1 mg/kg) to determine the effects of diet and/or Ax-15 treatment on obesity-associated hyperinsulinemia.

DETAILED DESCRIPTION OF THE INVENTION

Figure 1A:
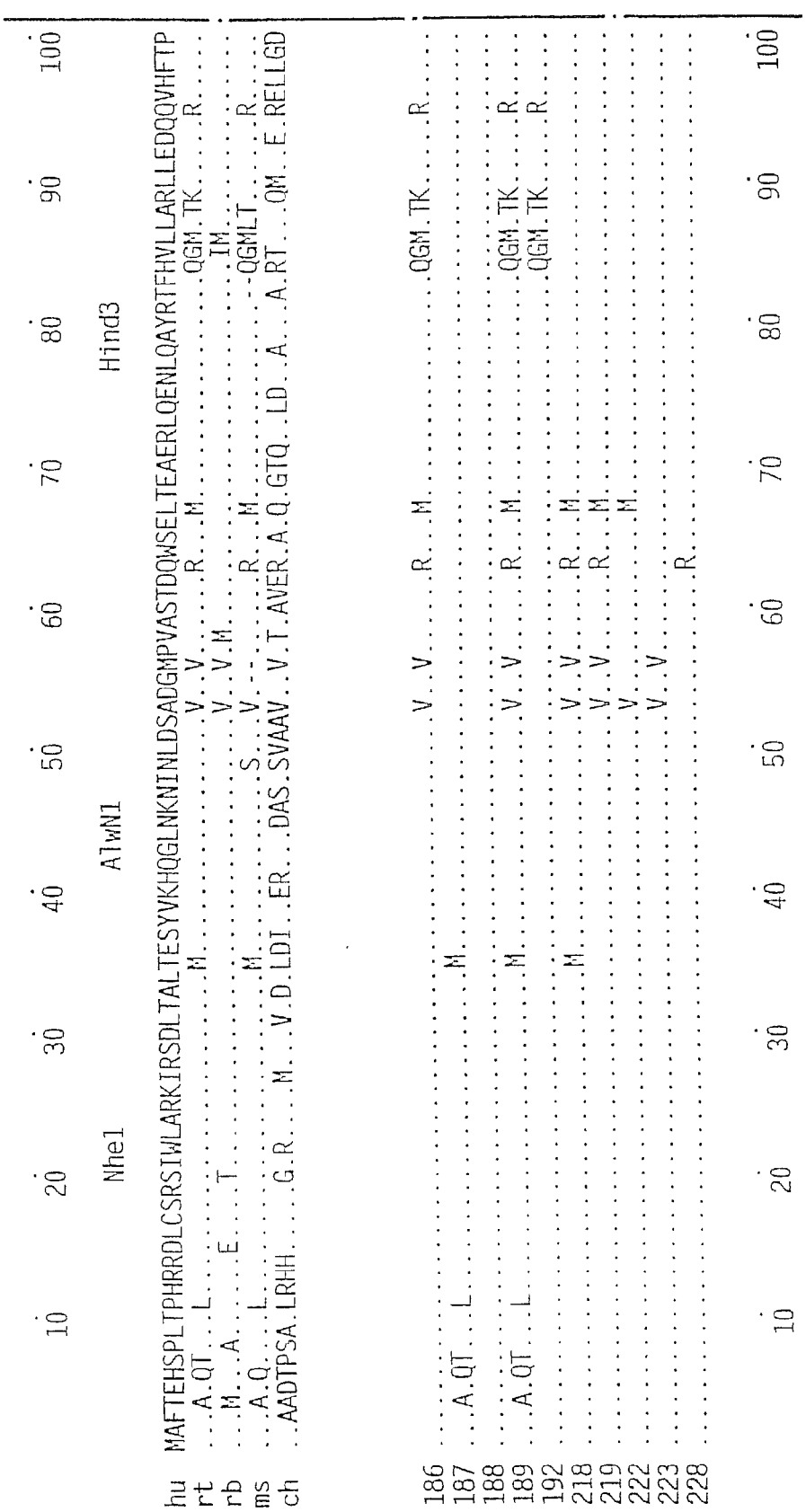
FIG. 1—Alignment of CNTF protein sequences. A. Human (SEQ ID NO:1), rat (SEQ ID NO:2), rabbit (SEQ ID NO: 3), mouse (SEQ ID NO: 4) and chicken (SEQ ID NO: 5) (Leung, et al., 1992, Neuron 8:1045–1053) sequences. Dots indicate residues found in the human sequence. Panel B. Modified CNTF molecules showing human CNTF amino acid residues (dots) and rat CNTF (residues shown). The name of the purified recombinant protein corresponding to each sequence is shown on the left (SEQ ID NOS: 6–15 respectively).

The present invention relates to a method of treating neurological diseases and disorders in humans or animals. It is based, in part, on the initial finding that recombinant rat CNTF binds more efficiently to the human CNTF receptor than does recombinant human CNTF and the subsequent discovery that amino acid substitutions which cause human CNTF to more closely resemble rat CNTF result in enhanced binding of the modified CNTF to the human CNTF receptor and concomitant enhanced biological activity.

In a preferred embodiment, alteration of a single amino acid of the human CNTF protein results in a significant enhancement of the ability of the protein to promote the survival and outgrowth of ciliary ganglion, as well as other neurons.

Recombinant human and rat CNTF have the same number of amino acids (199) and similar mass (MW 22,798 and 22,721 respectively, after removal of the N-terminal methionine). Yet, on reducing SDS-PAGE gels, recombinant human CNTF migrates as a protein of MW=27,500, whereas rat CNTF migrates with the expected mobility. In addition, human CNTF has four times lower biological activity towards chick ciliary ganglion (CG) neurons than rat CNTF and the human protein competes for binding to the human or the rat receptor on cell surfaces much less effectively than rat CNTF.

The above observation led to a directed effort to identify the region on the CNTF molecule responsible for these differences. This method involved the exchange, by genetic engineering methods, of parts of the human CNTF sequence with the corresponding rat CNTF sequence and vice versa. To achieve this, advantage was taken of restriction sites that are common to the two CNTF genes and unique in their corresponding expression vectors. When necessary, such sites were engineered in one or the other of the two genes in areas that encode the same protein sequence. With this approach, expression vectors were obtained for each of the modified proteins shown in FIG. 1 (SEQ ID NOS: 1–15). After isolating the individual proteins to at least 60% purity, their properties, as compared to those of human and rat CNTF were determined.

Because the electrophoretic mobilities of human and rat CNTF differ significantly, the effect of each amino acid substitution was monitored initially by making a determination of the effect of such change on the mobility of the protein. As described herein, electrophoretic mobility data indicated that all of the modified human CNTF molecules that migrated to the same position as rat CNTF had the single amino acid substitution Gln63→Arg (Q63→R).

Modified human CNTF proteins that demonstrated an electrophoretic mobility similar to that of the rat CNTF molecule were subsequently examined for biological activity and receptor binding.

CNTF is characterized by its capacity to support the survival of dissociated ciliary neurons of E8 chick embryos. By this criterion, purified recombinant rat CNTF is as active as the native protein from rat, but four times more active than recombinant human CNTF [Masiakowski, et al., 1991, J. Neurosci. 57:1003–1012 and in International Publication No. WO 91/04316, published on Apr. 4, 1991]. The same assay was utilized to determine the biological activity of the altered molecules prepared as described above. As described herein, all of the modified CNTF molecules that had the Q63→R substitution exhibited an increased ability to support the survival of ciliary ganglion neurons as compared to the parent human CNTF protein. Such results indicated a strong correlation between alteration of the electrophoretic mobility and enhanced biological properties.

In addition to measuring the biological effect of modifications made to human CNTF, an indication of the potential biological activity of each of the molecules may also be obtained by determining the effect of each modification on the ability of the molecules to bind to the CNTF receptor.

In one embodiment, the ability of the modified human CNTF proteins to compete with rat CNTF for binding to rat superior cervical ganglia neurons (SCGs) is measured. As described herein, human CNTF is about 90 times less potent in displacing $^{125}$I-labelled rat CNTF binding from these cells than unlabelled rat CNTF. Several of the modified human CNTF proteins described herein, however, are more potent than the human CNTF in displacing the rat protein. All of the molecules described herein that had such increased competitive binding ability were molecules that exhibited altered electrophoretic mobility, wherein the molecules migrated in a manner similar to rat CNTF.

In another embodiment, cells, such as MG87 fibroblasts, are engineered to express the human CNTF receptor α-component and such cells are used to assay the binding capability of the modified protein to the human receptor. Human CNTF is about 12 times less potent than rat CNTF in competing with $^{125}$I-labelled rat CNTF for binding to the human CNTF receptor. Several of the modified human CNTF molecules described herein, including all of those with electrophoretic mobility that resemble rat rather than human CNTF, were more potent than human CNTF in competing with binding of $^{125}$I-rat CNTF to the cells expressing the human CNTF receptor.

In another embodiment, an animal model with demonstrated utility in providing an indication of the ability of certain growth and other factors to prevent degeneration of retinal photoreceptors may be used to assess the therapeutic properties of the modified CNTF molecules according to the present invention. As described in Example 4, hCNTF (Gln63→Arg) (SEQ ID NO: 6) has a ten-fold higher ability than recombinant human CNTF to prevent degeneration of photoreceptors in a light-induced damage model of retinal degeneration.

Thus, according to the invention, certain amino acid substitutions in the human CNTF protein result in modified human CNTF proteins that exhibit enhanced binding to the human CNTF receptor and therefore, would be expected to have enhanced therapeutic properties.

The modified CNTF molecules useful for practicing the present invention may be prepared by cloning and expression in a prokaryotic or eukaryotic expression system as described, for example in Masiakowski, et al., 1991, J. Neurosci. 57:1003–1012 and in International Publication No. WO 91/04316, published on Apr. 4, 1991. The recombinant neurotrophin gene may be expressed and purified utilizing any number of methods. The gene encoding the factor may be subcloned into a bacterial expression vector, such as for example, but not by way of limitation, pCP110.

The recombinant factors may be purified by any technique which allows for the subsequent formation of a stable, biologically active protein. For example, and not by way of limitation, the factors may be recovered from cells either as soluble proteins or as inclusion bodies, from which they may be extracted quantitatively by 8M guanidinium hydrochloride and dialysis. In order to further purify the factors, conventional ion exchange chromatography, hydrophobic interaction chromatography, reverse phase chromatography or gel filtration may be used.

According to the present invention, modified CNTF molecules produced as described herein, or a hybrid or mutant thereof, may be used to promote differentiation, proliferation or survival in vitro or in vivo of cells that are responsive to CNTF, including cells that express receptors of the CNTF/IL-6/LIF receptor family, or any cells that express the appropriate signal transducing component, as described, for example, in Davis, et al., 1992, Cell 69:1121–1132. Mutants or hybrids may alternatively antagonize cell differentiation or survival.

The present invention may be used to treat disorders of any cell responsive to CNTF or the CNTF/CNTF receptor complex. In preferred embodiments of the invention, disorders of cells that express members of the CNTF/IL-6/LIF receptor family may be treated according to these methods. Examples of such disorders include but are not limited to those involving the following cells: leukemia cells, hematopoietic stem cells, megakaryocytes and their progenitors, DA1 cells, osteoclasts, osteoblasts, hepatocytes, adipocytes, kidney epithelial cells, embryonic stem cells, renal mesangial cells, T cells, B cells, etc.

Accordingly, the present invention provides for methods in which a patient suffering from a CNTF-related neurological or differentiation disorder or disease or nerve damage is treated with an effective amount of the modified CNTF, or a hybrid or mutant thereof. The modified CNTF molecules may be utilized to treat disorders or diseases as described for CNTF in International Publication No. WO91/04316 published on Apr. 4, 1991 by Masiakowski, et al. and for CNTF/CNTFR complex as described in International Publication No. WO91/19009 published on Dec. 12, 1991 by Davis, et al. both of which are incorporated by reference in their entirety herein.

Such diseases or disorders include degenerative diseases, such as retinal degenerations, diseases or disorders involving the spinal cord, cholinergic neurons, hippocampal neurons or diseases or disorders involving motorneurons, such as amyotrophic lateral sclerosis or those of the facial nerve, such as Bell's palsy. Other diseases or disorders that may be treated include peripheral neuropathy, Alzheimer's disease, Parkinson's disease, Huntington's chorea (Huntington's disease or HD), or muscle atrophy resulting from, for example, denervation, chronic disuse, metabolic stress, and nutritional insufficiency or from a condition such as muscular dystrophy syndrome, congenital myopathy, inflammatory disease of muscle, toxic myopathy, nerve trauma, peripheral neuropathy, drug or toxin-induced damage, or motor neuronopathy.

In one embodiment, CNTF or CNTF-related molecules described herein are used for the treatment of Huntington's disease. Glutamate receptor mediated excitotoxicity has been hypothesized to play a role in numerous neurodegenerative diseases or insults, including Huntington's disease. The predominant neuropathological feature of Huntington disease is a massive degeneration of the medium-sized, GABAergic, striatal output neurons, without substantial loss of striatal interneurons (Acheson, A. & R. Lindsay., 1994, Seminars Neurosci. 6:333–3410). As described in Example 7 below, Applicants have conducted studies, using both CNTF and the variants described herein, in an animal model wherein the preferential loss of striatal output neurons observed in Huntington disease, and the resulting dyskinesia, are mimicked in rodent or primate models in which an NMDA glutamate receptor agonist, quinolinic acid, is injected into the striatum (DiFiglia, M. Trends Neurosci., 1990, 13:286–289). In these studies, CNTF and its variants afforded protection against exposure to quinolinic acid. The close resemblance of the appearance of the quinolinic acid-lesioned striatum to that of patients dying with HD suggests that quinolinic acid, although it produces an acute and severe lesion in contradistinction to the relentless and relatively slow progression of HD, constitutes an adequate animal model for this devastating neurological disorder.

To date, human clinical trials using recombinant human CNTF (rHCNTF) have been limited to studies wherein subcutaneous administration of the protein was tested for its efficacy in slowing the progression of amyotrophic lateral sclerosis (ALS). Such administration of rHCNTF was associated with systemic side effects, including cough anorexia and weight loss, and, in at least one study, over 80% of patients receiving rHCNTF developed neutralizing antibodies, the significance of which is uncertain. However, despite problems with side effects and antibody formation, a subgroup of patients in the early stages of ALS appeared to derive benefit from rHCNTF administration in that these patients demonstrated a reduced rate of pulmonary function loss compared to placebo treated patients with similar disease durations.

Preliminary studies conducted by applicants, using intermittent, compartmentalized administration of rHCNTF into the CSF of ALS patients, have demonstrated no evidence of systemic side effects or antibody formation. Such studies involved the use of an infusion pump manufactured by Medtronic (SynchroMed Model 8615/Series DAA) with a side port for sampling CSF which was implanted under general anesthesia using standard techniques (Penn, et al., 1985, 2:125–127). The pump was attached to a subarachnoid catheter who tip was placed at the L1 level under fluoroscopy. Administration of 1 to 8 μg rHCNTF per hour for 48 hours each week was tolerated for periods up to 1 year in four patients with ALS. These patients did not experience the range of adverse events seen with systemic rHCNTF administration. Side effects in this patient group consisted of sciatic pain in two patients and headaches in one. Elevations in white blood cells and protein were seen in the CSF. In this study, rHCNTF displayed similar distribution and pharmacokinetic properties to small molecule drugs such as baclofen and morphine infused into the intrathecal space. Unfortunately, rHCNTF is too unstable for continuous CNS infusion therapy or for local depot administration, since it tends to form covalent dimers through its unpaired cysteine residue, leading to aggregate formation and precipitation. Accordingly, the need exists for stable preparation of CNTF that can be utilized for direct infusion in the central nervous system.

In collaboration with Aebischer, et al. (unpublished results), Applicants have implanted encapsulated BHK cells which secrete hCNTF into the subarachnoid space of 10 patients with ALS. Steady-state CSF concentrations of up to 6 ng/mL have been achieved. Although all patients complain of asthenia and fatigue, weight loss, anorexia and activation of the acute phase response proteins were not observed. There has been no CSF pleocytosis nor increase in white cell counts. CNTF cannot be detected in the peripheral blood in these patients. Results of efficacy measures to date are too sparse to permit conclusions regarding efficacy. The lack of an inflammatory response to hCNTF in patients receiving rHCNTF synthesized by implanted, encapsulated cells compared to that seen with pump-infused rHCNTF suggests that the changes seen following pump delivery of rHCNTF may well be related to formulation and stability issues surrounding this particular protein.

Accordingly, based on animal model data demonstrating the efficacy of CNTF and its variants as protective agents for exitotoxic damage of striatal neurons in an art recognized model of Huntington's disease, combined with Applicants' discovery that the side effects and antibody formation observed using systemic injection of CNTF can be avoided by delivery of CNTF or its variants directly into the CNS, applicants have discovered a useful method of treating Huntington's disease. Accordingly, applicants invention contemplates delivery of CNTF or its variants directly into the CNS via implanted cells or cellular-like vesicles, such as, for example, liposomes, which secrete CNTF. Alternatively, CNTF variants as described herein, which have improved stability and solubility as compared to CNTF, provide preferred formulations for delivery of CNTF via, for example, osmotic pumps, into the CNS as described above. Because the instability of rHCNTF in solution at body temperature interferes with its ability to be chronically administered by intrathecal or intraventricular infusion, the variants of rHCNTF described herein are preferred for such uses in view of their improved stability, solubility, and decreased antigenicity.

Accordingly, the present invention contemplates variants of CNTF with improved solubility that may be used in therapeutic applications where infusion, via, for example, osmotic pump, is used to delivery the drug. The solubility of recombinant human CNTF (rHCNTF) is very limited in physiological buffer, e.g., Phosphate-Buffered-Saline, pH 7.4 (PBS). Furthermore, the solubility over at least the 4.5–8.0 pH range depends strongly on the temperature and on the time of incubation. At 5° C., the solubility of rHCNTF in PBS is 1 mg/ml and the solution is stable for a few hours, but at 37° C. its solubility is only 0.1 mg/ml after 2 hr and 0.05 mg/ml after 48 hrs. This limited solubility and thermal stability preclude stable formulation of rHCNTF in physiological buffer. Such formulations are particularly desirable for continuous administration into the CNS.

It was discovered that rHCNTF lacking the last 13 amino acid residues from the carboxyl end (rHCNTF, ΔC13 (SEQ ID NO:25) also designated RPN160 or RG160) retains full biological activity and is soluble at low temperatures (5–10° C.) to at least 12 mg/ml. Yet, despite this far greater solubility, rHCNTF, ΔC13 (SEQ ID NO:25) still falls out of a PBS solution upon incubation at 37° C. over a period of several hours, even at concentrations as low as 0.1 mg/ml.

It was determined that the thermal instability of rHCNTF and rHCNTF, ΔC13 (SEQ ID NO:25) was the result of aggregation that was initiated by intermolecular disulfide bond formation and depended strongly on protein concentration and temperature. By replacing the single cysteine residue at position 17 of human CNTF with an alanine residue, proteins were obtained that show far greater stability and maintain their biological activity after incubation for at least 7 days in PBS at 37° C. This property is maintained in rHCNTF,63QR (SEQ ID NO:6) variants which have higher potency due to the substitution of the glutamine residue at position 63 by arginine. In a particular example, rHCNTF,17CA,63QR, ΔC13 (SEQ ID NO:24) (also designated RG297) shows greater biological potency than rHCNTF because of the 63QR substitution, greater solubility because of the ΔC13 deletion and greater stability because of the 17CA substitution.

The present invention contemplates treatment of a patient having HD with a therapeutically effective amount of CNTF or the variants described herein. Effective amounts of CNTF or its variants are amounts which result in the slowing of the progression of the disease, or of a reduction in the side-effects associated with the disease. The efficacy of the treatment may be measured by comparing the effect of the treatment as compared to controls which receive no treatment. The clinical course and natural history of HD have been extensively characterized both in field studies (Young et al., 1996, Ann Neurol. 20:296–303; Penney and Young, 1990, Movement Disorders 5:93–99), the development of clinical rating instruments (Shoulson and Fahn, 1979, Neurology 29:1–3; Shoulson et al, 1989, Quantification of Neurologic Deficit, T L Munsat (ed) Butterworths 271–284.; Feigin et al., 1995, Movement Disorders 10:211–214), and radiographic correlates of disease progression using computed X-ray tomography (Terrence et al., 1977, Neuroradiology 13:173–175; Barr et al., 1978, Neurology 28:1196–1200; Neophytides et al., 1979, 23:185–191; Stober et al., 1984, Neuroradiology 26:25–28); magnetic resonance imaging (Grafton et al., 1992, Arch. Neurol. 49:1161–1167) and positron emission tomographic techniques (Harris, et al., 1996, Arch. Neurol. 53:316–324).

Clinical rating of the progression of Huntington's disease has been assessed using the HD Functional Capacity Scale (HDFC) developed by Shoulson and Fahn (1979, Neurology 29:1–3). A fully functional patient receives a score of 13 on this scale; a score of 0 reflects total disability Shoulson et al., 1989, Quantification of Neurologic Deficit, T L Munsat (ed) Butterworths 271–284. The average rate of progression of patients using this scale is approximately 0.65 units/year. Shoulson et al., 1989, Quantification of Neurologic Deficit, T L Munsat (ed) Butterworths 271–284; Feigin et al., 1995, Movement Disorders 10:211–214. If this scale is truly linear (an hypothesis which has not been tested) this rate of progression would correspond nicely with the average 20 year duration of symptomatic HD in patients. HDFC scores can be roughly grouped into 5 clinical stages (Shoulson et al., 1989, Quantification of Neurologic Deficit, T L Munsat (ed) Butterworths 271–284).

Neuroimaging studies have focused on the gross pathological consequences of neuronal loss and consequent atrophy of basal ganglia structures. As HD progresses, the caudate nuclei shrink, giving a characteristic "box-car" appearance to the lateral ventricles. The degree of caudate atrophy can be quantified using a "bicaudate index".

Magnetic resonance imaging may be used to generate similar indices to those given by CT. A relatively new technique, in vivo NMR spectroscopy, however, offers the ability to assess metabolic processes within the living brain. One preliminary study (Jenkins, et al., 1993, Neurology 43:2689–2695 has detected an increased amount of lactic acid, presumably reflecting either neuronal cell loss or a defect in intermediary metabolism, in the brains of HD patients.

Positron Emission tomographic (PET) permits functional imaging to be performed in living patients. Changes in metabolic state can be assessed using 2-deoxyglucose (which reflects synaptic activity), or selective radioligands which mark selected neuronal populations. To determine the rate of change of glucose metabolism and caudate size in persons at risk for Huntington's disease, Grafton et al., (1992, Arch Neurol. 49:1161–1167) evaluated 18 persons at risk for Huntington's disease with two positron emission tomographic glucose metabolic studies and two magnetic resonance imaging scans separated by 42 (+/−9) months. Seven of the individuals were Huntington' disease gene negative; the remainder were gene positive by genetic testing or onset of chorea after study entry. The gene-positive group demonstrated a significant 3.1% loss of glucose metabolic rate per year in the caudate nucleus (95% confidence interval [CI], −4.64, −1.48) compared with the gene-negative group. There was a 3.6% per year increase in the magnetic resonance imaging bicaudate ratio (95% CI, 1.81, 5.37), a linear measure of caudate atrophy. However, the rate of change in caudate size did not correlate with the rate of change in caudate metabolism, suggesting that metabolic loss and atrophy may develop independently. Thus serial positron emission tomographic or magnetic resonance imaging yield rates of loss not too different from those observed in clinical rating scales (approximately 5% per year, vide supra), and thus may be useful means by which to monitor experimental pharmacologic interventions in presymptomatic individuals at risk for HD should clinical trials be designed to incorporate such a patient population.

In addition to glucose metabolic mapping, other radioligands may be used to monitor striatal integrity in HD. For example, since intrinsic striatal neurons which are lost in HD uniformly bear dopamine receptors, ligands for the dopamine receptor have been used to monitor the progression of HD. These studies do indeed show a parallel reduction of both striatal D1 and D2 receptors in HD patients (Turjanski et al., 1995, Brain 118:689–696).

Similar metabolic and neurochemical findings have been obtained in PET studies of primates treated with quinolinic acid in the striatum. Brownell et al., (1994, Exp. Neurol. 125:41–51), reported that, following a quinolinate lesion of the striata of 3 non-human primates, symptoms similar to those of Huntington's disease could be induced by dopamine agonist treatment. All animals showed a long-term 40–50% decrease in glucose utilization in the caudate by [19F]fluoro-2-deoxy-D-glucose positron emission tomography (PET). Caudate-putamen uptake rate constants for D1 receptors reflected neuronal loss and decreased by an average 40 to 48%. Dopamine reuptake sites and fibers assessed by PET showed a temporary decrease in areas with mild neuronal loss and a long-term decrease in striatal regions with severe destruction. These results, which were consistent with behavioral changes and neuropathology seen at postmortem examination, are similar to those observed in clinical studies of Huntington's disease patients, and serve to additionally validate the quinolinic acid model, and suggest that these measures may be of use in human clinical trials.

Clinical trials in HD have largely been limited to the assessment of palliative symptomatic therapies for psychiatric symptoms and involuntary movements (Shoulson et al., 1981, Neurology 29:1–3). However, there has been one attempt to examine a potential neuroprotective agent. This trial involved the use of baclofen, a GABA-B receptor antagonist, on the theory that this agent would reduce glutamate release from corticostriatal terminals in the striatum, thereby retarding the progression of HD (Shoulson et al., 1989, Quantification of Neurologic Deficit, T L Munsat (ed) Butterworths 271–284). The outcome of this trial was negative, in that baclofen-treated patients fared no better than controls over the 30-month duration of the trial. Nonetheless, this trial provided the proving ground for the use and validation of the HDFC. One important outcome of the study was that the intrinsic rate of disease progression in the study subjects was only one-half of that originally estimated by the investigators. This information may now be used in the design of future clinical trials using this rating instrument.

Currently, there are no major ongoing clinical trials in HD. However, a clinical trials organization, the Huntington's disease Study Group, has been organized and has the infrastructure in place for the conduct of clinical trials in HD. This group is currently investigating a variety of clinical trial options including 1) the use of Coenzyme Q to enhance intermediary metabolism and 2) the use of glutamate antagonists and/or glutamate release blockers (W. Koroshetz, personal communication). A parallel group has been established in Europe, and this group will be using PET methodology to examine the potential efficacy of fetal striatal implants and, eventually, the use of xenograft transplants as well.

The availability of a validated clinical rating instrument, and the existence of correlative radiographic measures to assess disease progression in HD, combined with the existence of 2 large, organized multicenter clinical trials consortia will make implementation of clinical trials in HD straightforward.

Applicants describe herein the production of a modified CNTF molecule, known as Ax-13 or Ax-1, (designated rHCNTF,17CA63QRΔC13) (SEQ ID NO:24) which combines a 63QR substitution (which confers greater biological potency) with a deletion of the terminal 13 amino acid residues (which confers greater solubility under physiological conditions) and a 17CA substitution (which confers stability, particularly under physiological conditions at 37° C.) and shows a 2–3 fold better therapeutic index than rHCNTF in an animal model. However, when expressed in *E. coli*, a substantial portion of the expressed protein produced is tagged with a decapeptide at the C-terminus. Because of this, purification of Ax-13 is difficult and results in a low yield of purified, untagged product. This decapeptide tagging likely does not occur when the Ax-13 is expressed in a mammalian expression system. In addition, it is possible that the decapeptide tag could contribute to increased immunogenicity of the molecule and may also possibly cause problems with stability.

However, use of the *E. coli* expression system would be preferable from the standpoint of cost and efficiency. Therefore, applicants undertook to develop a truncated CNTF molecule that would retain the improved potency, solubility and stability properties of Ax-13 (SEQ ID NO:24), while avoiding the problem of decapeptide tagging when expressed in *E. coli*. As described herein, applicants have succeeded in producing a molecule known as Ax-15, (designated rHCNTF,17CA63QRΔC15) (SEQ ID NO:22), which retains the improved properties of Ax-13, but which also has the added advantage of being expressed by *E. coli* with reduced amino acid tag being added. The new molecule, Ax-15, therefore has the advantage of being more easily purified with a greater yield. Additionally, because there is greatly reduced bacterial amino acid tagging, Ax-15 does not raise the concern with regard to the immunogenicity or stability of the molecule that could be raised by Ax-13.

Therefore the object of the present invention is to provide an improved modified ciliary neurotrophic factor molecule. Specifically, one embodiment of the invention is a modified human ciliary neurotrophic factor having the modification Cys17→Ala, Gln63→Arg, and a deletion of the terminal 15 amino acid residues. The present invention also provides for an isolated nucleic acid molecule encoding the modified human ciliary neurotrophic factor of the invention. Also, contemplated by the invention is a recombinant DNA molecule that encodes the modified human ciliary neurotrophic factor of the invention and which is operatively linked to an expression control sequence, as well as a host cell transformed with the recombinant DNA molecule. The host cell may be prokaryotic or eukaryotic, and therefore may be, for example, a bacterium such as *E. coli*, a yeast cell such as *Pichia pastoris*, an insect cell such as *Spodoptera frugiperda*, or a mammalian cell such as a COS or CHO cell. Said host cell may be used in a method for producing the modified ciliary neurotrophic factor molecule comprising: (a) growing the host cell transformed with the recombinant DNA molecule of the invention so that the DNA molecule is expressed by the host cell to produce the modified ciliary neurotrophic factor molecule of the invention and (b) isolating the expressed, modified ciliary neurotrophic factor molecule.

The subject invention further contemplates a composition comprising the modified ciliary neurotrophic factor molecule of the invention (Ax-15), and a carrier.

Another object of the present invention is to provide a method of treating a disease or disorder of the nervous system comprising administering the modified ciliary neurotrophic factor described herein as Ax-15. The disease or disorder treated may be a degenerative disease and/or involve the spinal cord, motor neurons, cholinergic neurons or cells of the hippocampus. Alternatively, the method of treatment may be for treating a disease or disorder of the nervous system which comprises damage to the nervous system caused by an event selected from the group consisting of trauma, surgery, infarction, infection, malignancy and exposure to a toxic agent. Also contemplated by the present invention is a method of treating a disease or disorder involving muscle atrophy.

A further object of the present invention is to provide a method of protecting striatal neurons from degeneration comprising treating said striatal neurons with an effective amount of the modified ciliary neurotrophic factor described herein as Ax-15.

Also contemplated by the present invention is a method of treating Huntington's disease comprising direct administration to the central nervous system of the modified ciliary neurotrophic factor described herein-as Ax-15.

A further object of the present invention is to provide a method of inducing weight loss in a mammal comprising administration to the mammal of the modified ciliary neurotrophic factor described herein as Ax-15. A specific embodiment of this invention involves inducing weight loss in a human.

The method of administering Ax-15 may be used in the treatment of morbid obesity or obesity of a genetically determined origin. The Ax-15 described herein may also be used in a method of preventing and/or treating the occurrence of gestational or adult onset diabetes in a human.

Any of the above-described methods involving the administration of Ax-15 may be practiced by administering the Ax-15 via a route of delivery selected from the group consisting of intravenous, intramuscular, subcutaneous, intrathecal, intracerebroventricular and intraparenchymal.

Alternatively, the Ax-15 may be administered via the implantation of cells that release the modified ciliary neurotrophic factor.

The present invention also contemplates diseases or disorders resulting from damage to the nervous system, wherein such damage may be caused by trauma, surgery, infarction, infection and malignancy or by exposure to a toxic agent.

The present invention also provides for pharmaceutical compositions comprising a modified CNTF molecule or hybrid or mutant thereof, as described herein, as the sole therapeutic agent or in a complex with the CNTF receptor, in a suitable pharmacologic carrier.

The active ingredient, which may comprise CNTF or the modified CNTF molecules described herein should be formulated in a suitable pharmaceutical carrier for administration in vivo by any appropriate route including, but not limited to intraparenchymal, intraventricular or intracerebroventricular delivery, or by a sustained release implant, including a cellular or tissue implant such as is described, for example, in published application WO96/02646 published on Feb. 1, 1996, WO95/28166 published on Oct. 26, 1995, or WO95/505452 published Feb. 23, 1995.

Depending upon the mode of administration, the active ingredient may be formulated in a liquid carrier such as saline, incorporated into liposomes, microcapsules, polymer or wax-based and controlled release preparations, In preferred embodiments, modified CNTF preparations which are stable, or formulated into tablet, pill or capsule forms.

The concentration of the active ingredient used in the formulation will depend upon the effective dose required and the mode of administration used. The dose used should be sufficient to achieve circulating plasma concentrations of active ingredient that are efficacious. Effective doses may be extrapolated from dose-response curves derived from in vitro or animal model test systems. Effective doses are expected to be within the range of from about 0.001 to about 1 mg/day.

EXAMPLES

Example 1

Electrophoretic Mobility of Modified Human CNTF Molecules

Materials and Methods

Preparation of Modified CNTF Molecules
  Bacterial Strains and Plasmids
  E. coli K-12 RFJ26 is a strain that overproduces the lactose operon repressor.

The expression vectors pRPN33, which carries the human CNTF gene and pRPN110 which carries the rat CNTF gene are nearly identical (Masiakowski, et al., 1991, J. Neurosci. 57:1003–1012 and in International Publication No. WO 91/04316, published on Apr. 4, 1991.)

Plasmid pRPN219 was constructed by first digesting pRPN33 with the restriction enzymes Nhe1 plus Hind3 and gel purifying the 4,081 bp fragment. The second, much smaller fragment which codes for part of the human CNTF gene was subsequently replaced with an 167 bp Nhe1 Hind3 fragment that was obtained by PCR amplification from the rat gene using the primers RAT-III-dniH: 5' ACGGTAAGCT TGGAGGTTCTC 3' (SEQ ID NO: 16); and RAT-Nhe-I-M: 5' TCTATCTGGC TAGCAAGGAA GATTCGTTCA GAC-CTGACTG CTCTTACG 3' (SEQ ID NO: 17).

Plasmid pRPN228 was constructed in the same manner as pRPN219, except that the 167 bp replacement fragment was amplified using the DNA primers Rat-III-dniH-L-R: 5' AAG GTA CGA TAA GCT TGG AGG TTC TCT TGG AGT CGC TCT GCC TCA GTC AGC TCA CTC CAA CGA TCA GTG 3' (SEQ ID NO: 18) and Rat-Nhe-1:5' TCT ATC TGG CTA GCA AGG AAG 3' (SEQ ID NO: 19).

Plasmids pRPN186, pRPN187, pRPN188, pRPN189, pRPN192, pRPN218, and pRPN222 were generated by similar means or by direct exchange of DNA fragments using the unique restriction sites shown in FIG. 1 (SEQ ID NOS 6–15).

The identity of all plasmids was confirmed by restriction analysis and DNA sequencing.

Protein Purification

Induction of protein synthesis, selective extraction, and purification from inclusion bodies were as described for rat and human CNTF (Masiakowski, et al., 1991, J. Neurosci. 57:1003–1012 and in International Publication No. WO 91/04316, published on Apr. 4, 1991) except that gel filtration was occasionally used instead or in addition to ion exchange chromatography. Alternatively, proteins were purified from the supernatants of cell lysates by streptomycin and ammonium sulfate fractionation, followed by column chromatography, as described for other proteins (Panayotatos et al., 1989, J. Biol. Chem. 264:15066–15069). All proteins were isolated to at least 60% purity.

Conditions for enzymatic reactions, DNA electrophoresis and other techniques used in these studies have been described in detail (Panayotatos, N. 1987, Engineering an Efficient Expression System in Plasmids: A practical Approach (Hardy, K. G. ed.) pp 163–176, IRL Press, Oxford, U.K.).

Results

Figure 2:
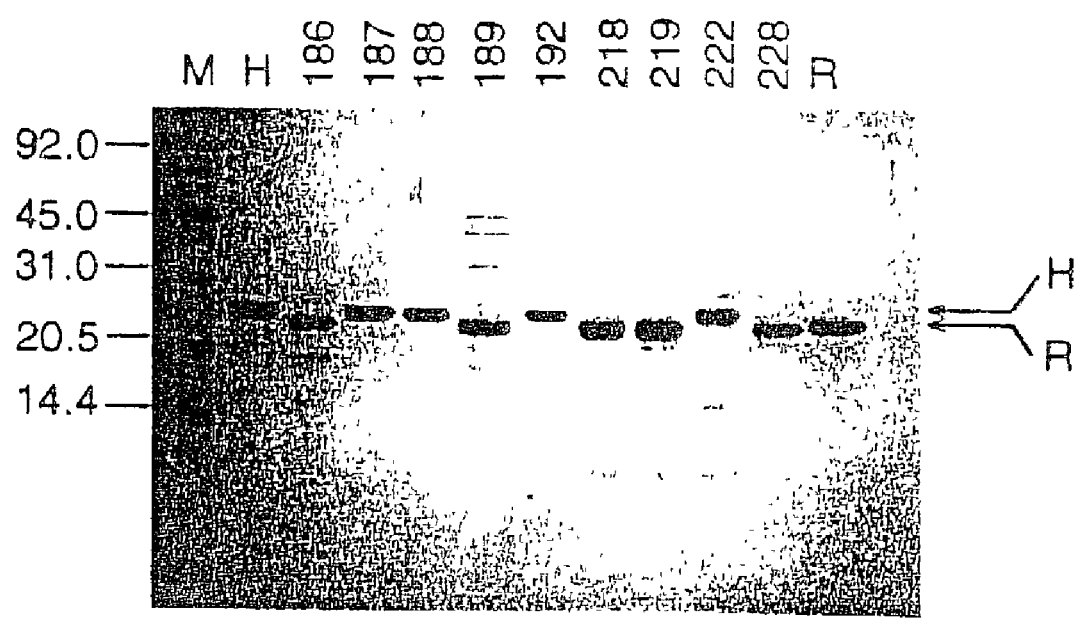
FIG. 2—Mobility of human, rat and several modified CNTF molecules on reducing SDS-15% polyacrylamide gels. Purified recombinant proteins were loaded as indicated. Markers of the indicated MW were loaded on lane M.

The mobilities of human, rat and several chimeric CNTF molecules on reducing SDS-polyacrylamide gels are shown in FIG. 2. The chimeric molecules RPN186, RPN189, RPN218 and RPN228 exhibit mobilities comparable to rat CNTF, whereas RPN187, RPN188, RPN192 and RPN222 exhibit mobilities comparable to human CNTF. Cross-reference of these results to the aligned sequences of these proteins in FIG. 1 (SEQ ID NOS: 6–15) reveals that all proteins carrying an arginine residue at position 63 (R63) display the mobility of rat CNTF. In the case of RPN228, this single amino acid substitution (Q63-→R) is sufficient to confer to human CNTF the normal mobility of rat CNTF.

FIG. 2 also provides a measure of the purity of the different recombinant proteins. By visual inspection, purity varies from 60% for RPN189 to better than 90% for RPN228.

Example 2

Measurement of Binding Activity of Modified CNTF Molecules

Materials and Methods
  Preparation of 125I-CNTF

Recombinant rat CNTF (28 µg) in 37 µl 0.2 M sodium borate buffer, pH 8.5 was transferred to a vial containing 4 mCi, (2,000 Ci/mmole; NEN) of $^{125}$I and reagent (Bolton and Hunter, 1973, Biochem J. 133: 529–539) which had been dried under a gentle stream of nitrogen. Reactions were incubated for 45 min at 0° C. followed by 15 min at room temperature and terminated by the addition of 30 ml of 0.2 M glycine solution. After 15 min, 0.2 ml PBS containing 0.08% gelatin was also added and the mixture was passed through a Superdex-75 column (Pharmacia) to separate the labelled monomeric CNTF from dimeric and other multimeric derivatives. Percentage of incorporation was typically 20%, as determined by thin layer chromatography and the specific activity was typically around 1,000 Ci/mmole. The monomeric $^{125}$I-CNTF was stored at 4° C. and used up to one week after preparation. As a test of structural and conformational integrity, $^{125}$I-CNTF (approximately 10,000 cpm) was mixed with a 5 µg unlabelled CNTF and analyzed by native gel electrophoresis. One major band was visible by either Coomassie staining or autoradiography. $^{125}$I-CNTF also showed comparable activity to native CNTF in supporting survival of E8 chick ciliary neurons in culture.

Tissue Culture Techniques

Superior cervical ganglia (SCG) from neonatal rats were treated with trypsin (0.1%), mechanically dissociated and plated on a poly-ornithine (30 µg/ml) substratum. Growth medium consisted of Ham's nutrient mixture F12 with 10% heat-inactivated fetal bovine serum (Hyclone), nerve growth factor (NGF) (100 ng/ml), penicillin (50 U/ml) and streptomycin (50 µg/ml). Cultures were maintained at 37° C. in a humidified 95% air/5% $CO_2$ atmosphere. Ganglion non-neuronal cells were eliminated by treatment with araC (10 µM) on days 1 and 3 of culture. Cultures were fed 3 times/week and were routinely used for binding assays within 2 weeks.

MG87/CNTFR is a fibroblast cell line transfected with the human CNTFα receptor gene (Squinto, et al., 1990, Neuron 5:757–766; Davis et al., 1991, Science 253:59–63).

Binding Assays

Binding was performed directly on cell monolayers. Cells in culture wells were washed once with assay buffer consisting of phosphate buffered saline (PBS; pH 7.4), 0.1 mM bacitracin, 1 mM PMSF, 1 µg/ml leupeptin, and 1 mg/ml BSA. After incubation with $^{125}$I-CNTF for 2 hours at room temperature, cells were quickly washed twice with assay buffer, lysed with PBS containing 1% SDS and counted in a Packard Gamma Counter. Non-specific binding was determined in the presence of 1,000-fold excess of unlabelled CNTF. Specific binding towards MG87/CNTFR was 80–90%. Data were analyzed using the GRAPHPAD program (ISI, Philadelphia, Pa.).

Results

Figure 4A:
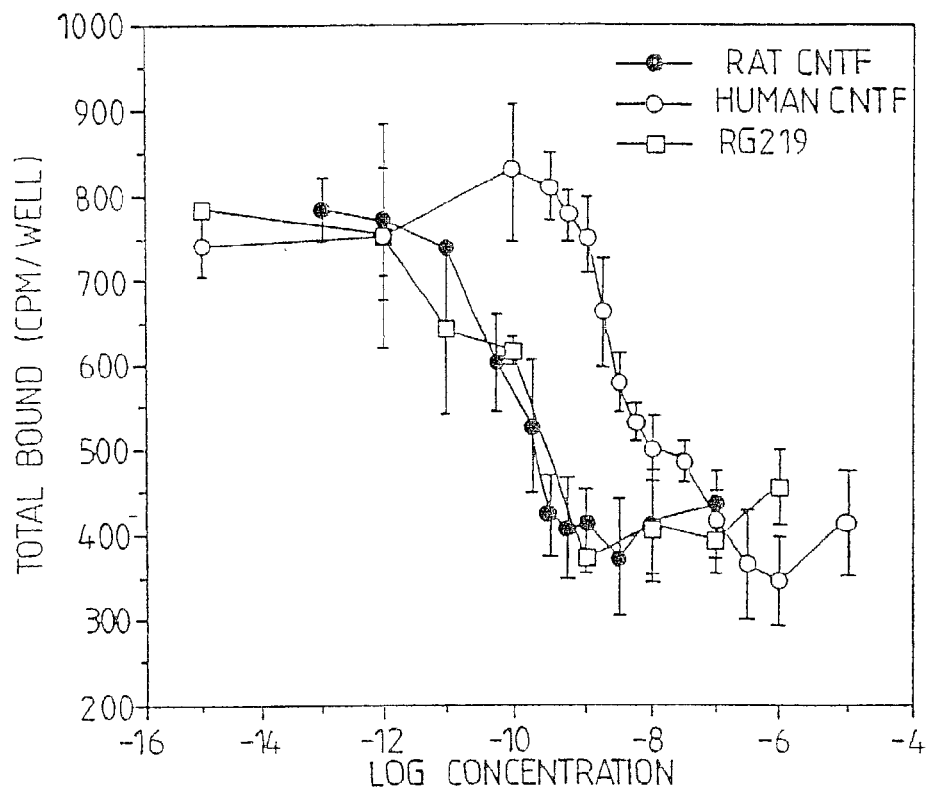
FIG. 4—Competitive ligand binding towards A.) SCG neurons and B.) MG87/huCNTFR fibroblasts. Standard deviation from the mean of three determinations is shown by vertical bars.

Competition curves of purified recombinant human, rat and CNTF RPN219 towards $^{125}$I-rat CNTF for binding on rat SCG neurons are shown in FIG. 4a. Both rat and human CNTF compete with $^{125}$I-rat CNTF for binding to SCG neurons, but human CNTF (IC50=25 nM) is 90 times less potent in displacing $^{125}$I-rat CNTF binding than unlabelled rat CNTF (IC50=0.28 nM). In contrast, RPN219 is almost as potent as rat CNTF and clearly more potent than human CNTF (IC50=0.3 nM).

Figure 4B:
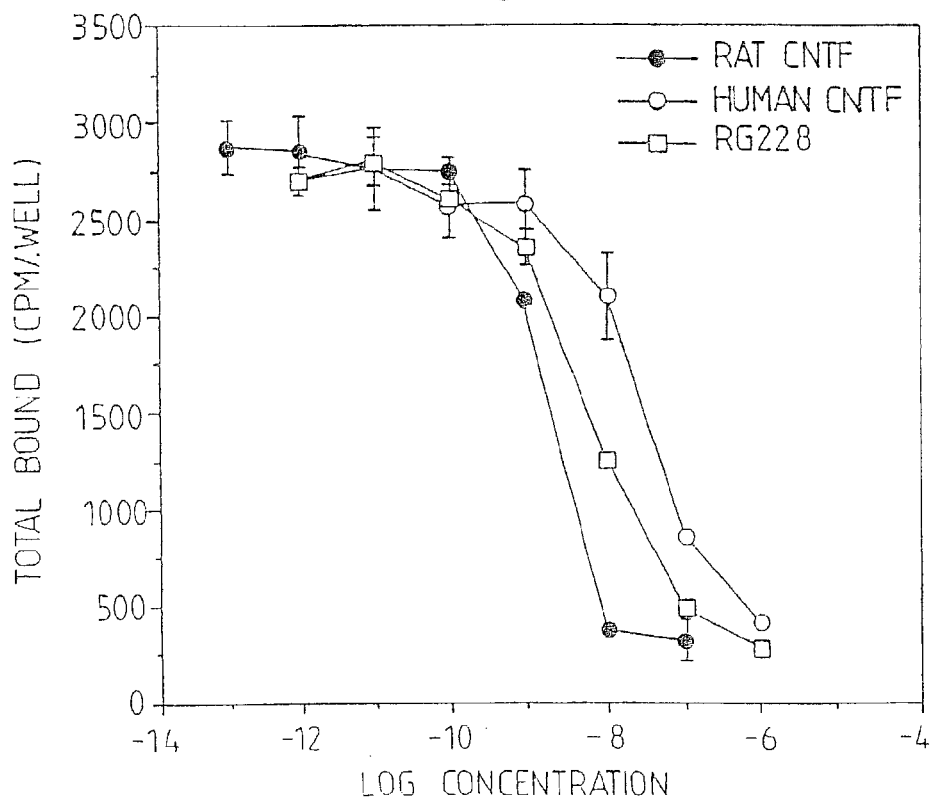

Similar results were obtained from competition experiments with mouse fibroblasts transfected with a plasmid directing the expression of the human CNTF receptor (FIG. 4b). Both rat, human and RPN228 compete with $^{125}$I-rat CNTF for binding to MG87/CNTFR cells. Human CNTF (IC50=30 nM) is 12 times less potent than rat CNTF (IC50=2.8 nM), whereas RPN228 is clearly more potent than the human protein (IC50=5.6 nM).

Competition binding experiments with the other modified CNTF proteins shown in FIG. 1 (SEQ ID NOS: 6–15) also demonstrated that proteins having R63 displayed the biological activity of rat CNTF, whereas proteins having Q63 displayed the binding properties of human CNTF (data not shown). These results indicate that the single amino acid substitution (Q63-→R) is sufficient to confer to human CNTF the receptor binding properties characteristic of rat CNTF.

Example 3

Measurement of Biological activity of Modified CNTF Molecules

Materials and Methods

Recombinant CNTF was assayed on dissociated cultures of chick ciliary ganglion (CG) neurons as described (Masiakowski, et al., 1991, J. Neurosci. 57:1003–1012 and in International Publication No. WO 91/04316, published on Apr. 4, 1991), except that surviving cells were stained with MTT (Mosmann, T. 1983; J. Immunol. Methods 65:55–63).

Results

Figure 3A:
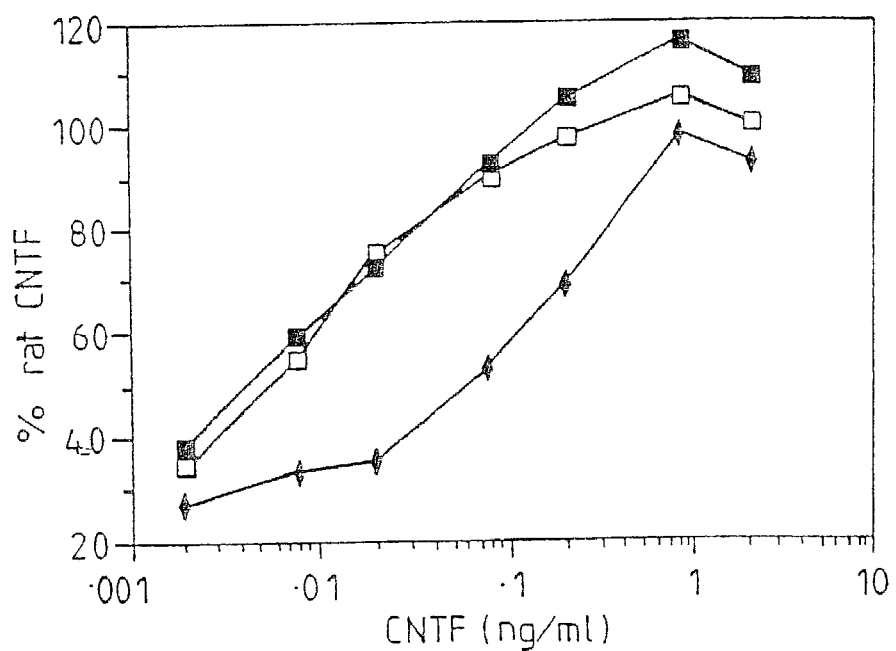
FIG. 3—Biological activity of two modified CNTF molecules. A. human CNTF (filled diamonds), rat CNTF (open squares), and RPN219 (filled squares). B. human CNTF (filled diamonds), rat CNTF (open squares), and RPN228 (filled squares). Dose response of dissociated E8 chick ciliary neurons surviving at the indicated protein concentration, as a percentage of the number of neurons surviving in the presence of 2 ng/ml rat CNTF. Each experimental point represents the mean of three determinations.
Figure 3B:
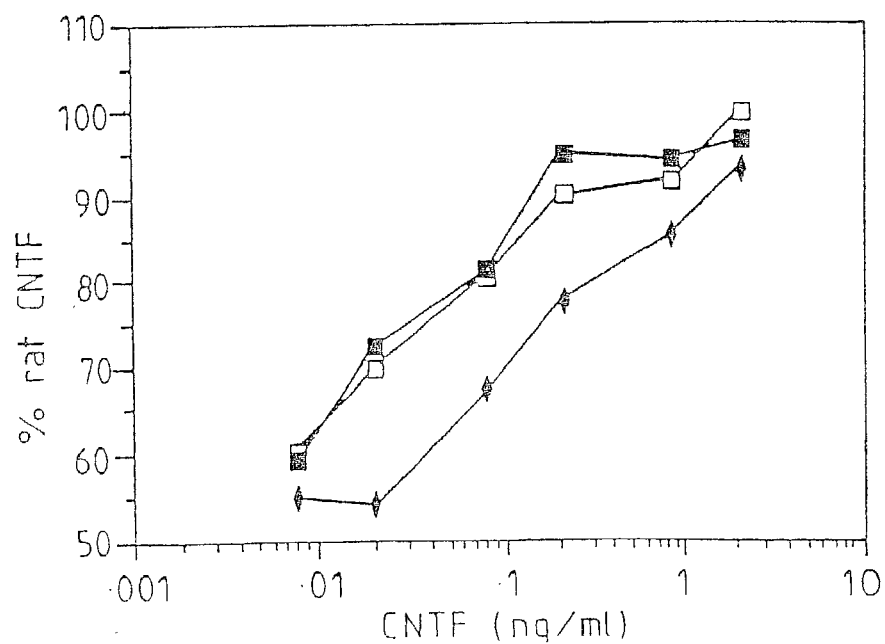

FIG. 3 shows dose-response curves of dissociated, neuron enriched cultures of E8 chick embryo ciliary ganglia for purified recombinant human, rat and the modified CNTF proteins RPN219 and RPN228. By this assay, the biological activity of the chimeric proteins is indistinguishable from that of purified recombinant rat CNTF and clearly higher than that of recombinant human CNTF. Comparison of the dose response curves in FIG. 3 also shows that the maximal levels of surviving neurons obtained with RPN219, RPN228 or rat CNTF are higher than those obtained with human CNTF. These results suggest that RPN219 and RPN228, like rat CNTF, are active towards a larger population of neurons than human CNTF. In parallel experiments, the biological activity of the other modified CNTF proteins shown in FIG. 1 (SEQ ID NOS: 6–15) was examined. In every case, modified CNTF proteins carrying the (Q63æR) substitution displayed the biological activity of rat CNTF whereas proteins having Q63 displayed the activity of human CNTF (data not shown).

Overall, these results indicate that the single amino acid substitution (Q63→R) is sufficient to confer to human CNTF the biological activity of rat CNTF.

Example 4

Use of Modified CNTF to Prevent Light Induced Photoreceptor Injury

Albino rats of either the F344 or Sprague-Dawley strain were used at 2–5 months of age. The rats were maintained in a cyclic light environment (12 hr on: 12 hr off at an in-cage illuminance of less than 25 ft-c) for 9 or more days before being exposed to constant light. The rats were exposed to 1 or 2 weeks of constant light at an illuminance level of 115–200 ft-c (most rats received 125–170 ft-c) provided by two 40 watt General Electric "cool-white" fluorescent bulbs with a white reflector that was suspended 60 cm above the floor of the cage. During light exposure, rats were maintained in transparent polycarbonate cages with stainless steel wire-bar covers.

Two days before constant light exposure, rats anesthetized with a ketamine-xylazine mixture were injected intravitreally with 1 µl of rat CNTF, human CNTF or modified CNTF [hCNTF (Q63→R)] dissolved in phosphate buffered saline (PBS) at a concentration of 0.1 to 500 ng/µl. The injections were made with the insertion of a 32 gauge needle through the sclera, choroid and retina approximately midway between the ora serrata and equator of the eye. In all cases, the injections were made into the superior hemisphere of the eye.

Immediately following constant light exposure, the rats were sacrificed by overdose of carbon dioxide followed immediately by vascular perfusion of mixed aldehydes. The eyes were embedded in epoxy resin for sectioning at 1 µm thickness to provide sections of the entire retina along the vertical meridian of the eye. The degree of light-induced retinal degeneration was quantified by assessing the degree of photoreceptor rescue by a 0–4+ pathologist's scale of rescue, 4+ being maximal rescue and almost normal retinal integrity. The degree of photoreceptor rescue in each section, as based on comparison to the control eye in the same rat, was scored by four individuals. This method has the advantage of considering not only the ONL thickness, but also more subtle degenerative changes to the photoreceptor inner and outer segments, as well as spatial degenerative gradients within the eye. Three eyes were examined for each time point to generate a dose response curve.

Results

The degree of rescue was measured for human, rat and hCNTF (Q63→R). The data indicated that both rat and hCNTF (Q63→R) had ten-fold greater ability to rescue photoreceptors in the light damage model than did recombinant human CNTF.

It is to be understood that while the invention has been described above in conjunction with preferred specific embodiments, the description and examples are intended to illustrate and not limit the scope of the invention, which is defined by the scope of the appended claims.

Example 5

Materials and Methods

Recombinant human CNTF variants were genetically engineered, expressed in E. coli and recovered at greater than 90% purity, as described previously (Masiakowski, et al., 1991, J. Neurosci. 57:1003–1012 and in International Publication No. WO 91/04316, published on Apr. 4, 1991; Panayotatos et al., 1993, J. Biol. Chem. 268:19000–19003).

The following stock solutions were prepared freshly in PBS at 5° C.:

| | |
|---|---|
| rHCNTF | 0.5 mg/ml |
| RG160 (rHCNTF, ΔC13) | 0.5 mg/ml |
| RG162 (rHCNTF, 17CA, ΔC13) | 0.5 mg/ml |
| RG290 (rHCNTF, 63QR, ΔC13) | 1.2 mg/ml |
| RG297 (rHCNTF, 17CA, 63QR, ΔC13) | 0.4 mg/ml |

To determine the stability of rHCNTF and several derivatives in physiological buffer at 37° C., stock solutions were dialyzed exhaustively against PBS at 5° C., diluted with PBS to 0.1 mg/ml and sterilized by filtration. Aliquots (0.2 ml), were transferred into 0.5 ml capacity polypropylene centrifugation tubes. The tubes were placed in a 37° C. incubator and, at the indicated times, individual tubes were removed and centrifuged at 15,000 rpm for 3 min at room temperature to separate soluble protein from insoluble precipitates. Supernatants were pipetted off into clean tubes containing an equal volume of 2× protein gel sample buffer, placed in a 85° C. bath for 2 min, mixed and stored at −20° C. until analysis by 15% SDS-PAGE. Pellets were resuspended in 1/10 original volume of water, mixed with an equal volume of 2× protein gel sample buffer and treated as above.

Methods for biological activity assays on E8 chick ciliary neurons and for protein gel electrophoresis have been described (Masiakowski, et al., 1991, J. Neurosci. 57:1003–1012 and in International Publication No. WO 91/04316, published on Apr. 4, 1991; Panayotatos et al., 1993, J. Biol. Chem. 268:19000–19003). Protein gel sample buffer (2×) consists of 12.5 ml Tris HCl, pH 6.8—20 ml glycerol—40 ml 10% SDS and 5 mg Bromophenol Blue per 100 ml.

Results

The solubility of rHCNTF is particularly limited in physiological buffer at neutral pH. Furthermore, the solubility over a broad pH range (4.5–8.0) depends strongly on the temperature and on the time of incubation. At 5° C., the solubility of rHCNTF in PBS is 1.4 mg/ml and the protein remains in solution for a few hours. In sharp contrast to the limited solubility of rHCNTF, the variant rHCNTF,ΔC13 can be concentrated to at least 12 mg/ml at 5° C. Despite this greater solubility, however, rHCNTF,ΔC13 still shows strong instability in physiological buffer, pH and temperature conditions. Upon incubation at 37° C., rHCNTF,ΔC13 falls out of solution at a rate that depends on the initial concentration.

Figure 5A:
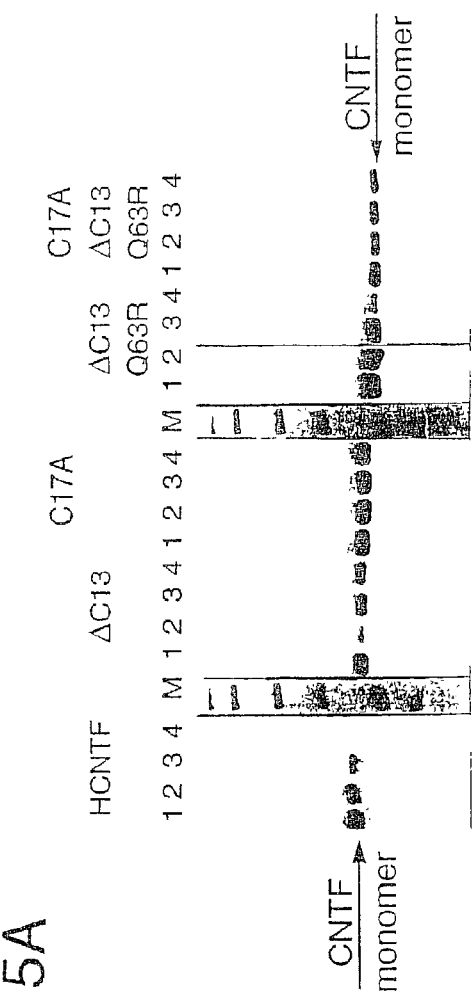
FIG. 5—Mobility of human and several modified CNTF molecules on SDS-15% polyacrylamide gels. Supernatant (A) and pellet (B) preparations of recombinant human CNTF (designated HCNTF) and several modified CNTF proteins were loaded as indicated. The modified proteins shown are ΔC13 (also known as RG160); 17CA,ΔC13 (RG162); ΔC13,63QR (RG290); and 17CA,ΔC13,63QR (RG 297). Markers of the indicated MW were loaded on lane M. Incubation in physiological buffer at 37° C. for 0, 2, 7 and 14 days is indicated in lanes 1–4, respectively.
Figure 5B:
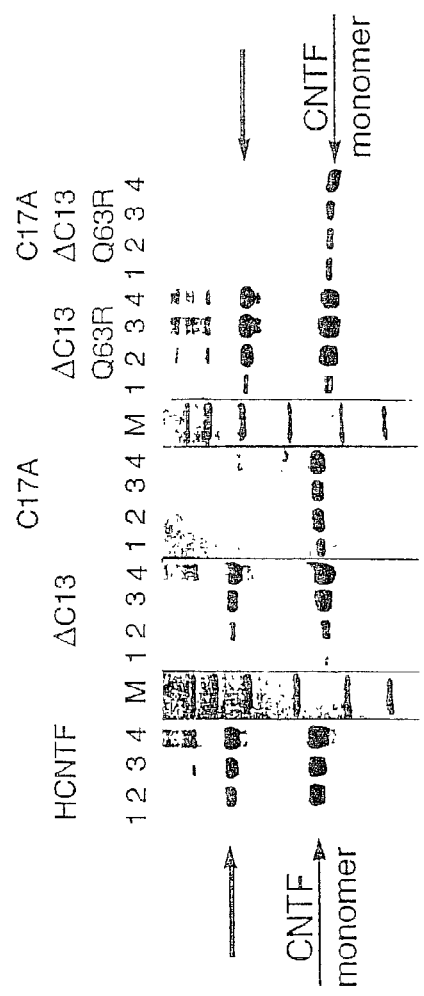

To determine the cause of this instability, we analyzed the physical integrity of rHCNTF and several variants in parallel experiments. FIG. 5 shows that incubation of rHCNTF in physiological buffer at 37° C. for 0, 2, 7 and 14 days (lanes 1–4, respectively) caused progressive disappearance of the protein from the supernatants, accompanied by concomitant progressive appearance in the pellets. Furthermore, a good proportion of rHCNTF in the pellets appeared as a 48 kD species that corresponded to the size of dimeric rHCNTF (FIG. 5, double arrow). At longer incubation times, a small proportion of higher order aggregates was also evident. However, when the same samples were analyzed on the same type of gel but in the presence of disulfide reducing agents, the 48 kD species was converted to monomeric rHCNTF, evidence that the 48 kD species represents rHCNTF dimers covalently linked by disulfide bonds. Such dimers would be expected to form through the unique cysteine residue of rHCNTF. Therefore, these results indicated that the instability of rHCNTF at 37° C. is caused by aggregation initiated by intermolecular disulfide bond formation.

Similar results were obtained with two rHCNTF variants, rHCNTF,ΔC13 and rHCNTF,63QR,ΔC13, except that the appearance of insoluble aggregates in the pellets was somehow slower in the case of rHCNTF,ΔC13 (FIG. 5). Given the fact that the ΔC13 deletion confers to rHCNTF much greater solubility in physiological buffer, the improved stability of rHCNTF,ΔC13 is most likely an indirect consequence of its greater solubility.

To further test the possibility that the instability of rHCNTF at 37° C. is caused by aggregation initiated by intermolecular disulfide bond formation, the unique cysteine residue at position 17 was substituted by alanine, using established genetic engineering methodology. The two rHCNTF variants, rHCNTF,17CA, ΔC13 (SEQ ID NO:27), and rHCNTF,17CA,63QR, ΔC13 (SEQ ID NO:24), generated by this process were subjected to the same analysis by non reducing 15% SDS-PAGE. FIG. 5 shows that even after incubation for 14 days at 37° C. both proteins remained soluble with no evidence of dimerization or aggregate formation. Even in the small proportion of protein found in the pellets, which represented mostly the small amount of soluble protein remaining in the centrifuge tubes after removal of the supernatant, there was little evidence of dimerization. These results confirmed the conclusion that the instability of rHCNTF is caused by aggregation initiated by intermolecular disulfide bond formation, and demonstrated that elimination of the free -SH functional group in other rHCNTF variants, e.g. RG297, also result in greater stability.

Figure 6:
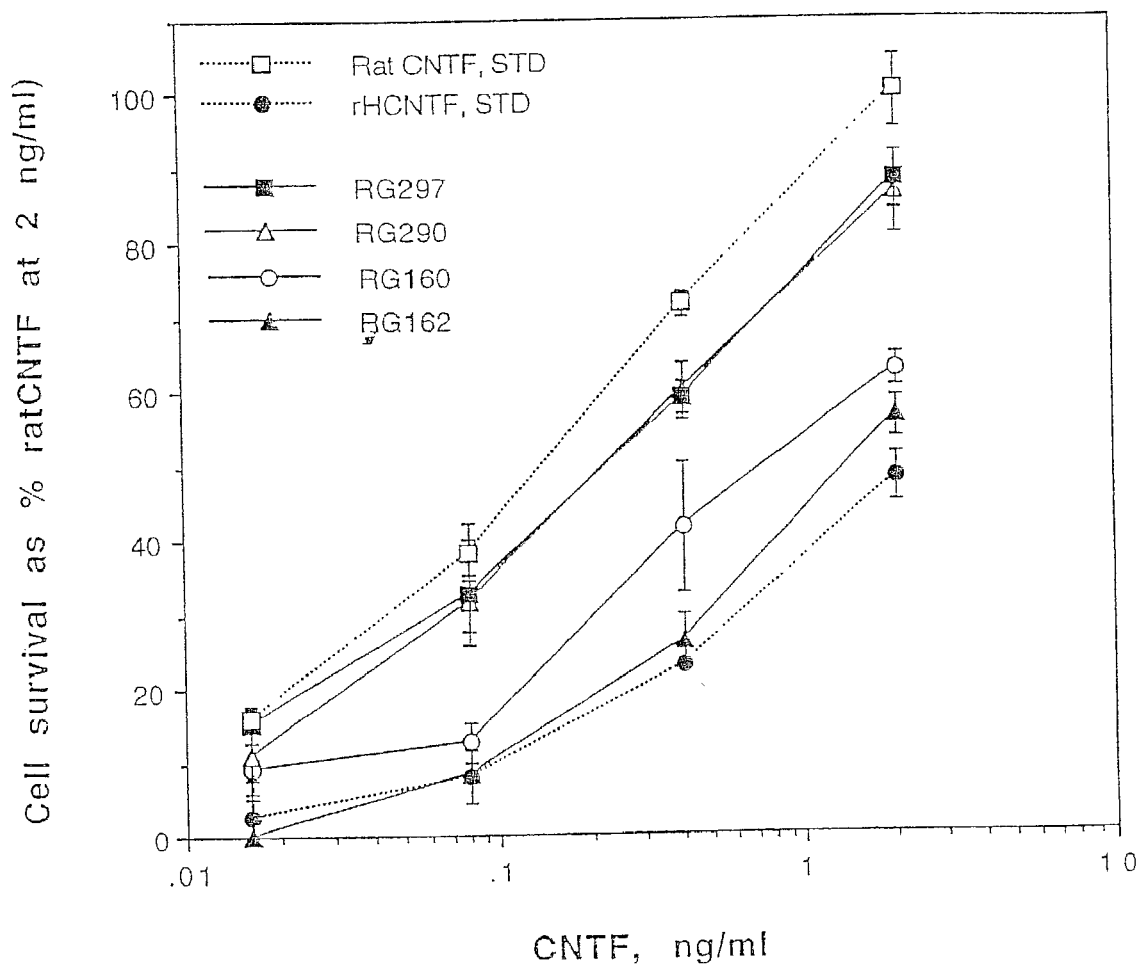
FIG. 6—Survival of primary dissociated E8 chick ciliary neurons in response to increasing concentrations of various CNTF variants. Control concentration response curves for rat CNTF and rHCNTF obtained with standard, untreated stock solutions, as well as with four rHCNTF variants, RG297, RG290, RG160 and RG162.
Figure 7:
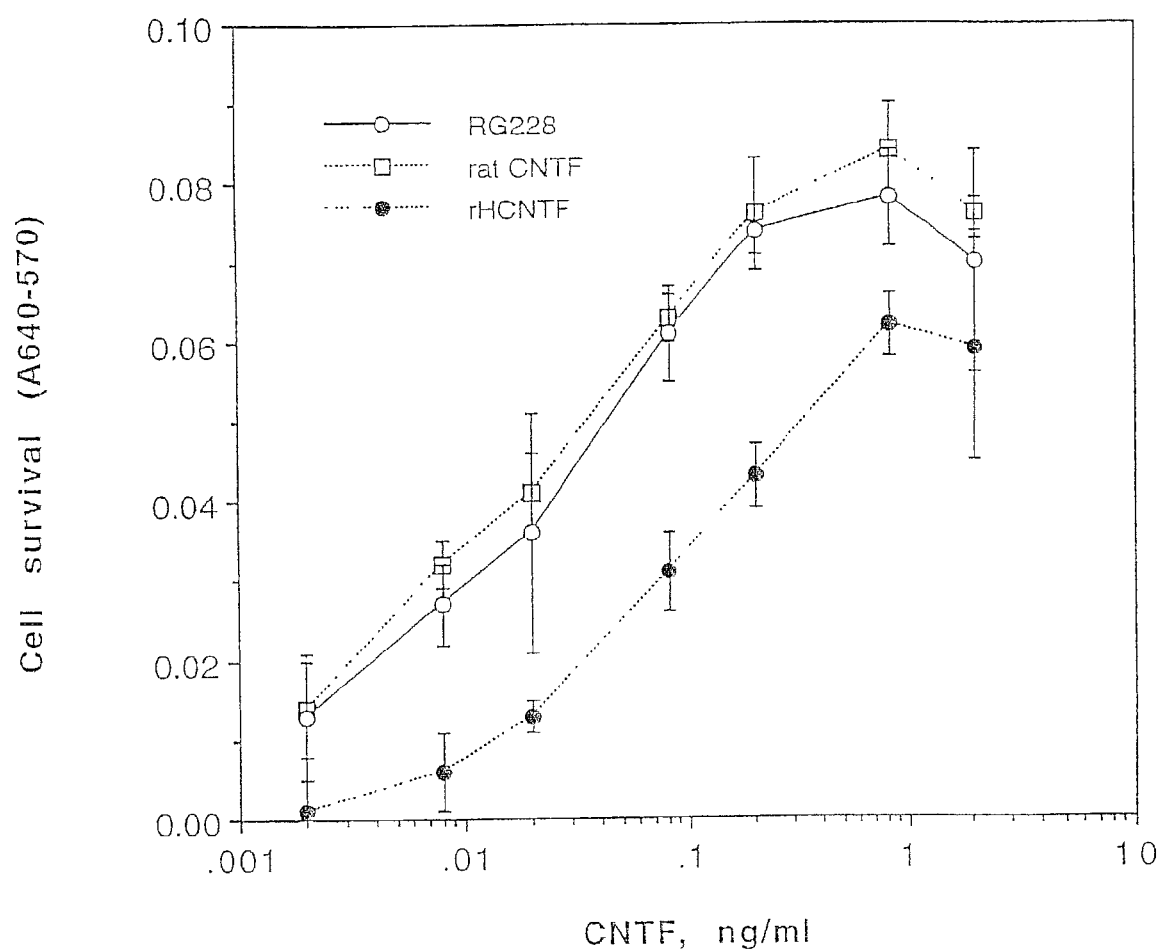
FIG. 7—Survival of primary dissociated E8 chick ciliary neurons in response to increasing concentrations of various CNTF variants. Control concentration response curves for rat CNTF and rHCNTF obtained with standard, untreated stock solutions, as well as with rHCNTF variant RG228 (also known as RPN228 and having the mutation 63QR).

To test whether the proteins remaining in solution after incubation at 37° C. were still biologically active, samples were analyzed for neuronal survival activity. FIG. 6 shows control concentration response curves for rat CNTF and rHCNTF obtained with standard, untreated stock solutions, as well as with four rHCNTF variants incubated for 7 days at 37° C. Of the latter, the proteins carrying the 17CA mutation, RG297 and RG162, were assayed at their nominal concentrations, whereas RG290 and RG160 were assayed after correcting their concentrations for the amount of protein remaining in solution. FIG. 6 shows that the concentration response curves displayed by these compounds are those expected from these proteins in their fully active form: RG160 and RG162 show the same potency as rHCNTF within experimental error, whereas RG290 and RG297 that carry the 63QR substitution show 4–5 fold higher potency than rHCNTF, as previously observed (Panayotatos, N., et al., 1993, J. Biol. Chem. 268:19000–19003) and as shown in FIG. 7. Therefore, incubation of rHCNTF and its derivatives at 37° C. for 7 days does not cause loss of biological activity, only loss of protein through dimerization followed by precipitation.

Example 6

Materials and Methods

Protein Engineering and Purification—The following rHCNTF variants were compared to rHCNTF:
RG228 (rHCNTF,63QR);
RG297 (rHCNTF,17CA,63QR, ΔC13)
RG242 (rHCNTF,63QR64WA)

These proteins were genetically engineered, expressed in E. coli and recovered at greater than 90% purity by the methodology described for rHCNTF (Masiakowski, et al., 1991, J. Neurosci. 57:1003–1012 and in International Publication No. WO 91/04316, published on Apr. 4, 1991; Panayotatos et al., 1993, J. Biol. Chem. 268:19000–19003).

Biological Activity Assays—Methods for biological activity assays on E8 chick ciliary neurons have been described (Panayotatos et al., 1993, J. Biol. Chem. 268: 19000–19003).

Pharmacokinetic Determinations—Rats were injected intravenously (i.v.) with rHCNTF (n=1) and RG242 (n=2) at 100 μg/kg and with RG228 (n=1) at 200 μg/kg. Rats were also injected subcutaneously (s.c.) with rHCNTF (n=2), RG242 (n=2) and RG228 (n=1) at 200 μg/kg. Blood specimens were collected prior to dosing and at various times after dosing and were processed to obtain plasma. The plasma specimens were analyzed using the rHCNTF ELISA method for rodent plasma (D. B. Lakings, et al. DSER 93/DMAP/006, "Dose Proportionality and Absolute Bioavailability of rHCNTF in the Rat Following Subcutaneous Administration at Eight Dose Levels" (Phoenix International Project No. 920847) 10 Nov. 1993.

The plasma concentrations were evaluated using non compartment techniques. A standard curve for each compound was included on each assay plate and was used to calculate the amount of that compound present in the specimens analyzed on the plate. The sensitivity of the assay varied among compounds by less than twofold.

Efficacy and Toxicity Determinations In Vivo—Male Sprague-Dawley rats weighing ~220 g were anesthetized before surgery. The right sciatic nerve was transected at the level of the knee and a 5 mm segment of nerve was removed. Sham surgeries were performed on the left side of each animal. Starting the morning after surgery, rats were weighed and administered vehicle (either PBS or lactate/phosphate/mannitol, pH 4.5) or the rHCNTF compound to be tested, dissolved in the same vehicle at doses ranging from 0.01–1.0 mg/kg, s.c. Rats were weighed and injected daily for 1 week, at which time they were sacrificed and the soleus muscles dissected and weighed. The ratio of the right (denervated) to left (sham) soleus wet weights for each animal was calculated to assess the degree of atrophy caused by denervation and the prevention thereof by treatment with each compound. For assessment of toxicity, the body weights were calculated as a percent of the weight gain of vehicle-treated rats. Both vehicle solutions produced similar results in atrophy and body weight gain.

Results

Figure 8:
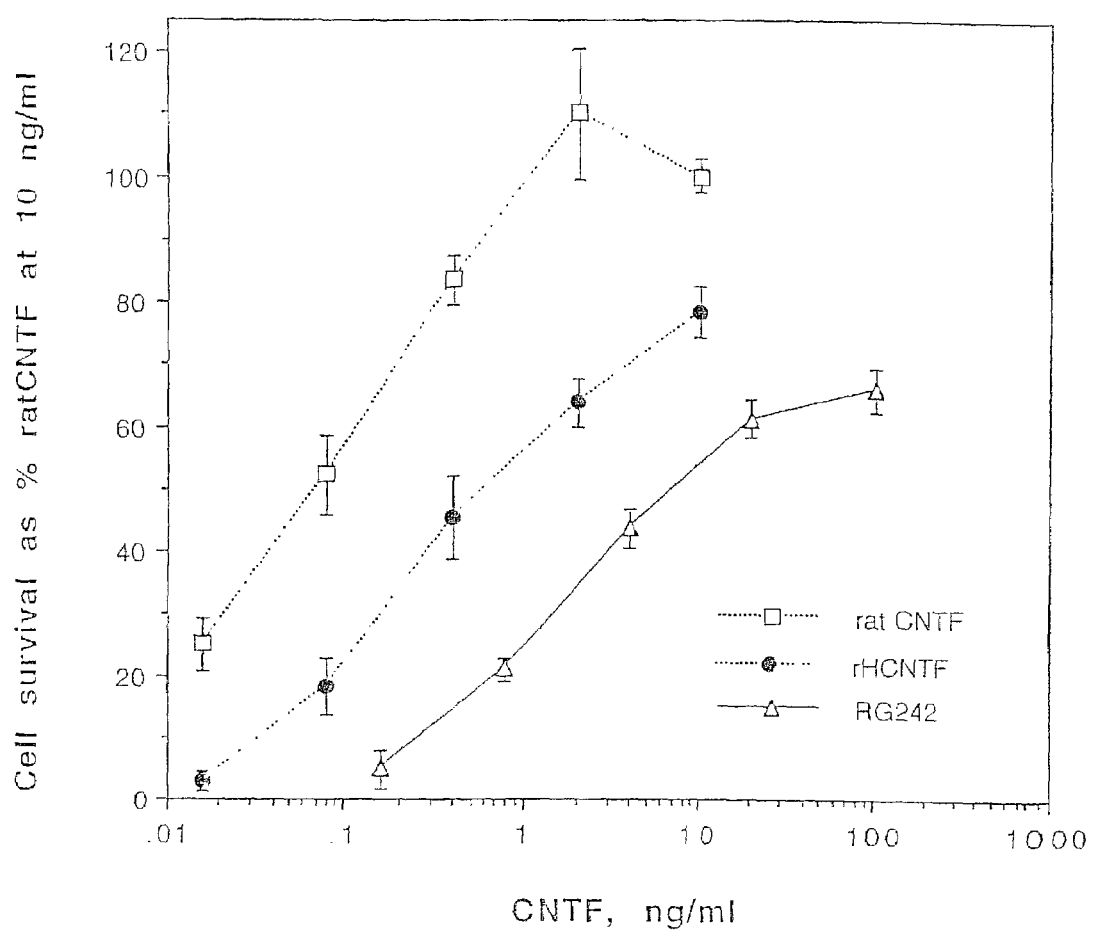
FIG. 8—Survival of primary dissociated E8 chick ciliary neurons in response to increasing concentrations of various CNTF variants. Control concentration response curves for rat CNTF and rHCNTF obtained with standard, untreated stock solutions, as well as with rHCNTF variant RG242 (which has the mutation 63QR,64WA).

Biological Activity In Vitro—To characterize the activity of rHCNTF in vitro, we measured its effect on mediating the survival of primary dissociated E8 chick ciliary neurons. Neuronal survival in response to increasing concentrations of various human CNTF variants is shown in FIGS. 6, 7 and 8. The variants RG228 (FIG. 7) and RG297 (FIG. 8) that carry the 63QR substitution show 4–5 times greater potency than rHCNTF but the variant RG242 showed a 10-fold weaker potency than rHCNTF, despite the fact that it carries the 63QR substitution. Thus, introduction of various amino acid side chains at various positions of the CNTF sequence has very different effects on the survival of primary neurons in vitro that vary from great loss to strong gain of activity relative to rHCNTF.

Pharmacokinetics—Before attempting to correlate the in vitro biological potency of a set of compounds to their pharmacological efficacy in vivo, it is useful to determine their absolute bioavailability in the same animal model. In the experiments described below, the disposition kinetics after i.v. administration and the absolute bioavailability after s.c. administration of RG228 and RG242 were determined and compared to those of rHCNTF.

Figure 9:
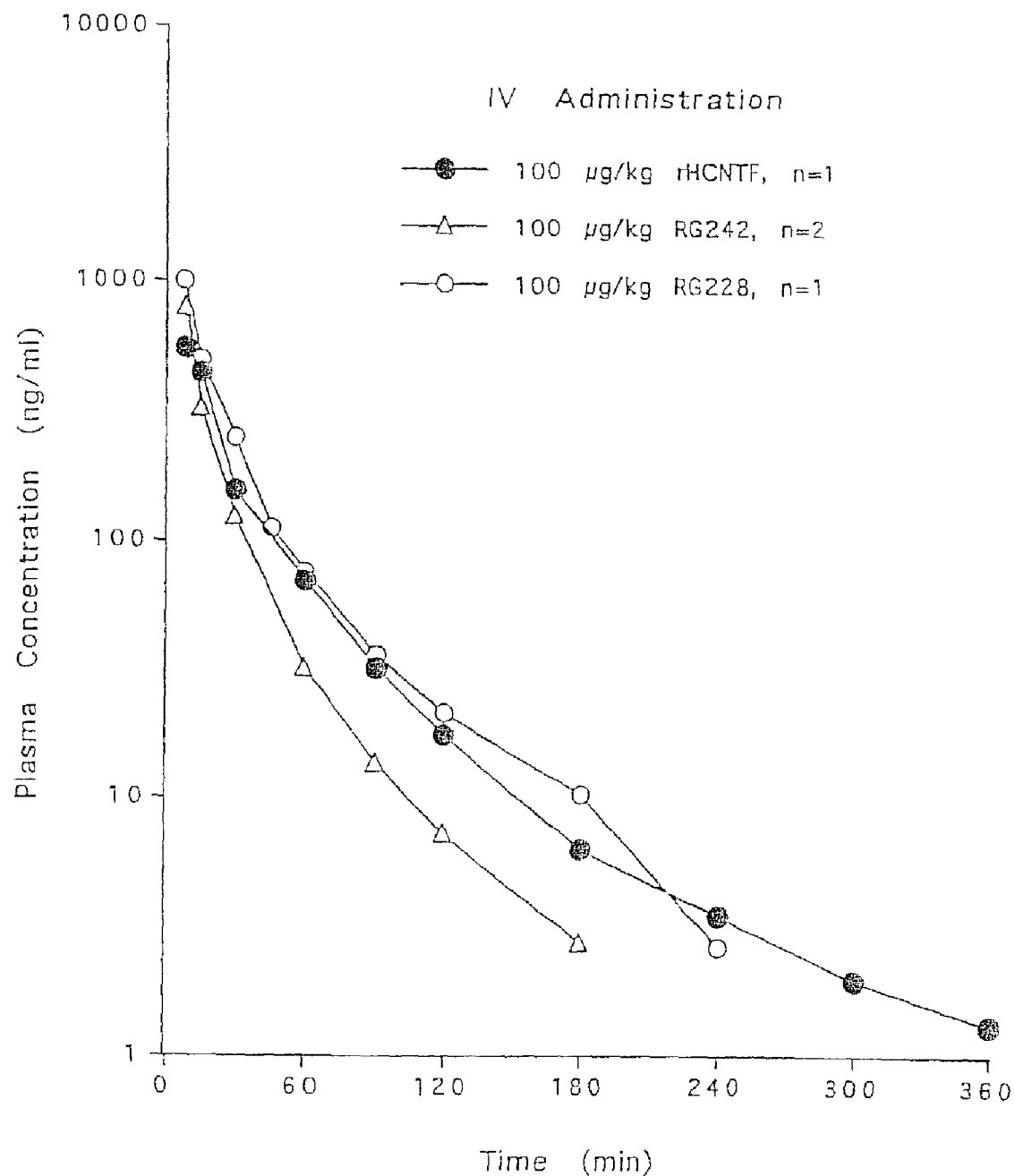
FIG. 9—Average plasma concentration time profiles in the rat after intravenous (IV) administration of rHCNTF, RG228 and RG242 normalized to 100 µg/kg dose for all three compounds.

The average plasma concentration time profiles in the rat after IV administration of rHCNTF, RG228 and RG242 are shown in FIG. 9, normalized to 100 μg/kg dose for all three compounds. The average pharmacokinetic parameters are summarized in Table 1.

After i.v. administration to rats, RG242 had a distribution phase α somewhat faster than that of rHCNTF and RG228. The disposition phase β for RG242 and RG228 was faster than that of rHCNTF. Thus, RG242 appeared to be distributed into the body and cleared from systemic circulation somewhat more rapidly than rHCNTF, whereas RG228 appeared to be distributed into the body as fast as rHCNTF and cleared from systemic circulation somewhat faster. The area under the concentration time curve (AUC) for RG242 was comparable to that of rHCNTF, indicating that the total body clearance ($Cl_T$) was about the same for the two compounds. A twice larger area was observed with RG228. However, the apparent volume of distribution ($V_{area}$), which is a function of both β and AUC, was approximately twofold smaller for both RG228 and RG242 relative to rHCNTF, suggesting that these variants are distributed less widely. The limited number of animals used in these evaluations did not allow the quantitative distinction of these values. However, these results clearly indicate that the distribution and disposition kinetics of RG228 and RG242 after i.v. administration are not substantially different from those of rHCNTF.

Figure 10:
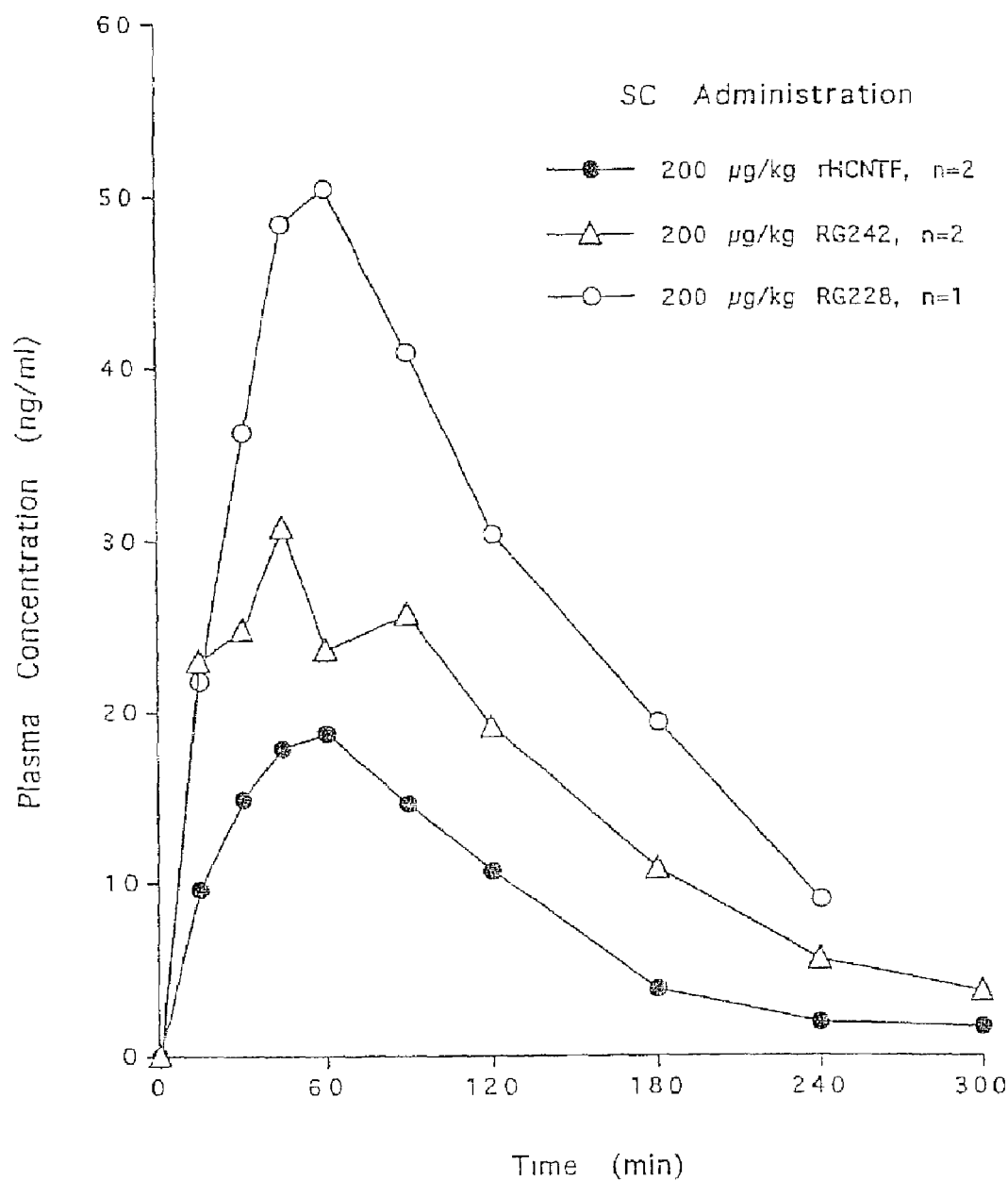
FIG. 10—Average plasma concentration time profiles in the rat after subcutaneous (SC) administration of rHCNTF, RG228 and RG242 normalized to 200 µg/kg dose for all three compounds.

After s.c. administration, RG228 and RG242 had a 2–3 fold longer absorption phase (Ka) relative to rHCNTF (FIG. 10 and Table 2). The disposition phase of RG242 was also somewhat longer. The longer apparent terminal disposition phase of RG242 after s.c. dosing compared to i.v. administration may be attributed to the incomplete characterization of the terminal phase after the i.v. injection. Overall, the absolute bioavailability of RG228 (13.7%) and RG242 (10.9%) were comparable to that of rHCNTF (6.0%), in view of the fact that in two previous independent studies, the absolute bioavailability of rHCNTF was found to be 14.2% (n=18) and 7.5% (n=8) (D. B. Lakings, et al., DSER 93/DMAP/006, "Dose Proportionality and Absolute Bioavailability of rHCNTF in the Rat Following Subcutaneous Administration at Eight Dose Levels" (Phoenix International Project No. 920847) 10 Nov. 1993; D. B. Lakings, et al., Dose Proportionality and Absolute Bioavailability of rHCNTF Administered Subcutaneously to Rats. AAPS Ninth Annual Meeting, San Diego, Calif., November, 1994).

Therefore, the bioavailabilities of rHCNTF, RG228 and RG242 are not significantly different within experimental error.

Figure 12:
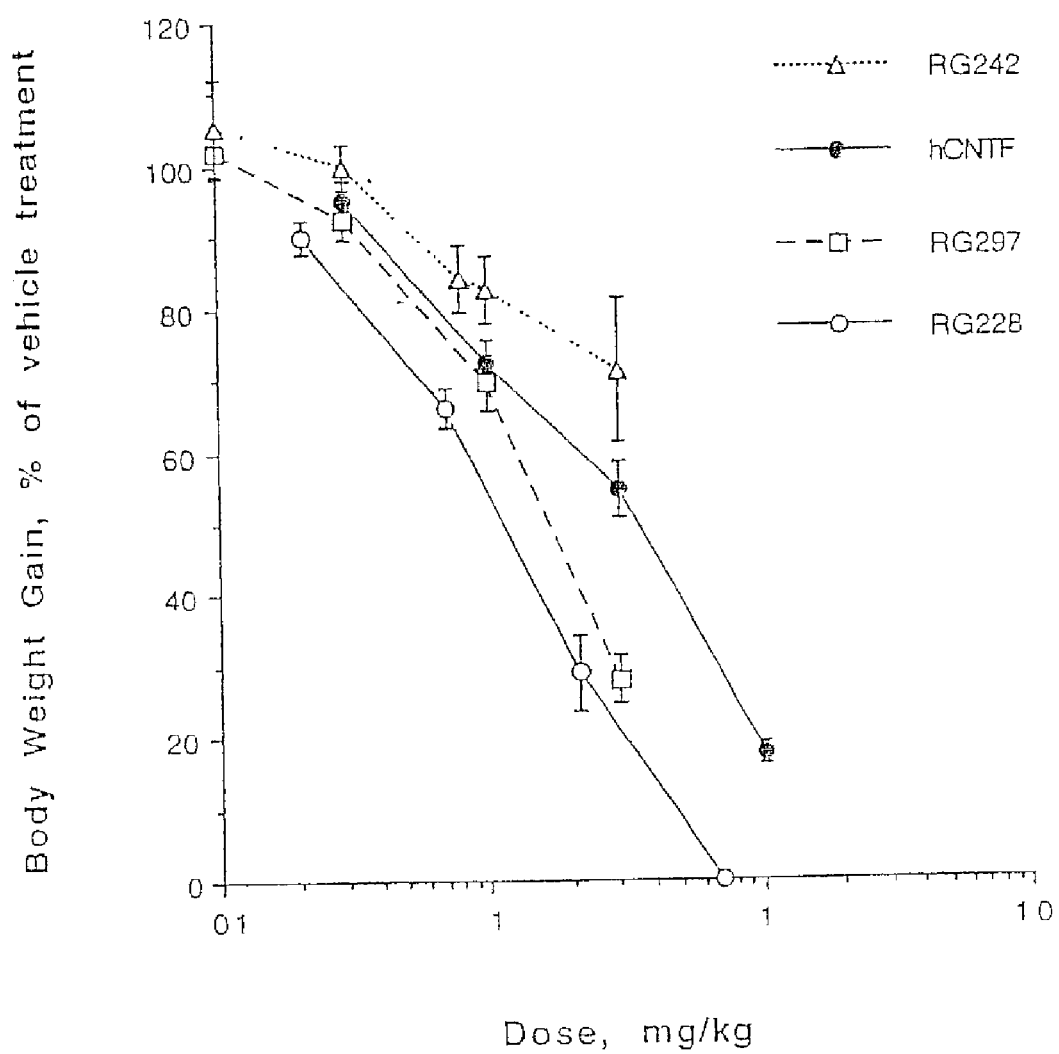
FIG. 12—Comparison of in vivo toxicity for hCNTF, RG228, RG242 and RG297.

Efficacy and Toxicity In Vivo—In control experiments, denervation of the soleus muscle resulted in a loss of 40% of muscle wet weight by 7 days. This value is very accurate and reproducible, since it varies by only 3% among independent experiments. Daily administration of rHCNTF resulted in a dose-dependent rescue of muscle wet weight at an $ED_{50}=0.12$ mg/kg and a maximal effect at 0.3 mg/kg (FIG. 11). At the same time, even though animals continued to gain weight during the course of these experiments, they clearly did not gain as much as their vehicle-treated counterparts ($p<0.01$; FIG. 12), especially at the maximally efficacious doses.

In the course of several experiments conducted in parallel with rHCNTF, it was determined that the 63QR substitution resulted in a 2-fold increase in potency in vivo (FIG. 11) but, also, a concomitant 2 fold increase in toxicity (FIG. 12) In contrast, RG297, which carries the additional C17A and ΔC13 modifications, shows a 2.6 fold greater potency but the same toxicity relative to rHCNTF. Finally, RG242 produced a 2.8 fold increased potency and an 2.4 fold decreased toxicity relative to rHCNTF. These results are summarized in Table 3.

The relative therapeutic index (T.I.) for each of these compounds was calculated as the ratio of the $TD_{25}$ and $ED_{50}$ values, normalized to that of rHCNTF. While the T.I. of RG228 is equal to that of rHCNTF, the T.I. of RG297 and RG242 is 2.5 and 6.8 fold superior to that of rHCNTF, respectively.

Therefore, RG297 and RG242 have superior pharmacological properties than rHCNTF. This is of great relevance to the clinical situation where decreased body weight is observed upon rHCNTF treatment in humans.

One skilled in the art will recognize that other alterations in the amino acid sequence of CNTF can result in a biologically active molecule which may have enhanced properties. For example, applicant has prepared a 17CS mutant which has a serine residue in place of the cysteine residue at position 17 and is biologically active. Applicant has also prepared a biologically active quadruple mutant, 17CA, ΔC13,63QR,64WA (SEQ ID NO:28). Further CNTF mutants, all of which retain biological activity, are set forth in Table 4.

TABLE 1

Average Pharmacokinetic Parameters for rHCNTF, RG228 and RG242 after Intravenous Administration to Rats at 100 μg/kg.

| Pharmacokinetic Parameter | Compound rHCNTF | RG242 | RG228* |
|---|---|---|---|
| n | 1 | 2 | 1 |
| $C_0$ (ng/ml) | 726 | 2,175 | NC |
| $AUC_{0-\infty}$ (ng · min/ml) | 20,230 | 22,890 | 55,800 |
| $\alpha$ (min$^{-1}$) | 0.0492 | 0.0856 | 0.041 |
| $t_{1/2\alpha}$ (min) | 14 | 8 | 17 |
| $\beta$ (min$^{-1}$) | 0.0106 | 0.0200 | 0.0176 |
| $t_{1/2\beta}$ (min) | 65 | 35 | 39 |
| $V_{area}$ (ml/kg) | 470 | 220 | 204 |
| $Cl_T$ (ml/min/kg) | 4.9 | 4.4 | 3.6 |

*RG228 values normalized to a 100 μg/kg i.v. dose to be comparable to the other two compounds that were administered at 100 μg/kg.
$C_0$: Estimated by extrapolation of the first two plasma concentrations to time zero.
NC: Not calculated

TABLE 2

Average Pharmacokinetic Parameters for rHCNTF, RG228 and RG242 After Subcutaneous Administration to Rats at 200 μg/kg

| Pharmacokinetic Parameter | Compound rHCNTF | RG242 | RG228 |
|---|---|---|---|
| n | 2 | 2 | 1 |
| $C_{max}$ (ng/ml) | 18 | 32 | 50 |
| $T_{max}$ (min) | 30–45 | 30–45 | 60 |
| $AUC_{0-\infty}$ (ng · min/ml) | 2,425 | 4,980 | 7,620 |
| Absolute Bioavailability | 6.0 | 10.9 | 13.7 |
| $k_e$ (min$^{-1}$) | 0.0133 | 0.0083 | NC |
| $t_{1/2ke}$ (min) | 52 | 82 | NC |
| $k_a$ (min$^{-1}$) | 0.0401 | 0.0180 | 0.0102 |
| $t_{1/2ka}$ (min) | 17 | 39 | 68 |

NC: Not calculated.

TABLE 3

Efficacy, Toxicity and Therapeutic Index of rHCNTF and Derivatives

| Compound | $ED_{50}$ (mg/kg) | $TD_{25}$ (mg/kg) | Therapeutic Index ($TD_{25}/ED_{50}$) | Relative Therapeutic Index |
|---|---|---|---|---|
| rHCNTF | 0.12 | 0.087 | 0.72 | 1.0 |
| RG228 | 0.065 | 0.047 | 0.72 | 1.0 |
| RG297 | 0.045 | 0.080 | 1.78 | 2.5 |
| RG242 | 0.043 | 0.21 | 4.88 | 6.8 |

TABLE 4

Biological activity of rHCNTF variants on E8 chick ciliary neurons. Potency units (1/$EC_{50}$) are shown relative to human CNTF which is assigned a value of 100. One potency unit is defined as the reciprocal ligand concentration showing the same biological activity as 1 ng/ml rHCNTF.

| CNTF | POTENCY |
|---|---|
| rat | 500.0 |
| human | 100.0 |
| 17CS | 100.0 |
| 63QA | 87.0 |
| 63QN | 100.0 |
| 63QH | 2.5 |
| 63QE | <1 |
| 63QK | 1.1 |
| 63QR | 400.0 |
| 64WA | 2.0 |
| 63QR64WA | 9.0 |
| 63QR64WF | 250.0 |
| 63QR64WH | 25.0 |
| 63QR64WQ | 10.0 |

Example 7

Efficacy of CNTF and Variants in Animal Models of Huntington's Disease

Background

Glutamate receptor-mediated excitotoxicity has been hypothesized to play a role in numerous neurodegenerative diseases, including Huntington disease and motor neuron disease (DiFiglia, M. 1990, Trends Neurosci. 13:286–289; Rothstein, et al., 1995, J. Neurochem. 65:643–651). The predominant neuropathological feature of Huntington disease is a massive degeneration of the medium-sized, GABAergic, striatal output neurons, without substantial loss of striatal interneurons (Albin, et al., 1989, Trends Neurosci. 12:366–375; Harrington, et al., 1991, J. Neuropathol. Exp. Neurol. 50:309). The preferential loss of striatal output neurons observed in Huntington disease, and the resulting dyskinesia, are mimicked in rodent or primate models in which an NMDA glutamate receptor agonist, quinolinic acid, is injected into the striatum (DiFiglia, M., 1990, Trends Neurosci. 13:286–289).

In the absence of a genetic animal model for HD, neuroscientists continue to rely on acute lesion models for investigation of the HD phenotype. The classic animal model of HD involves production of an excitotoxic lesion of the rat striatum using a glutamate agonist of the NMDA-receptor class. In such lesion paradigms, injection of the neurotoxin directly into the striatum results in loss of the medium sized intrinsic striatal neurons which utilize gamma-aminobutyric acid (GABA) as their neurotransmitter, with relative preservation of the two classes of striatal interneurons which utilize either acetylcholine or somatostatin and neuropeptide Y as their neurotransmitters. Most recent studies have relied upon intrastriatal injection of quinolinic acid, which seems to most faithfully reproduce the appearance of the HD striatum.

Figueredo-Cardenas et al. (1994, Exp. Neurol 129:37–56) injected quinolinic acid (QA), into the striatum in adult rats and 2–4 months post lesion explored the relative patterns of survival for the various different types of striatal projection neurons and interneurons as well as the striatal efferent fibers in the different striatal projection areas. The perikarya of all projection neuron types (striatopallidal, striatonigral, and striato-entopeduncular) were more vulnerable than the cholinergic interneurons. Among projection neuron perikarya, there was evidence of differential vulnerability, with striatonigral neurons appearing to be the most vulnerable. Examination of immunolabeled striatal fibers in the striatal target areas indicated that striato-entopeduncular fibers better survived intrastriatal QA than did striatopallidal or striatonigral fibers. The apparent order of vulnerability observed in this study among projection neurons and/or their efferent fiber plexuses and the invulnerability observed in this study of cholinergic interneurons is similar to that observed in HD.

In another animal model, systemic administration of 3-nitropropionic acid (3-NP) leads to neuropathological changes similar to those seen in Huntington's disease (HD). Although the behavioral hypoactivity seen in these animals differs from the observed hyperactivity in most excitotoxic models of HD, 3-NP is considered by some to provide a better model of juvenile onset and advanced HD. The neuropathological effects of 3-NP include loss of intrinsic striatal cholinergic neurons, but some sparing of large AChE positive neurons, minimal damage of NADPH-diaphorase-containing neurons, and glial infiltration (Borlongan et al., 1995, Brain Res. Bull. 365:49–56). There have been relatively few studies with 3-NP as a neurotoxic model of HD. Its faithfulness and utility remain to be explored.

Recent studies have begun to explore the relationship between excitotoxic injury and the role of Huntingtin in the striatum. Striatal injection of quinolinic acid in mice induces increased immunoreactivity for Huntingtin in some remaining neurons but not in glial cells. This increase is apparent in both neuronal cell bodies and in cell processes in the white matter six hours after excitotoxic challenge. Thus Huntingtin may be involved in the response to excitotoxic stress in these neurons Tatter, et al., 1995, Neuroreport 6:1125–1129). Following an initial increase between 1 h and 6 h, IT15 mRNA levels declined in a pattern homologous to a group of neuron-specific genes. Decreased mRNA levels after 24 h demonstrated that glial transcription is not activated by neurodegeneration or gliosis. The 1 h and 24 h mRNA levels strongly suggest that IT15 transcription preferentially localizes to degenerating neurons. Carlock et al., 1995, Neuroreport 6:1121–1124.

Excitotoxic injury to the striatum also mimics certain of the aspects of cell death seen in HD brain (Beal et al., 1986, Nature 321:168–171). In the neostriatum of individuals with HD, patterns of distribution of TUNEL-positive neurons and glia were reminiscent of those seen in apoptotic cell death during normal development of the nervous system; in the same areas, nonrandom DNA fragmentation was detected occasionally. Following excitotoxic injury of the rat striatum, internucleosomal DNA fragmentation (evidence of apoptosis) was seen at early time intervals and random DNA fragmentation (evidence of necrosis) at later time points. In addition, EM detected necrotic profiles of medium spiny neurons in the lesioned rats. Thus, apoptosis occurs in both HD and excitotoxic animal models. Furthermore, apoptotic and necrotic mechanisms of neuronal death may occur simultaneously within individual dying cells in the excitotoxically injured brain. (Portera et al., 1995, J. Neuroscience 15:3775–3787).

The Tdt-mediated dUTP-biotin nick end labeling (TUNEL) technique has been investigated in preliminary studies of a variety of pathologic conditions of the human brain (e.g., gliomas, traumatic brain injury, Parkinson's disease, Parkinson's-Alzheimer's complex, multisystem atrophy, striatonigral degeneration). Only Huntington's disease revealed significant and consistent labeling with this method. Thomas et al., 1995, Experimental Neurology 133: 265–272). c-fos expression increases soon after quinolinic acid injection, is widespread in rat brain, but is effectively absent by 24 h postinjection. DNA fragmentation, however, is limited to striatum and is maximal at 24 h after injection. These results demonstrate the sensitivity of in situ nick translation for the detection of regional neuropathology and illustrate the temporal and spatial relationship of c-fos expression to excitotoxic neuronal death (Dure et al., 1995, Exp. Neurol. 133:207–214).

Excitotoxic lesions have also been used to explore possible therapeutic avenues in HD. Excitotoxic striatal lesions induced by quinolinic acid, a model for Huntington's disease, have been used to test for neuroprotective actions of nerve growth factor (NGF) on striatal cholinergic and GABAergic neurons in adult rats following quinolinic acid lesion (150 mmol). Daily intrastriatal NGF administration for one week increased the cellular expression of choline acetyltransferase messenger RNA three times above control levels and restored the levels of Trk A messenger RNA expression to control levels. In contrast to the protective effects on cholinergic cells, NGF treatment failed to attenuate the quinolinic acid-induced decrease in glutamate decarboxylase messenger RNA levels. Thus, striatal glutamate decarboxylase messenger RNA-expressing GABAergic neurons which degenerate in Huntington's disease are not responsive to NGF.

Frim, et al. (1993, J. Neurosurg. 78:267–273) implanted fibroblasts secreting NGF into quinolinic-acid lesioned rat striata. They found that preimplantation of NGF-secreting fibroblasts placed within the corpus callosum reduced the maximum cross-sectional area of a subsequent excitotoxic lesion in the ipsilateral striatum by 80% when compared to the effects of a non-NGF-secreting fibroblast graft, and by 83% when compared to excitotoxic lesions in ungrafted animals ($p<0.003$).

Materials and Methods

Trophic Factors. Recombinant human BDNF, nerve growth factor (NGF) and NT-3, and recombinant rat CNTF were prepared in E. coli and characterized as described (Maisonpierre, et al., 1990, Science 247:1446–1451; Masiakowski, et al., 1991, J. Neurochem. 57:1003–1012). Axokine1 (Ax1) is the designation for recombinant human CNTF with the following modifications: substitutions of alanine for cysteine at position 17 and arginine for glutamine at position 63, and deletion of the 13 C-terminal amino acids. This CNTF analog has enhanced solubility, is stable for at least a week at 37° C. in physiological buffer, and exhibits 4–5-fold greater potency in vitro relative to native human CNTF (Panayotatos et al., 1993, J. Biol. Chem. 268:19000–19003). Animal Treatments. All animal procedures were conducted in strict compliance with protocols approved by the institutional animal care and use committee.

Trophic factor delivery by osmotic pump. A 30-gauge osmotic pump infusion cannula and a 22-gauge guide cannula (5.0 and 2.2 mm long, respectively) were chronically implanted side-by-side into the left hemisphere (stereotaxic coordinates AP 0.7, ML 3.2 relative to bregma; incisor bar 3.3 mm below the interaural line) in 250–300 g male, Sprague-Dawley rats under deep chloral hydrate (170 mg/kg) and pentobarbital (35 mg/kg) anesthesia. Thirty days later, the rats were again anesthetized and an Alzet osmotic minipump 2002 (two-week capacity at a delivery rate of 0.5 µl/hr), containing 0.1 M phosphate buffered saline (PBS) (pH 7.4), or PBS solutions of recombinant human NGF (0.9 mg/ml), human BDNF (1 mg/ml), human NT-3 (1 mg/ml), rat CNTF (0.78 mg/ml), or Ax1 (0.4 mg/ml) was connected by plastic tubing to the infusion cannula and implanted subcutaneously (Anderson, et al., 1995, J. Comp. Neurol. 357:296–317). Due to the dead volume of the infusion cannula and tubing, the delivery of neurotrophic factor into the brain began about 1 day after pump implantation. Neurotrophins maintained in osmotic pumps at 37° C. for 12 days were completely stable, as determined by bioassay, and effective intrastriatal delivery of the neurotrophins was verified by immunohistochemical staining of sections for the appropriate factor (Anderson, et al., 1995, J. Comp. Neurol. 357:296–317). Three or four days after pump implantation, anesthetized rats received an injection of quinolinic acid (50 mmol in 1 µl phosphate buffer, pH 7.2, over 10 minutes) through the guide cannula using a 10-µl Hamilton syringe with a 28-gauge blunt-tipped needle.

Trophic factor delivery by daily injection. A 22-gauge guide cannula (2.2 mm long) was chronically implanted into the left hemisphere (stereotaxic coordinates AP 0.5, ML 3.0) of anesthetized rats, as described above. Beginning 1 week later, anesthetized rats received a daily intrastriatal injection of Ax1 (0.4 µg in 1 µl, over 10 minutes) or vehicle through the guide cannula using a Hamilton syringe. Ax1 was injected for 3 consecutive days before and 1 day after injection of quinolinic acid, which was injected as described above. Histological Procedures and Analysis. Brains perfusion-fixed in 4% paraformaldehyde were collected 8 or 9 days after the quinolinic acid injection, and cut in the coronal plane into forty-micron thick sections that were stained with thionin. In each experiment, a series of 1 in 12 Nissl-stained sections was evaluated by an investigator unaware of treatment conditions, and the relative loss of medium-sized striatal neurons was rated on the following scale: 0 (no neuron loss), 1 (clear but slight neuron loss), 2 (moderate neuron loss), 3 (severe but not total neuron loss), 4 (total loss of medium-sized neurons within the field of the quinolinic acid injection). In cases where neuron loss appeared intermediate to two criteria, a half score between the two closest scores was assigned. Neuron loss scores that were assigned independently by two different observers in the experiments using BDNF and NT-3 were within 0–0.5 points of each other for 40 of 42 rats (correlation coefficient=0.8; p=0.0001).

In the experiment using CNTF, neuron loss also was evaluated by counting neurons in sections taken 0.5 mm rostral to the infusion cannula. For each section, neurons were counted that intersected every vertical line of a 10×10 sampling grid placed over seven fields, 0.4×0.4 mm, within the treated striatum. The first field was located slightly lateral to the center of the striatum, at the center of a typical quinolinic acid-induced lesion (i.e. immediately rostral to the tip of the infusion cannula). The six other fields were selected by moving diagonally from the first field, twice each in the dorsomedial and the ventromedial directions, and once each in the dorsolateral and the ventrolateral directions. To control for possible variation in section thickness, seven fields in equivalent locations were sampled in the contralateral striatum (approximately 600 neurons counted per 7 fields), and neuron survival was expressed as a percentage of neurons on the treated side relative to the intact side. The results of actual neuron counts (31 and 61% neuron loss for CNTF- and PBS-treated groups, respectively) showed close agreement with the results of the neuron loss scoring system (mean neuron loss scores of 1.67 and 3.25, respectively), as assessed by regression analysis (Spearman rank correlation coefficient=0.82, $p<0.05$).

Differences between experimental groups and their respective control groups were evaluated by unpaired t-test.

Results

In a series of experiments, quinolinic acid (50 mmol) was injected into the left striatum of adult rats 3 or 4 days after the start of intrastriatal infusion of neurotrophic factor by osmotic pump (nominal delivery rates: human NGF, 10.8 µg/day; human BDNF or NT-3, 12.0 µg/day; rat CNTF, 9.4 µg/day). This dose of quinolinic acid is toxic to medium-sized striatal output neurons, which constitute over 90% of all striatal neurons, yet leaves the striatal populations of cholinergic interneurons and parvalbumin/GABAergic interneurons largely intact (Qin, et al., 1992, Experimental Neurology 115:200–211; Figueredo-Cardenas, et al., 1994, Exp. Neurol. 129:37–56). Microscope analysis of Nissl-stained sections from brains collected 8–9 days after injection of quinolinic acid demonstrated no significant sparing of medium-sized striatal neurons in BDNF-, NGF-, or NT-3-treated brains (FIG. 13). In an additional set of experiments, no neuron sparing was apparent when quinolinic acid was injected 7 days after the start of BDNF or NGF infusion.

Figure 14:
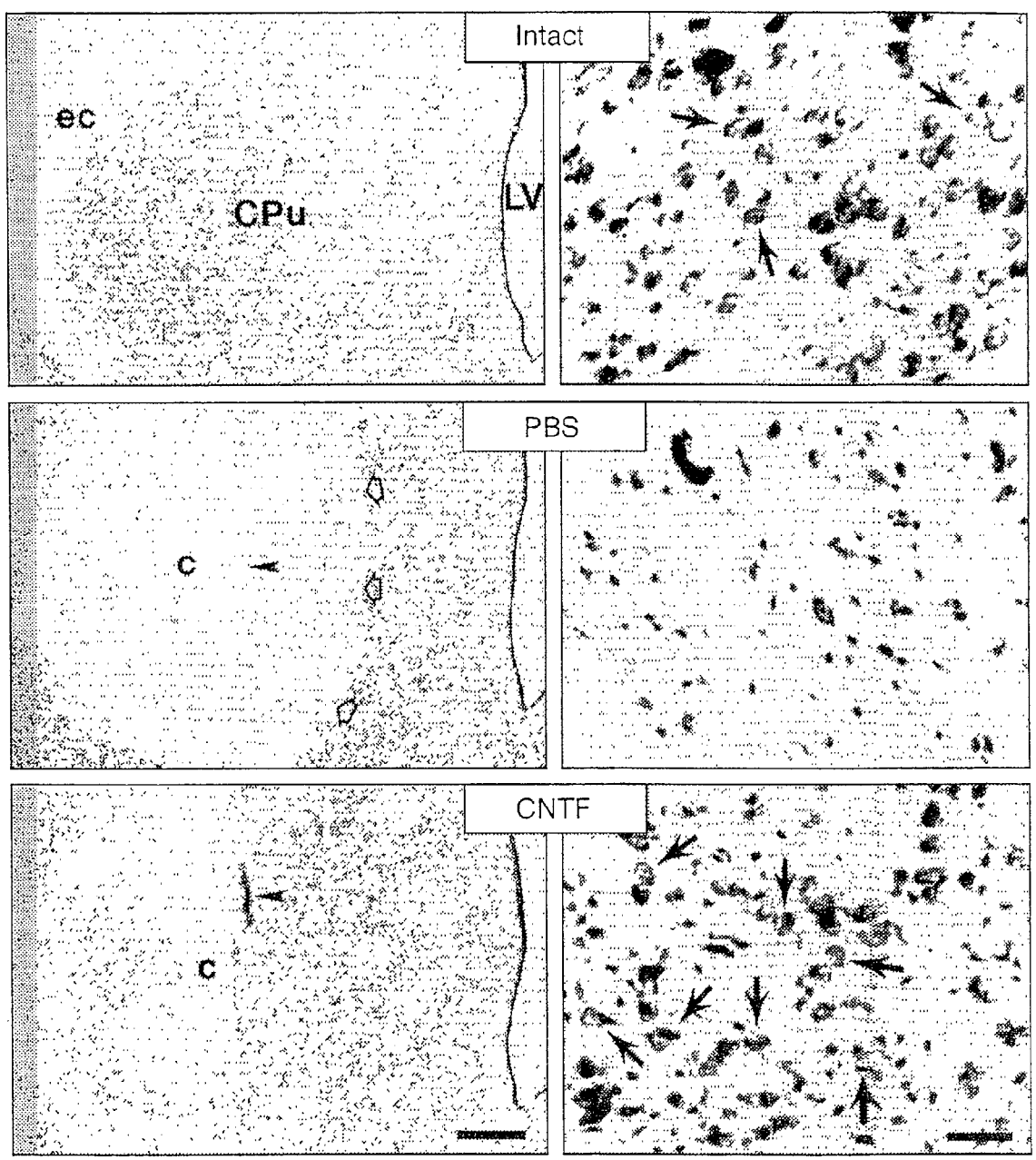
FIG. 14—Representative Nissl-stained sections (coronal plane) from brains treated with CNTF or PBS and injected with quinolinic acid. Top left: A view of an untreated, intact caudate-putamen (CPu). Top right: A higher magnification view of the lateral CPu showing numerous medium-sized neurons, a few of which are indicated by arrows. Middle and bottom left: The left CPu in brains treated with PBS or CNTF and injected with quinolinic acid. The two tracks in the CPu were left by the PBS or CNTF infusion cannula (c) and the quinolinic acid injection needle (arrowhead); open arrows indicate the medial boundary of the lesion. Middle and bottom right: Higher magnification views 250 µm lateral to the cannula illustrating the virtually complete absence of medium-sized striatal neurons in the PBS-treated brain (neuron loss score=4), and the presence of numerous, normal-appearing neurons in the CNTF-treated brain (some of the surviving neurons are indicated by arrows; neurons loss score=2). ec, external capsule; LV, lateral ventricle. Left scale bar=0.5 mm; right scale bar=30 µm.

In striking contrast, neuron survival was significantly greater in rats treated with CNTF compared to rats treated with vehicle alone (FIG. 14), as determined by neuron counts that demonstrated a mean percent survival (±SEM) of 69±17 and 29±11%, respectively (unpaired t-test, t(5)=2.12, p=0.04), or as assessed by assignment of semi-quantitative neuron loss scores (FIG. 15). Surviving neurons in CNTF-treated brains were disseminated throughout the striatal area affected by the quinolinic acid injection.

Given the favorable effect demonstrated by CNTF, a similar experiment was conducted using a polypeptide CNTF receptor agonist, Axokine 1 (Ax1) (24). As observed after administration of CNTF, infusion of Ax1 (4.8 µg/day) resulted in significant sparing of medium-sized striatal neurons exposed to quinolinic acid (FIG. 15). This result supports the conclusion that CNTF receptor-mediated mechanisms effect protection of striatal neurons from NMDA receptor-mediated excitotoxicity.

The neuroprotective effect of CNTF or Ax1 was achieved without apparent adverse effects on behavior or health, as indicated, for example, by body weight. Body weights measured at the end of the experiments were not significantly affected by CNTF or Ax1 treatment (unpaired t-test). The mean body weights (±SEM) of the trophic factor-treated and the vehicle-treated groups in the CNTF experiment were 369±20 g and 331±15 g, respectively, (p=0.21); mean body weights in the Ax1 experiment were 431±26 g and 453±14 g, respectively, (p=0.44).

Figure 16A:
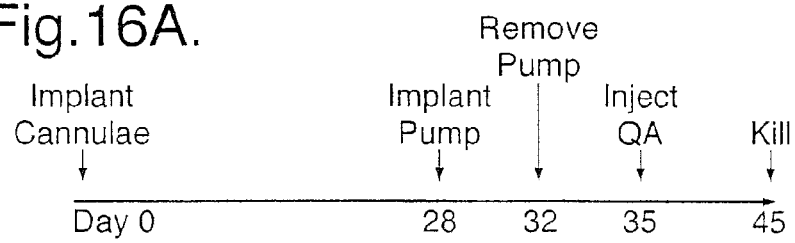
FIG. 16—Effect of treatment with Ax1 on medium-sized striatal neuron loss induced by intrastriatal injection of quinolinic acid (QA). Above each graph, a time line indicates the experimental scheme. A. Mean neuron loss score (±SEM) for groups treated with Ax1 (n=6) or PBS (n=5) in an experimental paradigm similar to that described in FIG. 1 legend, except the osmotic pump was implanted for only 4 days and the injection of quinolinic acid was given 3 days after removal of the pump. B. Mean neuron loss score (±SEM) for groups receiving a daily intrastriatal injection of Ax1 (n=6) or PBS (n=6) for 3 days before and 1 day after an injection of quinolinic acid. *unpaired t-test, A: t(9)=2.5, p=0.03; B: t(10)=2.3, p=0.04.
Figure 16A:
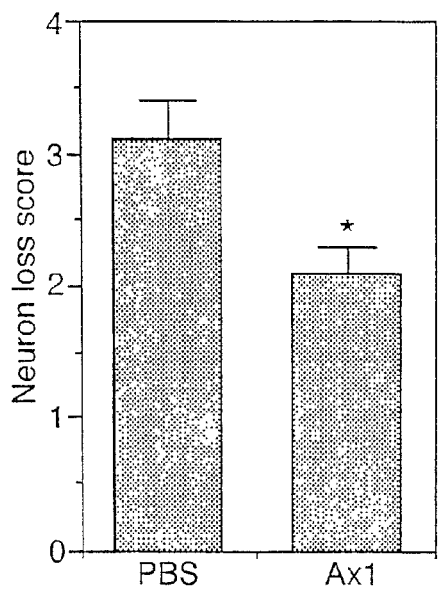
Figure 16B:
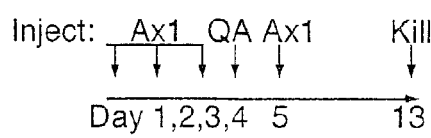
Figure 16B:
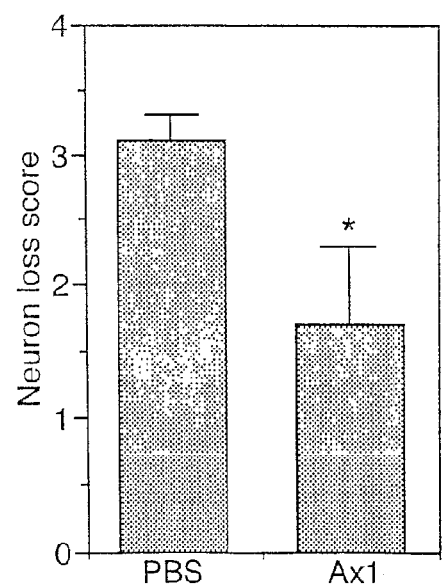

Two additional experiments were performed to determine whether the neuroprotective effect of CNTF receptor ligands might persist after termination of neurotrophic factor administration, and whether treatment is effective when a lower dose of trophic factor is delivered intermittently. In the first experiment, rats were infused intrastriatally with Ax1 (4.8 μg/day) or vehicle for 3 days and then delivery was terminated by removal of the osmotic pump. Quinolinic acid was injected into the striatum 3 days thereafter (FIG. 16A). In the second experiment, rats received a daily intrastriatal injection of Ax1 (0.4 μg/day) or vehicle for 3 days before and 1 day after intrastriatal injection of quinolinic acid (FIG. 16B); thus these rats received a total of only 1.6 μg Ax1. In both experiments, microscope analysis of Nissl-stained sections demonstrated significant sparing of medium-sized striatal neurons in Ax1-treated brains that was comparable to sparing seen when CNTF or Ax1 were infused continuously for the duration of the experiment (FIG. 16).

Discussion

Since over 90% of the neurons in the striatum are medium-sized, GABAergic, striatonigral and striatopallidal projection neurons (Graybiel, A. M., 1990, TINS 13:244–254), the present results show that treatment with CNTF or a CNTF receptor agonist protects striatal output neurons against excitotoxic insult. Thus, CNTF is one of the first purified trophic factors demonstrated to protect striatal output neurons after pharmacological application in an adult animal model of Huntington disease. Among other factors characterized, only treatment with basic fibroblast growth factor has been reported to diminish the size of a striatal lesion induced by injection of N-methyl-D-aspartate (NMDA) or malonic acid in adult and neonatal rats (Nozaki, et al., 1993, J. Cereb. Blood Flow Metab. 13:221–228; Kirschner, et al., 1995, J. Cereb. Blood Flow Metab. 15:619–623). Although NGF-secreting fibroblasts implanted near the striatum have been shown to protect medium-sized striatal neurons from quinolinic acid in rats (Frim, et al., 1993, NeuroReport 4:367–370; Emerich, et al., 1994, Exp. Neurol. 130:141–150), we obtained no survival-promoting effect on these neurons with purified NGF, in agreement with several earlier studies (Davies, et al., 1992, Neurosci. Lett. 140:161–164; Venero, et al., 1994, Neuroscience 61:257–268; Kordower, et al., 1994, Proc. Natl. Acad. Sci. USA 91:9077–9080). This finding suggests that NGF is not the sole mediator of the neuroprotection provided by NGF-secreting fibroblasts. We did, however, observe that the large, darkly staining, presumably cholinergic interneurons were more prominent in NGF-treated brains, as previously reported (Davies, et al., 1992, Neurosci. Lett. 140:161–164; Kordower, et al., 1994, Proc. Natl. Acad. Sci. USA 91:9077–9080; Perez-Navarro, et al., 1994, Eur. J. Neurosci. 6:706–711). Striatal expression of the high-affinity NGF receptor, TrkA, is restricted to cholinergic interneurons (Steininger, et al., 1993, Brain Res. 612:330–335), consistent with the finding of a selective action of NGF on these neurons, whereas the high-affinity receptors for BDNF and NT-3 (TrkB and TrkC) are expressed by numerous medium-sized striatal neurons (Altar, et al., 1994, Eur. J. Neurosci. 6:1389–1405). BDNF and NT-3 (unlike NGF) promote the survival and phenotypic differentiation of embryonic, GABAergic, striatal output neurons in vitro (Mizuno, et al., 1994 Dev. Biol. 165:243–256; Ventimiglia, et al., 1995, Eur. J. Neurosci). Moreover, these neurotrophins can protect certain neuron populations from glutamate toxicity in vitro (Lindholm, et al., 1993, Eur. J. Neurosci. 5:1455–1464; Shimohama, et al., 1993, Neurosci. Lett. 164:55–58; Cheng, et al., 1994, Brain Res. 640:56–67). Nevertheless, infusion of BDNF or NT-3 does not appear to protect striatal output neurons against NMDA receptor-mediated excitotoxicity in vivo, although intracerebral infusion of BDNF or NT-3 at comparable doses elicits pronounced biological effects in the striatum and elsewhere in the brain (Lindsay, et al., 1994, TINS 17:182–190). The contrasting results between in vivo and in vitro studies may be explained by differences in neuron type (striatal vs. hippocampal, cortical or cerebellar), a difference in the developmental stage of the neurons (adult vs. embryonic), or the presence of glutamatergic synaptic input in vivo.

The neuroprotective effect displayed by CNTF receptor ligands may occur through direct action on medium-sized striatal neurons, since there is abundant expression of mRNA for components of the CNTF receptor (CNTFRα, LIFRβ, gp130) in the striatum (Ip, et al., 1993, Neuron 10:89–102; Rudge, et al., 1994, Eur. J. Neurosci. 6:693–705). Potential mechanisms might include alteration of the expression or function of glutamate receptors, thereby modifying neuron sensitivity to glutamatergic stimulation, or enhancement of the neuron's capacity to regulate the cytosolic concentration of calcium ion, an increase in which is thought to be a critical event initiating the neurodegenerative process (Choi, D. W., 1988, Neuron 1:623–634). The possibility that CNTF acts as a glutamate receptor antagonist to block quinolinic acid toxicity is unlikely, since CNTF does not block the toxic effects of glutamate in vitro (Mattson, et al., 1995, J. Neurochem. 65:1740–1751). On the other hand, CNTF receptor ligands could potentially act indirectly, via other components of the striatum. For example, elimination of nigral or cortical input to the striatum prior to exposure to quinolinic acid results in a significant reduction in the loss of striatal neurons (DiFiglia, M., 1990, Trends Neurosci. 13:286–289; Buisson, et al., 1991, Neurosci. Lett. 131:257–259) indicating that the combined actions of exogenous toxin and endogenous neurotransmitters are required to induce cell death. Thus, a reduction in synaptic transmission at either glutamatergic or dopaminergic synapses would likely protect striatal neurons from an injection of quinolinic acid. Although astrocytes do not normally express detectable CNTFRα in vivo (Ip, et al., 1993, Neuron 10:89–102), astrocytes do express all CNTF receptor components when activated by brain injury or when maintained in vitro (Rudge, et al., 1994, Eur. J. Neurosci. 6:693–705). Furthermore, intracerebral delivery of CNTF appears to activate astrocytes 10–48 hours after exposure, as indicated by increased content of glial fibrillary acidic protein and its mRNA (Levison, et al., 1995, Soc. Neurosci. Abst. 21:497; Winter, et al., 1995, Proc. Natl. Acad. Sci. USA 92:5865–5869). Whether activated indirectly or directly by CNTF, astrocytes might promote neuron survival through enhanced sequestration of excitatory amino acids or by release of substances that protect neurons.

The striatal neuron populations protected from excitotoxic damage by CNTF receptor-mediated events in the present study are the same types selectively lost in Huntington disease (Albin, et al., 1989, Trends Neurosci. 12: 366–375). A potential link between excitotoxic stimulation and increased expression of the Huntington disease gene has recently been suggested (Carlock, et al., 1995, NeuroReport 6:1121–1124; Tatter, et al., 1995, NeuroReport 6:1125–1129). While extensive studies are in progress to identify the mechanisms which lead to Huntington disease, existing lines of evidence clearly implicate a role for NMDA receptor-mediated excitotoxicity (DiFiglia, M., 1990, Trends Neurosci. 13:286–289).

Example 8

PEGylation of Axokine Protein

Pegylation of proteins has been shown to increase their in vivo potency by enhancing stability and bioavailability while minimizing immunogenicity. It is known that the properties of certain proteins can be modulated by attachment of polyethylene glycol (PEG) polymers, which increases the hydrodynamic volume of the protein and thereby slows its clearance by kidney filtration. (See, Clark, R., et al., 1996, J. Biol. Chem. 271: 21969–21977). We have generated PEGylated Axokine by covalently linking polyethylene glycol (PEG) to Ax-13. We have also developed a purification methodology to separate different PEGylated forms of Axokine from unmodified molecules. PEGylated Ax-13 has better solubility and stability properties, at physiological pH, than unPEGylated Ax-13. PEGylation has been shown to greatly enhance pharmacokinetic properties of Ax-13 and would be expected to similarly enhance the properties of other Axokine molecules.

Purified Ax-13 derived from E. coli was used for these studies. 20 kD mPEG-SPA was obtained from Shearwater Polymers, Bicine from Sigma, and Tris-Glycine precast gels from Novex, CA. A small scale reaction study was set up to determine reaction conditions. 20 kD mPEG SPA was reacted with purified Ax-13 at a final concentration of 0.6 mg/ml, at 4° C. in an amine-free buffer at a pH of 8.1. Molar ratios of PEG to protein were varied and two reaction times were used. The reaction was stopped by the addition of a primary amine in large excess. Reaction products were analyzed by reducing SDS-PAGE. The predominant modified species ran at a molecular weight of approximately 60 kD. Higher order modified bands that ran at higher molecular weights were also seen. Based on this study, an overnight reaction at a PEG-to-protein ratio of 4 was chosen. Ax-13 at 0.6 mg/mL was reacted with 20 kD mPEG SPA in a Bicine buffer overnight at 4° C. at a pH of 8.1. The reaction was stopped by the addition of a primary amine in large excess. The reaction product was diluted with a low salt buffer and applied to an ion-exchange column. The column was washed with a low salt buffer and eluted with a NaCl gradient. A good separation between higher order forms (apparent MW>66 kD on SDS-PAGE), a distinct modified species that ran at about 60 kD and unmodified Ax-13 was obtained. Fractions corresponding to the 60 kD band were tested in a Bioassay. A very faint band of unmodified Ax-13 was noticed in the fractions corresponding to the 60 kD band. To ensure that the bioassay results were not influenced significantly by this material, the 60 kD band was further purified by Size exclusion chromatography (SEC) that resulted in baseline separation between unmodified Ax-13 and the 60 kD band. The purified modified Ax-13 was tested in a Bioassay and the results were indistinguishable from those obtained with the material prior to SEC.

Example 9

Construction of Ax-15 Expression Plasmid pRG643

The expression plasmid pRG632 is a high copy plasmid that encodes ampicillin resistance and the gene for human CNTF-C17A,Q63R, ΔC13 (SEQ ID NO:25)(also referred to herein as either Ax1 or Ax-13) with a unique EagI restriction enzyme recognition sequence 3' to the stop codon. This plasmid was used to construct a human CNTF mutation C17A,Q63R, ΔC15 (designated Ax-15) by PCR amplification of a 187 bp BseR I-EagI DNA fragment that incorporates the ΔC15 mutation. The 5' primer {ΔC15-5' (5'-CCA-GATAGAGGAGTTAATGATACTCCT-3'[SEQ ID NO 20])} encodes the BseR I site and the 3' primer ΔC15-3' {(5'-GCGTCGGCCGCGGACCACGCTCATTAC-CCAGTCTGTGA GAAGAAATG-3' [SEQ ID NO: 21])} encodes the C-terminus of the Ax-15 gene ending at Gly185 followed by two stop codons and an EagI restriction enzyme recognition sequence. This DNA fragment was digested with BseR I and EagI and ligated into the same sites in pRG632. The resulting plasmid, pRG639, encodes the gene for Ax-15 (human CNTF C17A,Q63R, ΔC15)(SEQ ID NO:22). The ΔC15 mutation was then transferred as a 339 bp HindIII-EagI DNA fragment into the corresponding sites within pRG421, a high copy number expression plasmid encoding the gene for kanamycin resistance and human CNTF C17A,Q63R, ΔC13 (SEQ ID NO:24). The resulting plasmid, pRG643, encodes the gene for Ax-15 under transcriptional control of the lacUV5 promoter, and confers kanamycin resistance. The Ax-15 gene DNA sequence was confirmed by sequence analysis.

Example 10

Small Scale Expression and Purification of Ax-15 Protein

E. coli strain RFJ141 containing pRG639 was grown in LB medium and expression of Ax-15 protein was induced by the addition of lactose to 1% (w/v). Induced cells were harvested by centrifugation, resuspended in 20 mM Tris-HCl, pH 8.3, 5 mM EDTA, 1 mM DTT, and lysed by passage through a French pressure cell at 10,000 psi. The cell lysate was centrifuged and the pellet was resuspended in 8 M guanidinium-HCl, 50 mM Tris-HCl, pH 8.3, 0.05 mM EDTA then diluted with 5 volumes of 50 mM Tris-HCl, pH 8.3, 0.05 mM EDTA (Buffer A) followed by dialysis against Buffer A. The dialysate was loaded onto a Q-sepharose column equilibrated with Buffer A. The Ax-15 protein was eluted by a linear gradient to 1 M NaCl in 10 column volumes of buffer. Fractions containing Ax-15 were pooled and brought to 1 M $(NH_4)_2SO_4$ by the slow addition of solid $(NH4)_2SO_4$ while maintaining the pH at 8.3 by the addition of NaOH. The pool was loaded onto a phenyl-sepharose column equilibrated with 1 M $(NH_4)_2SO_4$ in Buffer A. The column was washed with 0.5 M $(NH_4)_2SO_4$ in Buffer A, and the Ax-15 protein was eluted by a linear gradient of decreasing $(NH_4)_2SO_4$ concentration. Fractions containing Ax-15 protein were pooled, dialyzed against 5 mM $NaPO_4$, pH 8.3, then concentrated by ultrafiltration. The concentrated pool was fractionated on an Sephacryl S-100 column equilibrated with 5 mM $NaPO_4$, pH 8.3.

Example 11

Large Scale Expression and Purification of Ax-15 Protein

A recombinant, kanamycin resistant *E. Coli* strain RFJ141 expressing the Ax-15 protein under lac promoter control (pRG643) was grown to an intermediate density of 30–35 $AU_{550}$ (Absorbance @ 550 nM) in a minimal salts, glucose medium containing 20 µg/ml Kanamycin. Expression of Ax-15 protein was induced by addition of IPTG (isopropyl thiogalactoside) to 1.0 mM and the fermentation was continued for an additional 8 hr. Ax-15 protein was expressed as insoluble inclusion bodies following IPTG induction. Post-induction, cells were harvested, cell paste concentrated, and buffer exchanged to 20 mM Tris, 1.0 mM DTT, 5.0 mM EDTA, pH 8.5 via AGT 500,000 molecular weight cut off (mwco) hollow fiber diafiltration (ACG Technologies, Inc.). Inclusion bodies were released from the harvested cells by disruption via repeated passage of cooled (0–10° C.) cell paste suspension through a continuous flow, high pressure (>8,000 psi) Niro Soavi homogenizer. The homogenate was subjected to two passages through a cooled (4–8° C.) continuous flow, high speed (>17,000×G) Sharples centrifuge (source) to recover inclusion bodies. Recovered inclusion bodies were extracted in 8.0 M Guanidine HCL with 1.0 mM DTT. The Ax-15 protein/guanidine solution was diluted into 50 mM Tris-HCl, 1.0 mM DTT, 0.05 mM EDTA, pH 8.0–8.3, and diafiltered versus diluent buffer with AGT 5,000 mwco hollow fiber filters (ACG Technologies, Inc.). The resulting solution, containing refolded Ax-15, was filtered through a Microgon 0.22 µm hollow fiber filter (ACG Technologies, Inc.) prior to chromatographic purification.

Example 12

Column Chromatographic Purification of Refolded Ax-15

The filtered Ax-15 solution described above was loaded onto a 16.4 L DEAE Sepharose (Pharmacia) column at 10.9 mg/ml resin and washed with 50 L of 50 mM Tris, pH 8.0–8.3, 1.0 mM DTT, and 0.05 mM EDTA buffer. The Ax-15 protein was eluted from the column with a 120 mM NaCl step in the same Tris buffer. Eluate exceeding a previously established 280 nM absorbance criteria of 40% maximum $A_{280}$ on the ascending portion of the peak and 20% of maximum $A_{280}$ on the descending portion of the peak was pooled and either stored frozen (−30° C.) or used in the next step of the purification procedure. Pooled eluted Ax-15 protein was adjusted to 1.0 M ammonium sulfate by gradual addition of the solid compound, maintaining the pH at 8.0–8.3. The solution was filtered through a 0.22 µm Sartorious capsule filter, loaded onto a 12.5 L phenyl Sepharose HP (Pharmacia) column at 8.24 mg/ml of resin, and washed with 55 L of 1.0 M ammonium sulfate in 50 mM Tris buffer with 0.05 mM EDTA, pH 8.0–8.3. Following a 12.0 L wash with 250 mM ammonium sulfate in the same Tris buffer, the Ax-15 protein was eluted with a 125 mM ammonium sulfate, Tris buffer wash step. Eluate exceeding previously established 280 nM absorbance criteria of 100% maximum $A_{280}$ on the ascending portion of the peak and 20% of maximum $A_{280}$ on the descending portion of the peak was pooled. Eluate was simultaneously diluted 1:4 into 50 mM Tris, pH 8.0–8.3 buffer without salt to reduce its conductivity. Pooled material was stored frozen (−30° C.) or used in the following step. Pooled hydrophobic interaction chromatography (HIC) material was concentrated to 25 L and diafiltered versus 5.0 mM sodium phosphate buffer pH 8.0–8.3 using a 5,000 mwco AGT hollow fiber filter (ACG Technologies, Inc.). The pH was adjusted to 7.0–7.2 immediately prior to sulfyl propyl fast flow (SP FF) sepharose chromatography by gradual addition of concentrated (85%) phosphoric acid. The pH-adjusted pooled material was loaded onto a 7.7 L SP FF sepharose (Pharmacia) column to 9.0 mg/ml of resin and washed with a minimum of 25 L of 5.0 mM sodium phosphate buffer, pH 7.0. The Ax-15 protein was eluted with a 77.0 L step of 5.0 mM sodium phosphate, 130 mM NaCl, pH 7.0–7.2. The eluate was simultaneously diluted 1:5 into 10.0 mM sodium phosphate, pH 9.0–9.2 buffer without salt to reduce conductivity and increase pH. Peak material exceeding 20% maximum $A_{280}$ on the ascending portion of the peak and 20% of the maximum $A_{280}$ on the descending portion of the peak was pooled. Pooled Ax-15 protein was stored frozen (−30° C.) or used in the following step. Pooled SP FF sepharose Ax-15 protein was concentrated and diafiltered versus 5.0 mM sodium phosphate, pH 8.0–8.3 buffer with a 5,000 mwco AGT hollow fiber filter (ACG Technologies, Inc.). The pool (24.66 g) was concentrated to ≦5.0 L. Concentrated, diafiltered Ax-15 protein was loaded onto a 50 L S-100 Sephacryl (Pharmacia) sizing column and eluted with 250 L of the same 5.0 mM sodium phosphate buffer, pH 8.0–8.3. Peak material exceeding 40% maximum $A_{280}$ on the ascending portion of the peak and 40% of the maximum $A_{280}$ on the descending portion of the peak was pooled. The pooled Ax-15 protein was filtered through Millipak 0.22 µm filters and stored at −80° C. prior to dispensing or formulation. The amino acid sequence of Ax-15 produced follows. Alternatively, one could produce a sequence which contains a Methionine residue before the initial Alanine.

```
          9         19         29         39         49         59  (SEQ ID NO: 22)
          *          *          *          *          *          *
    AFTEHSPLT  PHRRDLASRS IWLARKIRSD LTALTESYVK HQGLNKNINL DSADGMPVAS 69         79         89         99        109        119
          *          *          *          *          *          *
    TDRWSELTEA ERLQENLQAY RTFHVLLARL LEDQQVHFTP TEGDFHQAIH TLLLQVAAFA 129        139        149        159        169        179
          *          *          *          *          *          *
    YQIEELMILL EYKIPRNEAD GMPINVGDGG LFEKKLWGLK VLQELSQWTV RSIHDLRFIS

*
    SHQTG
```

```
            10          20          30          40          50          60   (SEQ ID NO: 23)
             *           *           *           *           *           *
    MAFTEHSPLT  PHRRDLASRS  IWLARKIRSD  LTALTESYVK  HQGLNKNINL  DSADGMPVAS 70          80          90         100         110         120
             *           *           *           *           *           *
    TDRWSELTEA  ERLQENLQAY  RTFHVLLARL  LEDQQVHFTP  TEGDFHQAIH  TLLLQVAAFA 130         140         150         160         170         180
             *           *           *           *           *           *
    YQIEELMILL  EYKIPRNEAD  GMPINVGDGG  LFEKKLWGLK  VLQELSQWTV  RSIHDLRFIS

*
    SHQTG
```

Example 13

Use of Ax-15 to Treat Obesity

Animal Models:

Normal Mice

Normal (8 weeks) C57BL/6J mice were obtained from Taconic. The mice received daily subcutaneous injections of vehicle or Ax-15. The animals were weighed daily and food intake over 24-hours was determined between days 3 and 4.

ob/ob Mice

As a result of a single gene mutation on chromosome 6, ob/ob mice produce a truncated, non-functional gene product (Leptin). These mice are hyperphagic, hyperinsulinemic, and markedly obese.

C57BL/6J ob/ob mice were obtained from Jackson Laboratory and used for experiments at 12–14 weeks of age. The mice received daily subcutaneous injection of vehicle, Ax-15, or leptin. Pair-fed group was given the average amount (g) of food consumed by animals treated with Ax-15 (0.3 mg/kg). Body weights were obtained daily and food intake over 24-hours was determined between days 3 and 4. On day 8, the animals were sacrificed and carcass analysis was performed.

Diet-induced Obesity (DIO) Mice

AKR/J mice have been shown to be very susceptable to diet induced obesity by increasing body fat content. Although the gene-environment (diet) interaction is not completely known regarding this kind of dietary obesity, like in human obesity, the genotype is polygenic.

AKR/J mice were obtained from Jackson Laboratory and put on a high fat diet (45% fat; Research Diets) at age 10–12 weeks old. All experiments commenced after 7 weeks on high fat diet. The mice received daily subcutaneous injection of vehicle, Ax-15, or Leptin. Pair-fed group was given the average amount (g) of food consumed by animals treated with Ax-15 (0.1 mg/kg). The animals were weighed daily and food intake over 24-hours was determined between days 3 and 4. On day 8, the animals were sacrificed and sera were obtained for insulin and corticosterone measurements.

II. Reagents:

Recombinant human Ax-15 was manufactured as set forth above and Leptin was purchased from R & D Systems.

Results

Normal Mice

Figure 17:
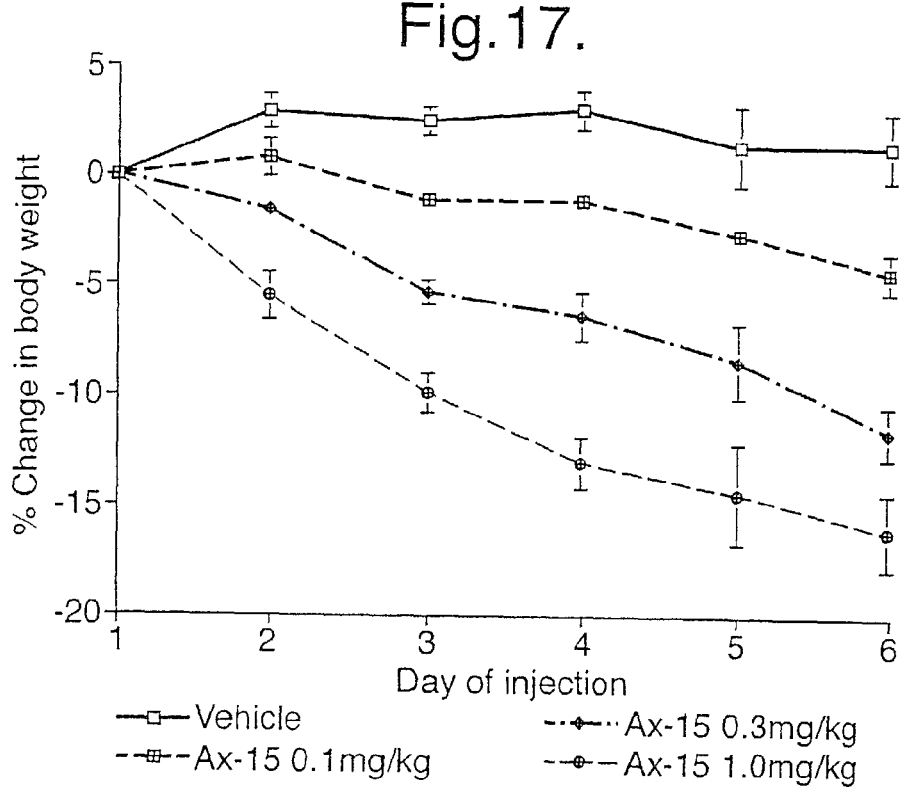
FIG. 17—Effects of Axokine-15 (Ax-15) in normal mice. Normal C57BL/6J mice were injected subcutaneously daily for 6 days with either vehicle or Ax-15 at 0.1 mg/kg, 0.3 mg.kg, or 1.0 mg/kg. Percent change in body weight in Ax-15-treated versus vehicle-treated controls is shown.

Ax-15 reduced body weight in normal mice in a dose dependent manner. In 6 days, the animals lost approximately 4%, 11%, and 16% of their body weight at 0.1 mg/kg, 0.3 mg/kg, and 1 mg/kg, respectively (FIG. 17).

ob/ob Mice

Figure 18:
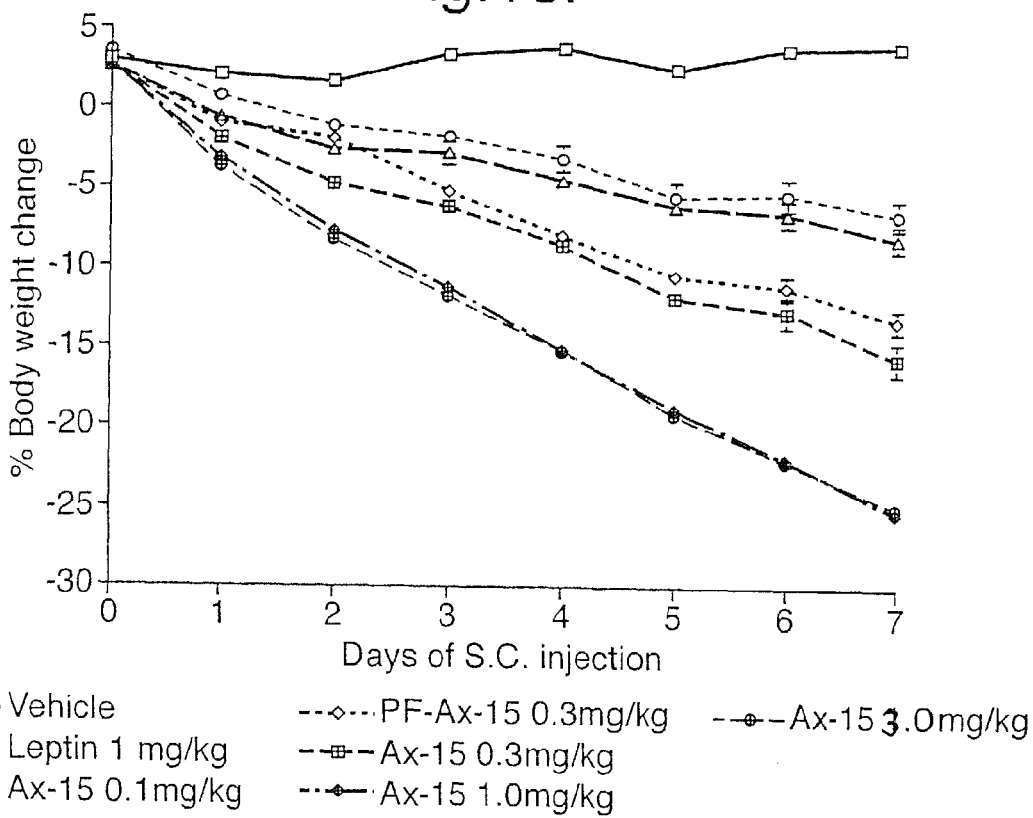
FIG. 18—Effects of Ax-15 in ob/ob mice. C57BL/6J ob/ob mice were injected subcutaneously daily for 7 days with either vehicle, leptin (1.0 mg/kg) or Ax-15 at 0.1 mg/kg, 0.3 mg.kg, or 1.0 mg/kg. Diet-restricted, pair-fed mice were injected with 0.3 mg/kg Ax-15 to investigate the effects of food intake reduction on weight loss. Percent change in body weight in Ax-15-treated and leptin-treated versus vehicle-treated controls is shown.

There was a dose related (0.1 mg/kg–3 mg/kg) decrease in body weight after Ax-15 treatment in ob/ob mice (FIG. 18). At a dose range of 0.1 mg/kg to 3 mg/kg, there was a 8%–25% reduction of body weight. Animals pair-fed to a specific dose of Ax-15 (0.3 mg/kg) showed equivalent loss of body weight as the mice given that dose of Ax-15, suggesting food intake is the primary cause of weight reduction.

Leptin was also effective in decreasing body weight in ob/ob mice. At 1 mg/kg, leptin decreased body weight 6% in 7 days, following a course almost identical to that of Ax-15 given at 0.1 mg/kg (FIG. 18).

Carcass analysis showed that there was a significant reduction of total body fat with Ax-15 and Leptin treatments as well as in pair-fed controls (Table 5). There was a small but non-significant loss of lean mass in all groups as compared to vehicle control animals. Mice receiving only food restriction (pair-fed) had a fat/lean mass ratio no different from vehicle controls, indicating that they lost fat and lean mass equally. However, the Ax-15 and Leptin treated animals showed preferential loss of body fat as reflected by a decrease in fat/lean mass ratio (Table 5).

DIO Mice

Figure 19:
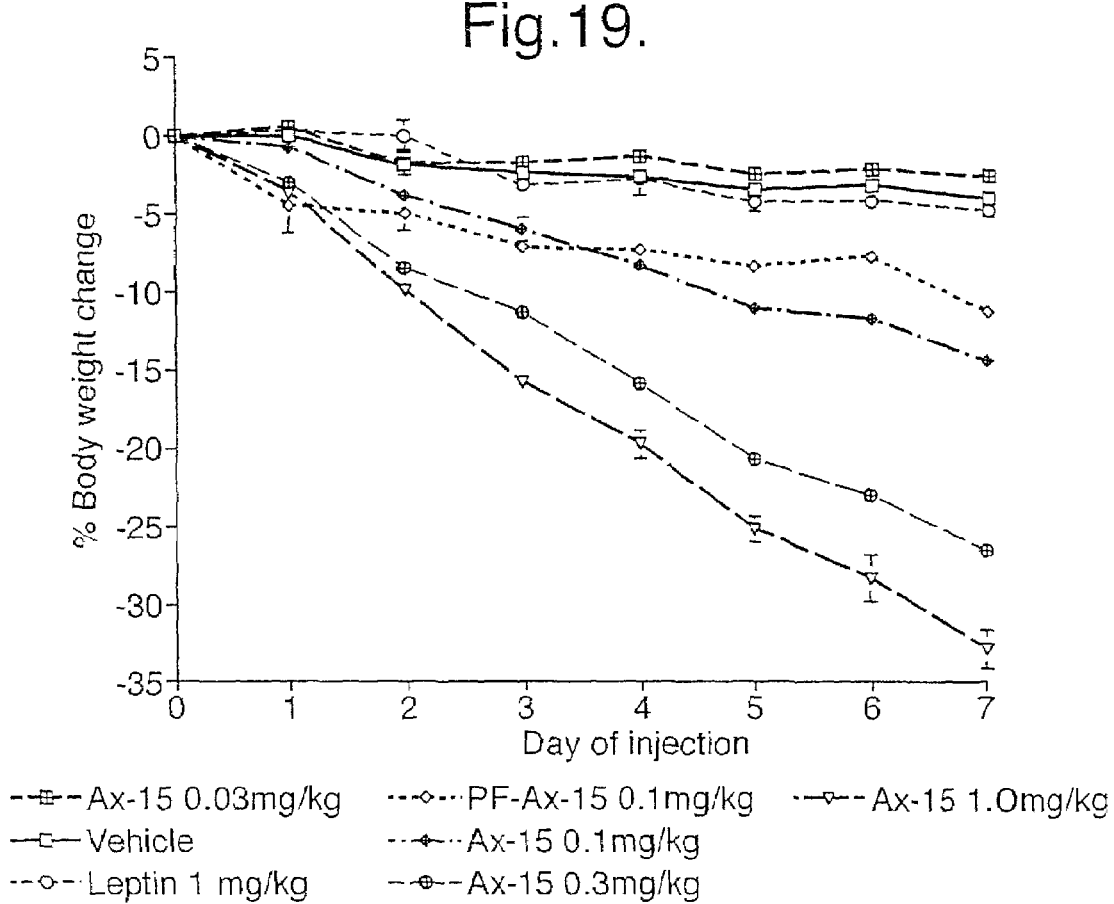
FIG. 19—Effects of Ax-15 in diet-induced obesity in mice. AKR/J mice were placed on a high fat diet for seven weeks prior to treatment with vehicle, leptin (1.0 mg/kg) or Ax-15 at 0.03 mg/kg, 0.1 mg/kg, 0.3 mg/kg, or 1.0 mg/kg. Diet-restricted, pair-fed AKR/J mice were injected with 0.3 mg/kg Ax-15 to investigate the effects of food-intake reduction on weight loss. Percent change in body weight in Ax-15-treated and leptin-treated versus vehicle-treated controls is shown.
Figure 20A:
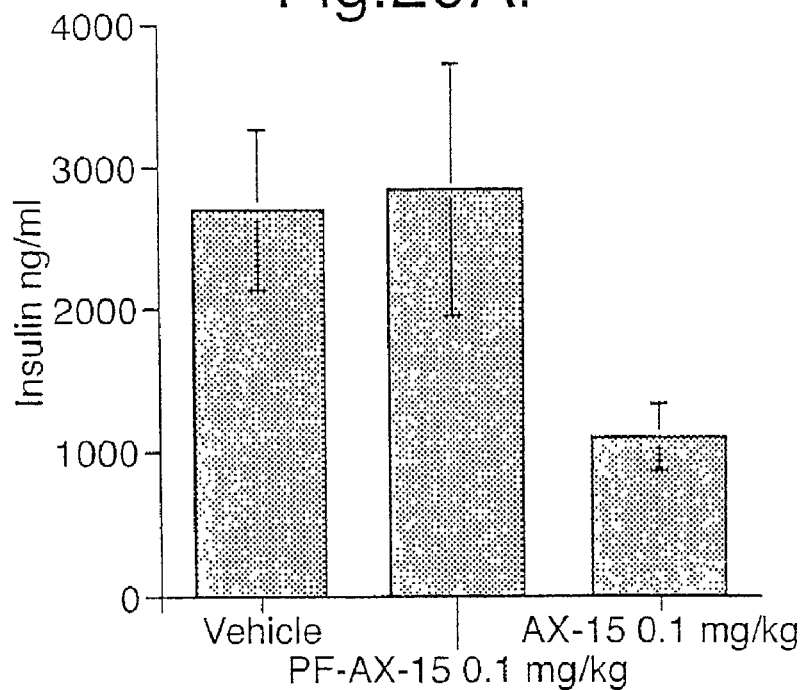
FIGS. 20A and 20B—Effects of Ax-15 and diet restriction on serum insulin and corticosterone levels in diet-induced obese AKR/J mice.
Figure 20B:
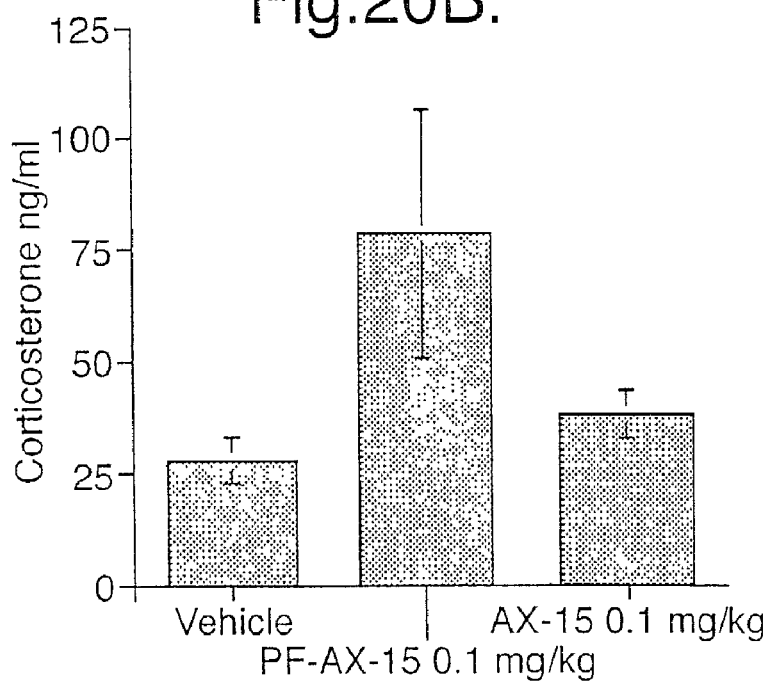

Ax-15 reduced body weight in DIO mice dose dependently. Within one week, the animals lost approximately 14%, 26%, and 33% of their body weight when given Ax-15 at 0.1 mg/kg, 0.3 mg/kg, and 1 mg/kg, respectively (FIG. 19). Comparing the effects of the Ax-15 treatment and the pair-fed control animals, there was a small but significant difference between the 2 groups, suggesting that decrease food intake was probably the primary, although not the only, cause of weight loss with Ax-15 treatment. Indeed, Ax-15 significantly attenuated the obesity associated hyperinsulinemia in DIO mice, whereas merely reducing food intake (pair-fed) did not (FIG. 20A). In addition, Ax-15 did not cause elevation of corticosterone levels, which is a common effect of food restriction (FIG. 20B). It is of interest to note that when Ax-15 was administered in the same dose range (0.1–1 mg/kg), DIO mice lost more than twice the body weight when compared to normal mice (see FIG. 17). This higher sensitivity of diet-induced obese animals to Ax-15 suggests that adiposity may regulate the efficacy of Ax-15 such that Ax-15 will not cause continuous weight loss after adiposity is normalized.

DIO mice are leptin resistant; no weight loss effect was observed in these animals with daily injection of leptin (1 mg/kg; FIG. 19).

We conclude as follows:

1. Ax-15 caused weight loss in normal mice in a dose dependent manner.

2. Ax-15 induced weight loss in ob/ob mice in a dose dependent manner. Ax-15 (0.1 mg/kg) was as effective as Leptin (1 mg/kg) in causing weight loss in ob/ob mice. Both Ax-15 and Leptin treatments, but not pair-fed, preferentially reduced total body fat over lean mass.

3. Ax-15 caused weight loss in diet-induced obesity mice in a dose dependent manner, whereas Leptin was ineffective. Ax-15 treatment attenuated obesity associated hyperinsulinemia in DIO mice; this effect was not observed in pair-fed control animals. In addition, Ax-15 was more effective in inducing weight loss in DIO mice than normal or ob/ob mice. Taken together, our results suggest a specific useful application of Ax-15 in the treatment of leptin resistant obesity, such as type II diabetes associated obesity.

4. The effectiveness of Ax-15 in reducing body weight in leptin resistant mouse model suggests that Ax-15 may also be effective in reducing body weight in obese humans who are resistant or unresponsive to Leptin.

TABLE 5

Results from carcass analysis of ob/ob mice

|  | Fat g | Lean mass g | Fat:Lean mass |
|---|---|---|---|
| Vehicle |  |  |  |
| Mean | 34.77 | 4.79 | 7.26 |
| sem | 1.41 | 0.24 |  |
| Pair-fed to Ax-15 0.3 mg/kg | 29.36 | 4.03 | 7.28 |
|  | 0.93 | 0.07 |  |
| Ax-15 0.1 mg/kg | 30.22 | 4.38 | 6.9 |
|  | 0.59 | 0.13 |  |
| Ax-15 0.3 mg/kg | 26.77 | 4.03 | 6.64 |
|  | 0.66 | 0.08 |  |
| Ax-15 1 mg/kg | 23.29 | 3.35 | 6.95 |
|  | 0.87 | 0.12 |  |
| Ax-15 3 mg/kg | 23 | 3.5 | 6.57 |
|  | 0.53 | 0.12 |  |
| Leptin 1 mg/kg | 28.89 | 4.73 | 6.11 |
|  | 0.89 | 0.1 |  |

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. A modified human ciliary neurotrophic factor protein, comprising the amino acid sequence of SEQ ID NO:22 or 23.

2. A composition comprising a modified human ciliary neurotrophic factor protein comprising the amino acid sequence of SEQ ID NO:22 or 23, and a carrier.

* * * * *